US008501693B2

(12) United States Patent
Kim et al.

(10) Patent No.: US 8,501,693 B2
(45) Date of Patent: Aug. 6, 2013

(54) USE OF EXENDINS AND EXENDIN AGONISTS AND GLP-1 RECEPTOR AGONISTS FOR ALTERING THE CONCENTRATION OF FIBRINOGEN

(75) Inventors: Dennis Kim, La Jolla, CA (US); Michael Trautmann, Hamburg (DE)

(73) Assignees: Amylin Pharmaceuticals, LLC, San Diego, CA (US); Astrazeneca Pharmaceuticals LP, Wilmington, DE (US)

(*) Notice: Subject to any disclaimer, the term of this patent is extended or adjusted under 35 U.S.C. 154(b) by 218 days.

(21) Appl. No.: 12/375,734

(22) PCT Filed: Aug. 6, 2007

(86) PCT No.: PCT/US2007/017621
§ 371 (c)(1),
(2), (4) Date: Sep. 25, 2009

(87) PCT Pub. No.: WO2008/019147
PCT Pub. Date: Feb. 14, 2008

(65) Prior Publication Data
US 2010/0144621 A1    Jun. 10, 2010

Related U.S. Application Data

(60) Provisional application No. 60/835,436, filed on Aug. 4, 2006.

(51) Int. Cl.
*A61K 38/36* (2006.01)
*A61K 38/00* (2006.01)

(52) U.S. Cl.
USPC ............ 514/13.6; 514/1.1; 514/7.2; 514/11.7

(58) Field of Classification Search
None
See application file for complete search history.

(56) References Cited

U.S. PATENT DOCUMENTS

| 5,359,030 | A  | 10/1994 | Ekwuribe |
| 5,512,549 | A  | 4/1996  | Chen et al. |
| 5,681,811 | A  | 10/1997 | Ekwuribe |
| 6,268,343 | B1 | 7/2001  | Knudsen et al. |
| 6,552,167 | B1 | 4/2003  | Rose |
| 6,569,832 | B1 | 5/2003  | Knudsen et al. |
| 6,956,026 | B2 | 10/2005 | Beeley et al. |
| 7,144,863 | B2 | 12/2006 | DeFelippis et al. |
| 7,220,721 | B1 | 5/2007  | Beeley et al. |
| 7,223,725 | B1 | 5/2007  | Beeley et al. |

| 2004/0180824 | A1* | 9/2004 | Knudsen ................. 514/12 |
| 2005/0043228 | A1* | 2/2005 | DeFelippis et al. ........ 514/12 |
| 2005/0059601 | A1  | 3/2005 | Beeley et al. |
| 2005/0101537 | A1  | 5/2005 | Beeley et al. |
| 2007/0093417 | A1  | 4/2007 | Hansen et al. |

FOREIGN PATENT DOCUMENTS

| WO | WO 98/43658    | 10/1998 |
| WO | WO 2006/124529 | 11/2006 |
| WO | WO 2007/068718 | 6/2007  |

OTHER PUBLICATIONS

Roges et al., Expert Opin. Investig. Drugs, 14: 705-727, 2005.*
Courrèges et al., Liraglutide treatment, blood pressure and biomarkers of cardiovascular risk in patients with type 2 diabetes: 14 weeks monotherapy study, *Diabetologia* 49(Suppl. 1):4 (Sep. 2006).
Deacon, Therapeutic strategies basedon glucagon-like peptide-1, *Diabetes* 53:2181-2189 (2004).
Gardiner et al., Mesenteric vasoconstriction and hindquarters vasodilatation accompany the pressor actions of exendin-4 in conscious rats, *The J. Pharmacology and Experimental Therapeutics* 316:852-859 (Feb. 2006).
Hood et al., Use of exenatide in patients with type 2 diabetes, *Diabetes Spectrum* 19:181-186 (Jul. 2006).
Katpiza et al., Long-term treatment with exenatide improved postprandial glycaemic control and was associated with a shift from small to large HDL and LDL particles, *Diabetologia* 49(Suppl.1):140-41 (Sep. 2006).
Linnebjerg et al., Exenatide delays gastric emptying and reduces post-prandial glucose in type 2 diabetes, *Diabetologia* 49(Suppl. 1):140 (Sep. 2006).
Tutunco et al., Exendin-4 rapidly activates eNOS and protects human coronary artery endothelial cells against glucolipoapoptosis, *Diabetologia* 49(Suppl. 1):146 (Sep. 2006).
Busso, Nathalie et al., "Circulating CD26 is negatively associated with inflammation in human and experimental arthritis", American Journal of Pathology 166(2):433-442, Feb. 2005.
Grouzmann, Eric et al., "Loss of dipeptidylpeptidase IV activity in chronic rhinosinusitis contributes to the neurogenic inflammation induced by substance P in the nasal mucosa[1]", FASEB Journal 16:1132-1134, Jul. 2002.
Jones, Barry et al., "Hematopoietic stimulation by a dipeptidyl peptidase inhibitor reveals a novel regulatory mechanism and therapeutic treatment for blood cell deficiencies", Blood 102(5):1641-1648, Sep. 1, 2003.
Lankas, George R. et al., "Dipeptidyl peptidase IV inhibition for the treatment of type 2 diabetes", Diabetes 54:2988-2994, Oct. 2005.

* cited by examiner

*Primary Examiner* — Gyan Chandra
(74) *Attorney, Agent, or Firm* — Womble Carlyle Sandridge & Rice, LLP; Mark J. Pino; Alireza Behrooz

(57) ABSTRACT

The present invention relates to altering the concentration of fibrinogen, specifically, for example, by decreasing fibrinogen concentration. The present invention also relates to methods for improving the cardiovascular risk profile of a subject by decreasing fibrinogen concentration.

19 Claims, No Drawings

USE OF EXENDINS AND EXENDIN AGONISTS AND GLP-1 RECEPTOR AGONISTS FOR ALTERING THE CONCENTRATION OF FIBRINOGEN

CROSS-REFERENCE TO RELATED PATENT APPLICATIONS

This application claims the benefit of U.S. Provisional Application No. 60/835,436, filed Aug. 4, 2006, entitled "Use of Exendins and Exendin Agonists for Altering the Concentration of Fibrinogen", which is incorporated herein by reference in its entirety and for all purposes.

SEQUENCE LISTING

The instant application contains a Sequence Listing which has been submitted in ASCII format via EFS-Web and is hereby incorporated by reference in its entirety. The ASCII copy, created on Apr. 28, 2011, is named 235USUTL.txt and is 77,015 bytes in size.

FIELD OF THE INVENTION

Disclosed herein are methods relating to altering the concentration of fibrinogen, specifically, for example, by decreasing fibrinogen concentration. Also disclosed are methods for improving the cardiovascular risk profile of a subject by decreasing fibrinogen concentration.

BACKGROUND OF THE INVENTION

Fibrinogen is a soluble glycoprotein that is synthesized in liver hepatocytes and megakaryocytes. Fibrinogen is useful in forming bridges between platelets and is the precursor to fibrin, a protein involved in the clotting of blood. Elevated fibrinogen levels have been linked to cardiovascular diseases and conditions and other diseases as discussed herein.

Exendins are peptides that were first isolated from the salivary secretions of the Gila monster, a lizard found in Arizona, and the Mexican Beaded Lizard. Exendin-3 (SEQ ID NO: 1) is present in the salivary secretions of *Heloderma horridum*, and exendin-4 (SEQ ID NO: 2) is present in the salivary secretions of *Heloderma suspectum* (Eng, J., et al., *J. Biol. Chem.*, 265:20259-62, 1990; Eng., J., et al., *J. Biol. Chem.*, 267:7402-05, 1992).

Glucagon-like peptide 1 (GLP-1) (SEQ ID NO: 3) is a product of processing of proglucagon. Circulating biologically active GLP-1 is found in several forms including the GLP-1(7-36) amide and GLP-1(7-37) forms. GLP-1 is secreted from gut endocrine cells in response to nutrient ingestion and plays multiple roles in metabolic homeostasis following nutrient absorption. An important locus for regulation of GLP-1 biological activity is the N-terminal degradation of the peptide by Dipeptidyl Peptidase-4 (DPP-4) -mediated cleavage at position 2 alanine of GLP-1(7-37). By convention in the art, the sequence numbering of GLP-1 and analogs customarily begins with residue 7, corresponding to the N-terminal residue of GLP-1(7-37). Unless indicated otherwise, this convention is followed herein.

Disclosed herein are therapeutics and methods of use thereof for decreasing the concentration of fibrinogen in a subject.

SUMMARY OF THE INVENTION

In a first aspect, provided herein are methods of decreasing the concentration of fibrinogen in a subject in need thereof, the method comprising administering to the subject a therapeutically effective amount of an exendin, exendin agonist, or GLP-1 receptor agonist, wherein the concentration of fibrinogen is decreased in the subject.

In another aspect, provided herein are methods of decreasing the concentration of fibrinogen in a subject with an elevated level of fibrinogen, the methods comprising administering to the subject a therapeutically effective amount of an exendin, exendin agonist, or GLP-1 receptor agonist, wherein the concentration of fibrinogen is decreased in the subject.

In another aspect, provided herein are methods of providing an improved cardiovascular risk profile of a subject in need thereof comprising administering to the subject a therapeutically effective amount of an exendin, exendin agonist, or GLP-1 receptor agonist and measuring a decrease in concentration of fibrinogen in the subject, wherein the cardiovascular risk profile of the subject is improved.

In another aspect, provided herein are methods of providing an improved cardiovascular risk profile of a subject with an elevated level of fibrinogen comprising administering to the subject a therapeutically effective amount of an exendin, exendin agonist, or GLP-1 receptor agonist and measuring a decrease in the concentration of fibrinogen in the subject, wherein the cardiovascular risk profile of the subject is improved.

In another aspect, provided herein are methods of treating a subject in need thereof, comprising administering to the subject a therapeutically effective amount of an exendin, exendin agonist, or GLP-1 receptor agonist, wherein the concentration of fibrinogen in the subject is decreased.

In another aspect, provided herein are methods of treating a subject with an elevated level of fibrinogen, comprising administering to the subject a therapeutically effective amount of an exendin, exendin agonist, or GLP-1 receptor agonist, wherein the concentration of fibrinogen in the subject is decreased.

In aspects contemplating administering to a subject in need thereof a therapeutically effective amount of an exendin, exendin agonist or GLP-1 receptor agonist, in certain embodiments decreasing the concentration of fibrinogen in the subject comprises administering a therapeutically effective amount of an exendin or an exendin agonist. In certain embodiments, decreasing the concentration of fibrinogen in the subject comprises administering a therapeutically effective amount of a GLP-1 receptor agonist.

DETAILED DESCRIPTION OF THE INVENTION

Provided herein are methods related generally to altering fibrinogen concentration. The present invention relates, for example, to decreasing fibrinogen concentration. In another non-limiting example, the present invention relates to improving the cardiovascular risk profile of a subject by decreasing fibrinogen concentration in the subject.

In certain embodiments, there are provided herein methods for decreasing the concentration of fibrinogen in a subject in need thereof comprising administering to said subject a therapeutically effective amount of an exendin, exendin agonist, or GLP-1 receptor agonist, wherein the concentration of fibrinogen is decreased in said subject.

In certain embodiments, there are provided herein methods for decreasing the concentration of fibrinogen in a subject with an elevated fibrinogen level comprising administering to the subject a therapeutically effective amount of an exendin, exendin agonist, or GLP-1 receptor agonist, wherein the concentration of fibrinogen is decreased in the subject.

In certain embodiments, the concentration of fibrinogen is decreased in a subject in need by administering an exendin, exendin agonist, or GLP-1 receptor agonist. In certain embodiments, a decrease in the concentration of fibrinogen may be a decrease of any amount.

In further embodiments, the concentration of fibrinogen is decreased by about 0.1 g/L to about 7 g/L, by about 0.1 g/L to about 6 g/L, by about 0.1 g/L to about 5 g/L, by about 0.1 g/L to about 4 g/L, by about 0.1 g/L to about 3 g/L, by about 0.1 g/L to about 2 g/L, by about 0.1 g/L to about 1.5 g/L, by about 0.1 g/L to about 1 g/L, by about 0.15 g/L to about 0.9 g/L, by about 0.2 g/L to about 0.8 g/L, by about 0.25 g/L to about 0.7 g/L, by about 0.25 g/L to about 0.65 g/L, by about 0.3 g/L to about 0.6 g/L, by about 0.35 g/L to about 0.55 g/L, by about 0.4 g/L to about 0.50 g/L, or by about 0.42 g/L to about 0.48 g/L. In further embodiments, the concentration of fibrinogen is decreased by about 0.1 g/L, by about 0.15 g/L, by about 0.2 g/L, by about 0.25 g/L, by about 0.3 g/L, by about 0.35 g/L, by about 0.4 g/L, by about 0.45 g/L, by about 0.5 g/L, by about 0.55 g/L, by about 0.6 g/L, by about 0.65 g/L, by about 0.7 g/L, by about 0.75 g/L, by about 0.8 g/L, by about 0.85 g/L, by about 0.9 g/L, by about 0.95 g/L, by about 1 g/L, by about 1.5 g/L, by about 2 g/L, by about 2.5 g/L, by about 3 g/L, by about 3.5 g/L, by about 4 g/L, by about 4.5 g/L, by about 5 g/L, by about 5.5 g/L, by about 6 g/L by about 6.5 g/L, or by more than about 7 g/L. The term "about" as used herein in the context of a numerical value refers to the numerical value+/−10% of the numeric value, unless indicated otherwise.

In other embodiments, after administration of one or more exendin, exendin agonist, or GLP-1 receptor agonist, the concentration of fibrinogen is decreased by about 1%, about 5%, about 10%, about 20%, about 30%, about 40%, about 50%, about 75%, about 80%, about 85%, about 90%, about 95%, about 98%, or even about 99%, as compared with fibrinogen levels prior to administration of an exendin, exendin agonist, or GLP-1 receptor agonist.

In certain other embodiments, the concentration of fibrinogen in a subject is decreased and the subject's clotting response remains at clinically acceptable levels. In further embodiments, the concentration of fibrinogen in a subject is decreased to the lowest level at which the subject's clotting response remains at clinically acceptable levels. In other embodiments, clinically acceptable levels include fibrinogen levels of at least about 1.0 g/L to about 4.0 g/L, at least about 1.0 g/L to about 2.0 g/L, about at least about 1.0 g/L to about 1.5 g/L, at least about 1.0 g/L to about 2.5 g/L, about 1.5 g/L to about 4.0 g/L, or about 1.5 g/L to about 2.0 g/L. Clinically acceptable levels of fibrinogen for a subject may be determined by a clinician. In certain embodiments, clinically acceptable fibrinogen levels are those levels at which the subject is not at risk for bleeding disorders. In other embodiments, clinically acceptable fibrinogen levels are those levels at which the subject's risk of bleeding disorders can be controlled by one or more medication. In further embodiments, clinically acceptable fibrinogen levels include those fibrinogen levels at which the subject is not at risk for mortality resulting from inability to form blood clots.

In certain embodiments, the concentration of fibrinogen in a subject may be measured from any source available to the skilled artisan. By way of non-limiting example, the concentration of fibrinogen may be measured in whole blood or plasma. In certain embodiments, the concentration of fibrinogen is measured in whole blood. In certain embodiments, the concentration of fibrinogen is measured in plasma. In certain embodiments, the concentration of fibrinogen is not measured in whole blood. In certain embodiments, the concentration of fibrinogen is not measured in plasma. In various embodiments of the present invention, the concentration of fibrinogen is measured in whole blood or plasma, either or both of which may be fresh or frozen.

In certain embodiments, the concentration of fibrinogen in a subject may be measured by any method known by one skilled in the art. In the context of the present invention, the concentration of fibrinogen may be measured for example without limitation by the von Clauss clotting method as well known in the art.

In certain embodiments of the present invention, a subject may include any animal. In other embodiments, a subject may include any mammal. In certain embodiments, a subject is a human. In various other embodiments, a subject may include pets (e.g., dogs and cats), as well as livestock, such as for example without limitation horses, cows, pigs, and sheep.

In other embodiments, the methods described herein comprise the identification of a subject in need of administration of one or more exendin, exendin agonist, or GLP-1 receptor agonist to reduce fibrinogen. In certain embodiments, a subject in need is any subject who would benefit from the administration of one or more exendin, exendin agonist, or GLP-1 receptor agonist to reduce fibrinogen. Any effective criteria may be used to determine that a subject may benefit from administration of one or more exendin, exendin agonist, or GLP-1 receptor agonist to reduce fibrinogen. Procedures for determining a subject who is in need may include, for example, clinical tests, laboratory tests, physical examination, personal interviews and assessment of family history, as well known in the art.

In certain embodiments, a subject in need is any subject who would benefit from a decrease in fibrinogen concentration. Any effective criteria may be used to determine that a subject may benefit from administration of one or more exendin, exendin agonist, or GLP-1 receptor agonist for the reduction of fibrinogen concentration. For example, methods for detecting elevated fibrinogen levels or conditions associated with elevated fibrinogen levels, such as for example cardiovascular diseases or conditions, are known to those of skill in the art.

In certain embodiments, a subject in need is an individual who appears healthy. In certain embodiments, an individual who appears healthy is an individual who has not been diagnosed with one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In certain embodiments, an individual who appears healthy is an individual who has not been diagnosed with any disease or condition selected from the group consisting of diabetes, prediabetes, and one or more cardiovascular diseases or conditions. In certain embodiments, an individual who appears healthy is an individual who does not have one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In certain embodiments, an individual who appears healthy is an individual who does not have any disease or condition selected from the group consisting of diabetes, prediabetes, and one or more cardiovascular diseases or conditions.

In other embodiments, an individual who appears healthy has not been diagnosed with an elevated level of fibrinogen. In further embodiments, an individual who appears healthy does not have an elevated level of fibrinogen. In yet other embodiments, an individual who appears healthy has, but has not been diagnosed with, an elevated fibrinogen level.

In certain embodiments, a subject in need has one or more diseases or conditions associated with elevated fibrinogen levels. In other embodiments, a subject in need has been diagnosed with one or more diseases or conditions associated with elevated fibrinogen levels. In other embodiments, a subject in need is at risk for one or more disease or conditions associated with elevated fibrinogen levels. In certain embodiments, a disease or condition associated with elevated fibrinogen levels is any disease or condition where an increased fibrinogen level has been correlated with the disease or condition. In other embodiments, a disease or condition associated with elevated fibrinogen levels is one in which at least about 10%, at least about 20%, at least about 30%, at least about 40%, at least about 50%, at least about 60%, at least about 70%, at least about 80%, at least about 90%, or more than about 95% of subjects with the disease or condition have an elevated fibrinogen level. In various non-limiting, exemplary embodiments, a disease or condition associated with elevated fibrinogen levels may include acute infection, cancer, trauma, Alzheimer's, vascular dementia, vertigo, disseminated intravascular coagulation, inflammatory disorders, cardiovascular diseases or conditions, prediabetes or diabetes. In certain embodiments, a disease or condition associated with elevated fibrinogen levels may include acute infection, trauma, Alzheimer's, vascular dementia, vertigo, disseminated intravascular coagulation, inflammatory disorders, or prediabetes.

In certain embodiments, a subject in need has one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. Non-limiting examples of inflammatory disorders include rheumatoid arthritis, glomerulonephrities, chronic obstructive pulmonary disease, osteoarthritis, inflammatory bowel disease, and psoriasis. Non-limiting examples of cancer include breast cancer, kidney cancer, pancreatic cancer, bladder cancer and stomach cancer. Various cardiovascular diseases or conditions include by way of non-limiting example angina, arrhythmia, atrial fibrillation, high blood pressure, high cholesterol, myocardial infarction, heart failure, arteriosclerosis, atherosclerosis, angina, stroke, pericarditis, coronary artery disease, hypertrophic cardiomyopathy, and hyperlipidemia. Additional inflammatory disorders, cancers and cardiovascular diseases and conditions are apparent to one of skill in the art. In certain embodiments, a subject in need has one or more diseases or conditions selected from the group consisting of acute infection, trauma, Alzheimer's, vascular dementia, vertigo, disseminated intravascular coagulation, inflammatory disorders, and prediabetes.

In other embodiments, a subject in need has been diagnosed with one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In certain embodiments, a subject in need has been diagnosed with one or more diseases or conditions selected from the group consisting of acute infection, trauma, Alzheimer's, vascular dementia, vertigo, disseminated intravascular coagulation, inflammatory disorders, and prediabetes.

In other embodiments, a subject in need is at risk for one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In other embodiments, a subject in need is at risk for one or more diseases or conditions selected from the group consisting of acute infection, trauma, Alzheimer's, vascular dementia, vertigo, disseminated intravascular coagulation, inflammatory disorders, and prediabetes.

In other embodiments, a subject in need has one or more diseases or conditions selected from the group consisting of acute infection, cancer, trauma, Alzheimer's, vascular dementia, vertigo, disseminated intravascular coagulation, and inflammatory disorders. In other embodiments, a subject in need has one or more diseases or conditions selected from the group consisting of acute infection, trauma, Alzheimer's, vascular dementia, vertigo, disseminated intravascular coagulation, inflammatory disorders, and prediabetes.

In other embodiments, a subject in need has been diagnosed with one or more diseases or conditions selected from the group consisting of acute infection, cancer, trauma, Alzheimer's, vascular dementia, vertigo, disseminated intravascular coagulation, and inflammatory disorders.

In other embodiments, a subject in need is at risk for one or more diseases or conditions selected from the group consisting of acute infection, cancer, trauma, Alzheimer's, vascular dementia, vertigo, disseminated intravascular coagulation, and inflammatory disorders.

In other embodiments, a subject in need has one or more cardiovascular diseases or conditions. In other embodiments, a subject in need has been diagnosed with one or more cardiovascular diseases or conditions.

In other embodiments, a subject in need is at risk for one or more cardiovascular diseases or conditions. Risk factors for cardiovascular diseases or conditions include any risk factor known by one skilled in the art. Non-limiting examples of risk factors for cardiovascular diseases or conditions include age, diabetes, tobacco smoking, elevated cholesterol levels, high levels of LDL, high fibrinogen and PAI-1 blood concentration, high blood pressure, elevated homocysteine, elevated blood levels of asymmetric dimethylarginine, being overweight, being obese, genetic factors, family history of cardiovascular disease, physical inactivity, being male. In certain embodiments, a subject is at risk for diabetes or one or more cardiovascular diseases or conditions or both.

In further embodiments, a subject in need is overweight and obese. While In certain embodiments, obesity is generally defined as a body mass index over 30, in other embodiments, any subject who needs or wishes to reduce body weight is included in the scope of obese. Body mass index (BMI) can be measured by methods well known in the art. In further embodiments, a subject in need is less than 20 years old, 20 years or older, 25 years or older, 35 years or older, 45 years or older, 55 years or older, 65 years or older, 75 years or older, 85 years or older, or 95 years or older. In certain embodiments, a subject is overweight and is 45 years of age or older.

In other embodiments, a subject in need has prediabetes. In other embodiments, a subject in need has been diagnosed with prediabetes.

In other embodiments, a subject in need has diabetes. In other embodiments, a subject in need has been diagnosed with diabetes. In other embodiments, a subject in need is at risk for diabetes. Exemplary non-limiting risk factors for diabetes include being overweight, having hypertension, having high cholesterol, being African American, being Mexican American, being Native American, having a family history of diabetes, having genetic factors, lacking physical inactivity, having impaired glucose tolerance, or having a previous history of gestational diabetes.

In other embodiments, a subject in need has type 1 diabetes, type 2 diabetes or gestational diabetes. In other embodiments, a subject in need has been diagnosed with type 1 diabetes, type 2 diabetes or gestational diabetes. In other embodiments, a subject in need is at risk for type 1 diabetes, type 2 diabetes or gestational diabetes.

In other embodiments, a subject in need has diabetes and one or more cardiovascular diseases or conditions. In other embodiments, a subject in need has been diagnosed with diabetes and one or more cardiovascular diseases or conditions. In other embodiments, a subject in need is at risk for diabetes and one or more cardiovascular diseases or conditions.

In other embodiments, a subject in need has prediabetes and one or more cardiovascular diseases or conditions. In other embodiments, a subject in need has been diagnosed with prediabetes and one or more cardiovascular diseases or conditions.

In other embodiments, a subject in need does not have prediabetes. In other embodiments, a subject in need does not have diabetes. In other embodiments, a subject in need does not have one or more cardiovascular diseases or conditions. In other embodiments, a subject in need does not have one or more cardiovascular diseases or conditions and diabetes. In other embodiments, a subject in need does not have one or more cardiovascular diseases or conditions and prediabetes. In certain embodiments, a subject in need of fibrinogen lowering is not in need of glucose lowering. In certain embodiments, a subject in need of fibrinogen lowering is not hyperglycemic. In certain embodiments, a subject in need of fibrinogen lowering is normoglycemic. In certain embodiments, a subject in need of fibrinogen lowering is hypoglycemic.

In other embodiments, a subject in need has not been diagnosed with prediabetes. In other embodiments, a subject in need has not been diagnosed with diabetes. In other embodiments, a subject in need has not been diagnosed with one or more cardiovascular diseases or conditions. In other embodiments, a subject in need has not been diagnosed with one or more cardiovascular diseases or conditions and diabetes. In other embodiments, a subject in need has not been diagnosed with prediabetes and diabetes. In other embodiments, a subject in need has not been diagnosed with one or more cardiovascular diseases or conditions and prediabetes.

In other embodiments, a subject in need has a family history of one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. As used herein, a family history means more than one, more than two, more than three, or more than four generations of a family have been diagnosed with a certain disease or condition.

In other embodiments, a subject in need has a family history of one or more diseases or conditions selected from the group consisting of acute infection, cancer, trauma, Alzheimer's, vascular dementia, vertigo, disseminated intravascular coagulation, and inflammatory disorders.

In other embodiments, a subject in need has a family history of diabetes. In other embodiments, a subject in need has a family history of one or more cardiovascular diseases or conditions. In other embodiments, a subject in need has a family history of diabetes and one or more cardiovascular diseases or conditions. In other embodiments, a subject in need has a family history of diabetes or one or more cardiovascular diseases or conditions.

In other embodiments, a subject in need does not have a family history of diabetes. In other embodiments, a subject in need does not have a family history of one or more cardiovascular diseases or conditions. In other embodiments, a subject in need does not have a family history of diabetes and one or more cardiovascular diseases or conditions.

In certain embodiments, a subject in need is a subject who has an elevated fibrinogen level. In certain embodiments, a subject in need has been diagnosed with an elevated fibrinogen level. In the context of the present methods, a subject with an elevated fibrinogen level includes a subject who has (diagnosed or undiagnosed) an elevated fibrinogen level or a subject who has been diagnosed with an elevated fibrinogen level.

In other embodiments, a subject with an elevated fibrinogen level has a fibrinogen concentration that is higher than normal for that subject when healthy. In another aspect, an elevated fibrinogen level is a fibrinogen concentration in a subject that is higher than normal for a healthy population of the same species as the subject. In various embodiments, an elevated fibrinogen level is a concentration that is about 10%, about 25%, about 50%, about 75%, about 100%, about 200%, about 300%, about 500%, about 1000%, or more than about 1000% higher than normal for the subject when healthy or for a healthy population of the same species as the subject.

In further embodiments, an elevated fibrinogen level is a fibrinogen concentration that is greater than about 150 mg/dl, greater than about 200 mg/dl, greater than about 300 mg/dl, greater than about 350 mg/dl, greater than about 400 mg/dl, greater than about 500 mg/dl, greater than about 550 mg/dl, greater than about 600 mg/dl, greater than about 650 mg/dl, greater than about 700 mg/di, greater than about 750 mg/dl, greater than about 800 mg/dl, greater than about 900 mg/dl, greater than about 950 mg/dl, greater than about 1000 mg/dl, or greater than about 1500 mg/dl, measured by the von Clauss clotting method.

In other embodiments, a subject in need is at risk for an elevated fibrinogen level. Exemplary, non-limiting subjects at risk for an elevated fibrinogen level include subjects with acute infection, cancer, trauma, Alzheimer's, vascular dementia, vertigo, disseminated intravascular coagulation, inflammatory disorders, cardiovascular diseases or conditions, prediabetes or diabetes, or a family history of any thereof. Further exemplary non-limiting subjects at risk for an elevated fibrinogen level include subjects with acute infection, trauma, Alzheimer's, vascular dementia, vertigo, disseminated intravascular coagulation, inflammatory disorders, or prediabetes, or a family history of any thereof.

In other embodiments, a subject with or at risk for an elevated fibrinogen level has one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In other embodiments, a subject with or at risk for an elevated fibrinogen level has one or more diseases or conditions selected from the group consisting of acute infection, trauma, Alzheimer's, vascular dementia, vertigo, disseminated intravascular coagulation, inflammatory disorders, and prediabetes.

In other embodiments, a subject with or at risk for an elevated fibrinogen level has been diagnosed with one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In other embodiments, a subject with or at risk for an elevated fibrinogen level has been diagnosed with one or more diseases or conditions selected from the group consisting of acute infection, trauma, Alzheimer's, vascular dementia, vertigo, disseminated intravascular coagulation, inflammatory disorders, and prediabetes.

In other embodiments, a subject with or at risk for an elevated fibrinogen level is at risk for one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes. In other embodiments, a subject with or at risk for an elevated fibrinogen level is at risk for one or more diseases or conditions selected from the group consisting of acute infection, trauma, Alzheimer's, vascular dementia, vertigo, disseminated intravascular coagulation, inflammatory disorders, and prediabetes.

In other embodiments, a subject with or at risk for an elevated fibrinogen level has one or more diseases or conditions selected from the group consisting of acute infection, cancer, trauma, Alzheimer's, vascular dementia, vertigo, disseminated intravascular coagulation, and inflammatory disorders. In other embodiments, a subject with or at risk for an elevated fibrinogen level has one or more diseases or conditions selected from the group consisting of acute infection, trauma, Alzheimer's, vascular dementia, vertigo, disseminated intravascular coagulation, and inflammatory disorders.

In other embodiments, a subject with or at risk for an elevated fibrinogen level has been diagnosed with one or more diseases or conditions selected from the group consisting of acute infection, cancer, trauma, Alzheimer's, vascular dementia, vertigo, disseminated intravascular coagulation, and inflammatory disorders. In other embodiments, a subject with or at risk for an elevated fibrinogen level has been diagnosed with one or more diseases or conditions selected from the group consisting of acute infection, trauma, Alzheimer's, vascular dementia, vertigo, disseminated intravascular coagulation, and inflammatory disorders.

In other embodiments, a subject with or at risk for an elevated fibrinogen level is at risk for one or more diseases or conditions selected from the group consisting of acute infection, cancer, trauma, Alzheimer's, vascular dementia, vertigo, disseminated intravascular coagulation, and inflammatory disorders. In other embodiments, a subject with or at risk for an elevated fibrinogen level is at risk for one or more diseases or conditions selected from the group consisting of acute infection, trauma, Alzheimer's, vascular dementia, vertigo, disseminated intravascular coagulation, and inflammatory disorders.

In other embodiments, a subject with or at risk for an elevated fibrinogen level has one or more cardiovascular diseases or conditions. In other embodiments, a subject with or at risk for elevated level of fibrinogen has been diagnosed with one or more cardiovascular diseases or conditions. In other embodiments, a subject with or at risk for an elevated level of fibrinogen is at risk for one or more cardiovascular diseases or conditions.

In other embodiments, a subject with or at risk for an elevated fibrinogen level has prediabetes. In other embodiments, a subject with or at risk for elevated fibrinogen level has been diagnosed with prediabetes.

In other embodiments, a subject with or at risk for an elevated fibrinogen level has diabetes. In other embodiments, a subject with or at risk for an elevated fibrinogen level has been diagnosed with diabetes. In other embodiments, a subject with or at risk for an elevated fibrinogen level is at risk for diabetes.

In other embodiments, a subject with or at risk for an elevated level of fibrinogen has type 1 diabetes, type 2 diabetes or gestational diabetes. In other embodiments, a subject with or at risk for an elevated level of fibrinogen has been diagnosed with type 1 diabetes, type 2 diabetes or gestational diabetes. In other embodiments, a subject with or at risk for an elevated level of fibrinogen is at risk for type 1 diabetes, type 2 diabetes or gestational diabetes.

In other embodiments, a subject with or at risk for an elevated level of fibrinogen has diabetes and one or more cardiovascular diseases or conditions. In other embodiments, a subject with or at risk for an elevated level of fibrinogen has been diagnosed with diabetes and one or more cardiovascular diseases or conditions. In other embodiments, a subject with or at risk for an elevated level of fibrinogen is at risk for diabetes and one or more cardiovascular diseases or conditions.

In other embodiments, a subject with or at risk for an elevated level of fibrinogen has prediabetes and one or more cardiovascular diseases or conditions. In other embodiments, a subject with or at risk for an elevated level of fibrinogen has been diagnosed with prediabetes and one or more cardiovascular diseases or conditions.

In other embodiments, a subject with or at risk for elevated level of fibrinogen does not have prediabetes. In other embodiments, a subject with or at risk for an elevated level of fibrinogen does not have diabetes. In other embodiments, a subject with or at risk for an elevated level of fibrinogen does not have one or more cardiovascular diseases or conditions.

In other embodiments, a subject with or at risk for an elevated level of fibrinogen does not have one or more cardiovascular diseases or conditions and prediabetes. In other embodiments, a subject with or at risk for an elevated level of fibrinogen does not have one or more cardiovascular diseases or conditions and diabetes.

In other embodiments, a subject with or at risk for elevated level of fibrinogen has not been diagnosed with prediabetes. In other embodiments, a subject with or at risk for an elevated level of fibrinogen has not been diagnosed with diabetes. In other embodiments, a subject with or at risk for an elevated level of fibrinogen has not been diagnosed with one or more cardiovascular diseases or conditions.

In other embodiments, a subject with or at risk for an elevated level of fibrinogen has not been diagnosed with one or more cardiovascular diseases or conditions and prediabetes. In other embodiments, a subject with or at risk for an elevated level of fibrinogen has not been diagnosed with one or more cardiovascular diseases or conditions and diabetes.

In other embodiments, a subject with or at risk for an elevated fibrinogen level has a family history of one or more diseases or conditions selected from the group consisting of acute infection, cancer, trauma, Alzheimer's, vascular dementia, vertigo, disseminated intravascular coagulation, inflammatory disorders, cardiovascular diseases or conditions, prediabetes and diabetes.

In other embodiments, a subject with or at risk for an elevated fibrinogen level has a family history of one or more diseases or conditions selected from the group consisting of acute infection, cancer, trauma, Alzheimer's, vascular dementia, vertigo, disseminated intravascular coagulation, and inflammatory disorders.

In other embodiments, a subject with or at risk for an elevated level of fibrinogen has a family history of diabetes. In other embodiments, a subject with or at risk for an elevated level of fibrinogen has a family history of one or more cardiovascular diseases or conditions. In other embodiments, a subject with or at risk for an elevated level of fibrinogen has a family history of diabetes and one or more cardiovascular diseases or conditions.

In other embodiments, a subject with or at risk for an elevated level of fibrinogen does not have a family history of diabetes. In other embodiments, a subject with or at risk for an elevated level of fibrinogen does not have a family history of one or more cardiovascular diseases or conditions. In other embodiments, a subject with or at risk for an elevated level of fibrinogen does not have a family history of diabetes and one or more cardiovascular diseases or conditions.

In a further embodiment, a subject with or at risk for an elevated level of fibrinogen is overweight. In further embodiments, a subject with or at risk for an elevated level of fibrinogen is less then 20 years old, 20 years or older, 25 years or older, 35 years or older, 45 years or older, 55 years or older, 65 years or older, 75 years or older, 85 years or older, or 95 years or older.

In certain embodiments, a subject in need does not have an elevated fibrinogen level. In certain embodiments, a subject in need does not have an elevated fibrinogen level if said subject has a fibrinogen concentration lower than a subject with an elevated fibrinogen level as defined herein. In other embodiments, not having an elevated fibrinogen level means having a fibrinogen concentration less than about 149 mg/dl, less than about 140 mg/dl, less than about 130 mg/dl, less than about 120 mg/dl, less than about 110 mg/di, less than about 100 mg/dl, less than about 90 mg/dl, less than about 80 mg/dl, less than about 70 mg/dl, less than about 60 mg/dl, less than about 50 mg/dl, less than about 40 mg/di, less than about 30 mg/dl, less than about 20 mg/dl or less than about 10 mg/dl, measured by the von Clauss clotting method.

The present invention also includes and provides a method of providing an improved cardiovascular risk profile of a subject in need thereof comprising administering to the subject a therapeutically effective amount of an exendin, exendin agonist, or GLP-1 receptor agonist and measuring a decrease in concentration of fibrinogen in the subject, wherein the cardiovascular risk profile of the subject is improved.

The present invention also includes and provides a method of providing an improved cardiovascular risk profile of a subject with an elevated level of fibrinogen comprising administering to the subject a therapeutically effective amount of an exendin, exendin agonist, or GLP-1 receptor agonist and measuring a decrease in the concentration of fibrinogen in the subject, wherein the cardiovascular risk profile of the subject is improved.

In certain embodiments, providing an improved cardiovascular risk profile may include administering to a subject in need any exendin, exendin agonist, or GLP-1 receptor agonist. In other embodiments, providing an improved cardiovascular risk profile may include administering any exendin, exendin agonist, or GLP-1 receptor agonist by any mode of administration known to the skilled artisan. Various exemplary, non-limiting exendins, exendin agonist, and GLP-1 receptor agonists, and modes of administration are discussed herein.

In certain embodiments, an improved cardiovascular risk profile is a reduced risk of a cardiovascular disease or condition in a subject. In other embodiments, an improved cardiovascular risk profile is a reduced risk of a cardiovascular disease or condition in a subject who has been previously identified as having one or more risk factors associated with a cardiovascular disease or condition. In certain embodiments, an improved cardiovascular risk profile is elimination of one or more risk factors associated with a cardiovascular disease or condition in a subject previously identified as having one or more risk factors associated with a cardiovascular disease or condition.

In certain embodiments, providing an improved cardiovascular risk profile is accomplished by measuring a decrease in fibrinogen concentration.

The present invention includes and provides a method of treating a subject in need thereof, comprising administering to the subject a therapeutically effective amount of an exendin, exendin agonist, or GLP-1 receptor agonist, wherein the concentration of fibrinogen in the subject is decreased.

The present invention includes and provides a method of treating a subject with an elevated level of fibrinogen, comprising administering to the subject a therapeutically effective amount of an exendin, exendin agonist, or GLP-1 receptor agonist, wherein the concentration of fibrinogen in the subject is decreased.

In certain embodiments, prophylactic treatment is provided. In certain embodiments, prophylactic treatment may include preventing a disease or condition. In other embodiments, prophylactic treatment prevents worsening of a disease or condition. For example, In certain embodiments, prophylactic treatment prevents worsening of an elevated fibrinogen level. In other embodiments, prophylactic treatment maintains a fibrinogen level that is not elevated as unelevated.

In other embodiments, therapeutic treatment is provided. Therapeutic treatment may result, for example without limitation, in ameliorating symptoms of any disease or condition, in reducing a concentration of one or more elevated level, such as for example fibrinogen, in a subject, or in eliminating a disease or condition in a subject.

Treatment on an acute or chronic basis is contemplated. In addition, treatment on an acute basis may be extended to chronic treatment, if so indicated. In certain embodiments, treatment of a subject may include administering any exendin, exendin agonist, or GLP-1 receptor agonist by any mode of administration known to the skilled artisan. Various exemplary, non-limiting modes of administration are discussed herein.

Exendin and Exendin Agonist Compounds

In some embodiments of the methods provided herein, any exendin or exendin agonist may be administered. Exemplary non-limiting exendins and exendin agonists include or comprise exendin-3, exendin-4, and C-terminally truncated exendin peptides of 25, 26, 27, 28, 29, 30, 31, 32, 33, 34, 35, 36, 37, or 38 amino acids in length.

In certain embodiments, exendin agonists include or comprise without limitation exendin-4 acid, exendin-4(1-30), exendin-4(1-30) amide, exendin-4(1-27), exendin-4(1-28), exendin-4(1-28)amide, $^{14}$Leu, $^{25}$Phe exendin-4, $^{14}$Leu exendin-4, $^{14}$Leu exendin-4(1-28) amide, $^{14}$Leu exendin-4(1-28), and $^{14}$Leu, $^{25}$Phe exendin-4(1-28).

Exendin agonist compounds contemplated herein include or comprise without limitation those described in Published Application WO99/07404, filed Aug. 6, 1998, entitled, "Novel Exendin Agonist Compounds," which claims the benefit of U.S. Provisional Application No. 60/055,404, filed Aug. 8, 1997, and corresponding U.S. Pat. No. 6,956,026 issued Oct. 18, 2005, each of which are herein incorporated by reference in their entireties and for all purposes, which purposes include the exendin and exendin agonist compounds and formulations thereof taught therein. Included, for example without limitation, are compounds comprising a structure of Formula I (SEQ ID NO: 12):

Xaa$^1$ Xaa$^2$ Xaa$^3$ Gly Thr Xaa$^4$ Xaa$^5$ Xaa$^6$ Xaa$^7$ Xaa$^8$   I

Ser Lys Gln Xaa$^9$ Glu Glu Glu Ala Val Arg Leu

Xaa$^{10}$ Xaa$^{11}$ Xaa$^{12}$ Xaa$^{13}$ Leu Lys Asn Gly Gly Xaa$^{14}$

Ser Ser Gly Ala Xaa$^{15}$ Xaa$^{16}$ Xaa$^{17}$ Xaa$^{18}$ wherein Xaa$^1$ is His, Arg or Tyr; Xaa$^2$ is Ser, Gly, Ala or Thr; Xaa$^3$ is Ala, Asp or Glu; Xaa$^4$ is Phe, Tyr or naphthylalanine; Xaa$^5$ is Thr or Ser; Xaa$^6$ is Ser or Thr; Xaa$^7$ is Asp or Glu; Xaa$^8$ is Leu, Ile, Val, pentylglycine or Met; Xaa$^9$ is Leu, Ile, pentylglycine, Val or Met; Xaa$^{10}$ is Phe, Tyr or naphthylalanine; Xaa$^{11}$ is Ile, Val, Leu, pentylglycine, tert-butylglycine or Met; Xaa$^{12}$ is Glu or Asp; Xaa$^{13}$ is Trp, Phe, Tyr, or naphthylalanine; Xaa$^{14}$, Xaa$^{15}$, Xaa$^{16}$ and Xaa$^{17}$ are independently Pro, homoproline, 3Hyp, 4Hyp, thioproline, N-alkylglycine, N-alkylpentylglycine or N-alkylalanine; Xaa$^{18}$ is Ser, Thr, Tyr, or C-terminal free acid or amidated derivatives thereof. The term "C-terminal free acid" and like terms in the context of amino acids refers to the presence of a C-terminal carboxylate moiety. The term "C-terminal amidated derivative" and like terms in the context of amino acids refers to the presence of a C-terminal capping amide (e.g., —NH$_2$, —NHR$^1$, —NR$^1$R$^2$, wherein R$^1$ and R$^2$ are independently alkyl, and the like).

In certain embodiments contemplating compounds with structure of Formula I, N-alkyl groups for N-alkylglycine, N-alkylpentylglycine and N-alkylalanine include lower alkyl groups of 1 to about 6 carbon atoms, or in other embodiments 1 to 4 carbon atoms. In certain embodiments, exendin agonist compounds include those wherein Xaa$^1$ is His or Tyr. In certain embodiments, Xaa$^1$ is His. In certain embodiments, compounds are included wherein Xaa$^2$ is Gly. In certain embodiments, compounds are contemplated wherein Xaa$^9$ is Leu, pentylglycine or Met. In certain embodiments, exemplary compounds include without limitation those wherein Xaa$^{13}$ is Trp or Phe.

In certain embodiments contemplating compounds with structure of Formula I, exemplary compounds are those in which Xaa$^4$ is Phe or naphthylalanine, Xaa$^{11}$ is Ile or Val, and Xaa$^{14}$, Xaa$^{15}$, Xaa$^{16}$ and Xaa$^{17}$ are independently selected from the group consisting of Pro, homoproline, thioproline and N-alkylalanine. In certain embodiments, N-alkylalanine has a N-alkyl group of 1 to about 6 carbon atoms. In certain embodiments, Xaa$^{15}$, Xaa$^{16}$ and Xaa$^{17}$ are the same amino acid residue. In certain embodiments, Xaa$^{18}$ is Ser or Tyr.

In certain embodiments, compounds are those of Formula I wherein Xaa$^1$ is His or Tyr; Xaa$^2$ is Gly; Xaa$^4$ is Phe or naphthylalanine; Xaa$^9$ is Leu, pentylglycine or Met; Xaa$^{10}$ is Phe or naphthylalanine; Xaa$^{11}$ is Ile or Val; Xaa$^{14}$, Xaa$^{15}$, Xaa$^{16}$ and Xaa$^{17}$ are independently selected from Pro, homoproline, thioproline or N-alkylalanine; Xaa$^{18}$ is Ser or Tyr, wherein Xaa$^{18}$ is amidated.

In certain embodiments, compounds include those of Formula I wherein: Xaa$^1$ is His or Arg; Xaa$^2$ is Gly; Xaa$^3$ is Ala, Asp or Glu; Xaa$^4$ is Phe or napthylalanine; Xaa$^5$ is Thr or Ser; Xaa$^6$ is Ser or Thr; Xaa$^7$ is Asp or Glu; Xaa$^8$ is Leu or pentylglycine; Xaa$^9$ is Leu or pentylglycine; Xaa$^{10}$ is Phe or naphthylalanine; Xaa$^{11}$ is Ile, Val or t-butylglycine; Xaa$^{12}$ is Glu or Asp; Xaa$^{13}$ is Trp or Phe; Xaa$^{14}$, Xaa$^{15}$, Xaa$^{16}$, and Xaa$^{17}$ are independently Pro, homoproline, thioproline, or N-methylalanine; Xaa$^{18}$ is C-terminal free acid or amidated Ser or Tyr.

In certain embodiments contemplating compounds with structure of Formula I, compounds are contemplated wherein Xaa$^9$ is Leu, Ile, Val or pentylglycine, and Xaa$^{13}$ is Phe, Tyr or naphthylalanine.

In certain embodiments, exendin agonist compounds comprise or include those described in Published Application WO99/25727, filed Nov. 13, 1998, entitled, "Novel Exendin Agonist Compounds," which claims the benefit of U.S. Provisional Application No. 60/065,442, filed Nov. 14, 1997, and corresponding U.S. Pat. No. 7,223,725 issued May 29, 2007, each of which are herein incorporated by reference in their entireties and for all purposes, which purposes include the exendin and exendin agonist compounds and formulations thereof taught therein. Included without limitation are compounds comprising the structure of the Formula II (SEQ ID NO: 13):

Xaa$^1$ Xaa$^2$ Xaa$^3$ Gly Xaa$^5$ Xaa$^6$ Xaa$^7$ Xaa$^8$ Xaa$^9$   II

Xaa$^{10}$ Xaa$^{11}$ Xaa$^{12}$ Xaa$^{13}$ Xaa$^{14}$ Xaa$^{15}$ Xaa$^{16}$

Xaa$^{17}$ Ala Xaa$^{19}$ Xaa$^{20}$ Xaa$^{21}$ Xaa$^{22}$ Xaa$^{23}$ Xaa$^{24}$

Xaa$^{25}$ Xaa$^{26}$ Xaa$^{27}$ Xaa$^{28}$-Z$_1$;

wherein Xaa$^1$ is His, Arg or Tyr; Xaa$^2$ is Ser, Gly, Ala or Thr; Xaa$^3$ is Ala, Asp or Glu; Xaa$^5$ is Ala or Thr; Xaa$^6$ is Ala, Phe, Tyr or naphthylalanine; Xaa$^7$ is Thr or Ser; Xaa$^8$ is Ala, Ser or Thr; Xaa$^9$ is Asp or Glu; Xaa$^{10}$ is Ala, Leu, Ile, Val, pentylglycine or Met; Xaa$^{11}$ is Ala or Ser; Xaa$^{12}$ is Ala or Lys; Xaa$^{13}$ is Ala or Gln; Xaa$^{14}$ is Ala, Leu, Ile, pentylglycine, Val or Met; Xaa$^{15}$ is Ala or Glu; Xaa$^{16}$ is Ala or Glu; Xaa$^{17}$ is Ala or Glu; Xaa$^{19}$ is Ala or Val; Xaa$^{20}$ is Ala or Arg; Xaa$^{21}$ is Ala or Leu; Xaa$^{22}$ is Ala, Phe, Tyr or naphthylalanine; Xaa$^{23}$ is Ile, Val, Leu, pentylglycine, tert-butylglycine or Met; Xaa$^{24}$ is Ala, Glu or Asp; Xaa$^{25}$ is Ala, Trp, Phe, Tyr or naphthylalanine; Xaa$^{26}$ is Ala or Leu; Xaa$^{27}$ is Ala or Lys; Xaa$^{28}$ is Ala or Asn; Z$_1$ is absent or —OH, —NH$_2$, Gly-Z$_2$, Gly Gly-Z$_2$, Gly Gly Xaa$^{31}$-Z$_2$, Gly Gly Xaa$^{31}$ Ser-Z$_2$, Gly Gly Xaa$^{31}$ Ser Ser-Z$_2$ (SEQ ID NO: 14), Gly Gly Xaa$^{31}$ Ser Ser Gly-Z$_2$ (SEQ ID NO: 15), Gly Gly Xaa$^{31}$ Ser Ser Gly Ala-Z$_2$ (SEQ ID NO: 16), Gly Gly Xaa$^{31}$ Ser Ser Gly Ala Xaa$^{36}$-Z$_2$ (SEQ ID NO: 17), Gly Gly Xaa$^{31}$ Ser Ser Gly Ala Xaa$^{36}$ Xaa$^{37}$-Z$_2$ (SEQ ID NO: 18) or Gly Gly Xaa$^{31}$ Ser Ser Gly Ala Xaa$^{36}$ Xaa$^{37}$ Xaa$^{38}$-Z$_2$ (SEQ ID NO: 19), wherein Xaa$^{31}$, Xaa$^{36}$, Xaa$^{37}$ and Xaa$^{38}$ are independently Pro, homoproline, 3Hyp, 4Hyp, thioproline, N-alkylglycine, N-alkylpentylglycine or N-alkylalanine, and Z$_2$ is —OH or —NH$_2$;

In certain embodiments contemplating compounds with structure of Formula II, exemplary N-alkyl groups for N-alkylglycine, N-alkylpentylglycine and N-alkylalanine include lower alkyl groups of 1 to about 6 carbon atoms, and in certain embodiments, of 1 to 4 carbon atoms.

In certain embodiments contemplating compounds with structure of Formula II, exemplary exendin agonist compounds include those wherein Xaa$^1$ is His or Tyr. In certain embodiments, exemplary compounds are those compounds wherein Xaa$^2$ is Gly. In certain embodiments, exemplary compounds are those compounds wherein Xaa$^{14}$ is Leu, pentylglycine or Met. In certain embodiments, exemplary compounds are those compounds wherein Xaa$^{25}$ is Trp or Phe. In certain embodiments, exemplary compounds are those compounds where Xaa$^6$ is Phe or naphthylalanine; Xaa$^{22}$ is Phe or naphthylalanine and Xaa$^{23}$ is Ile or Val.

In certain embodiments contemplating compounds with structure of Formula II, exemplary compounds are compounds wherein $Xaa^{31}$, $Xaa^{36}$, $Xaa^{37}$ and $Xaa^{38}$ are independently selected from Pro, homoproline, thioproline and N-alkylalanine.

In certain embodiments contemplating compounds with structure of Formula II, $Z_2$ is —$NH_2$.

In certain embodiments, compounds of Formula II are provided wherein $Xaa^1$ is His or Tyr; $Xaa^2$ is Gly; $Xaa^6$ is Phe or naphthylalanine; $Xaa^{14}$ is Leu, pentylglycine or Met; $Xaa^{22}$ is Phe or naphthylalanine; $Xaa^{23}$ is Ile or Val; $Xaa^{31}$, $Xaa^{36}$, $Xaa^{37}$ and $Xaa^{38}$ are independently selected from Pro, homoproline, thioproline or N-alkylalanine.

In certain embodiments, compounds include those of Formula II wherein $Xaa^1$ is His or Arg; $Xaa^2$ is Gly or Ala; $Xaa^3$ is Ala, Asp or Glu; $Xaa^5$ is Ala or Thr; $Xaa^6$ is Ala, Phe or naphthylalanine; $Xaa^7$ is Thr or Ser; $Xaa^8$ is Ala, Ser or Thr; $Xaa^9$ is Asp or Glu; $Xaa^{10}$ is Ala, Leu or pentylglycine; $Xaa^{11}$ is Ala or Ser; $Xaa^{12}$ is Ala or Lys; $Xaa^{13}$ is Ala or Gln; $Xaa^{14}$ is Ala, Leu or pentylglycine; $Xaa^{15}$ is Ala or Glu; $Xaa^{16}$ is Ala or Glu; $Xaa^{17}$ is Ala or Glu; $Xaa^{19}$ is Ala or Val; $Xaa^{20}$ is Ala or Arg; $Xaa^{21}$ is Ala or Leu; $Xaa^{22}$ is Phe or naphthylalanine; $Xaa^{23}$ is Ile, Val or tert-butylglycine; $Xaa^{24}$ is Ala, Glu or Asp; $Xaa^{25}$ is Ala, Trp or Phe; $Xaa^{26}$ is Ala or Leu; $Xaa^{27}$ is Ala or Lys; $Xaa^{28}$ is Ala or Asn; $Z_1$ is —OH, —$NH_2$, Gly-$Z_2$, Gly Gly-$Z_2$, Gly Gly $Xaa^{31}$—$Z_2$, Gly Gly $Xaa^{31}$ Ser-$Z_2$, Gly Gly $Xaa^{31}$ Ser Ser-$Z_2$ (SEQ ID NO: 20), Gly Gly $Xaa^{31}$ Ser Ser Gly-$Z_2$ (SEQ ID NO: 21), Gly Gly $Xaa^{31}$ Ser Ser Gly Ala-$Z_2$ (SEQ ID NO: 22), Gly Gly $Xaa^{31}$ Ser Ser Gly Ala $Xaa^{36}$-$Z_2$ (SEQ ID NO: 23), Gly Gly $Xaa^{31}$ Ser Ser Gly Ala $Xaa^{36}$ $Xaa^{37}$-$Z_2$ (SEQ ID NO: 24), Gly Gly $Xaa^{31}$ Ser Ser Gly Ala $Xaa^{36}$ $Xaa^{37}$ $Xaa^{38}$-$Z_2$ (SEQ ID NO: 25); $Xaa^{31}$, $Xaa^{36}$, $Xaa^{37}$ and $Xaa^{38}$ being independently Pro homoproline, thioproline or N-methylalanine; and $Z_2$ is —OH or —$NH_2$; provided that no more than three of $Xaa^3$, $Xaa^5$, $Xaa^6$, $Xaa^8$, $Xaa^{10}$, $Xaa^{11}$, $Xaa^{12}$, $Xaa^{13}$, $Xaa^{14}$, $Xaa^{15}$, $Xaa^{16}$, $Xaa^{17}$, $Xaa^{19}$, $Xaa^{20}$, $Xaa^{21}$, $Xaa^{24}$, $Xaa^{25}$, $Xaa^{26}$, $Xaa^{27}$ and $Xaa^{28}$ are Ala.

In certain embodiments contemplating compounds with structure of Formula II, exemplary compounds include those compounds where $Xaa^{14}$ is Leu, Ile, Val or pentylglycine, and $Xaa^{25}$ is Phe, Tyr or naphthylalanine.

In certain embodiments, exendin agonist compounds contemplated in the practice of the methods described herein comprise or include those described in Published Application WO99/25728, filed Nov. 13, 1998, entitled, "Novel Exendin Agonist Compounds," which claims the benefit of U.S. Provisional Application No. 60/066,029, filed Nov. 14, 1997, and corresponding U.S. Pat. No. 7,220,721 issued May 22, 2007, each of which are herein incorporated by reference in their entireties, and for all purposes, which purposes include the exendin and exendin agonist compounds and formulations thereof taught therein. Included are compounds comprising the structure of Formula III (SEQ ID NO: 26):

```
Xaa¹ Xaa² Xaa³ Xaa⁴ Xaa⁵ Xaa⁶ Xaa⁷ Xaa⁸ Xaa⁹          III

Xaa¹⁰ Xaa¹¹ Xaa¹² Xaa¹³ Xaa¹⁴ Xaa¹⁵ Xaa¹⁶ Xaa¹⁷

Ala Xaa¹⁹ Xaa²⁰ Xaa²¹ Xaa²² Xaa²³ Xaa²⁴ Xaa²⁵

Xaa²⁶ Xaa²⁷ Xaa²⁸-Z₁;
``` wherein $Xaa^1$ is His, Arg, Tyr, Ala, Norval, Val or Norleu; $Xaa^2$ is Ser, Gly, Ala or Thr; $Xaa^3$ is Ala, Asp or Glu; $Xaa^4$ is Ala, Norval, Val, Norleu or Gly; $Xaa^5$ is Ala or Thr; $Xaa^6$ is Phe, Tyr or naphthylalanine; $Xaa^7$ is Thr or Ser; $Xaa^8$ is Ala, Ser or Thr; $Xaa^9$ is Ala, Norval, Val, Norleu, Asp or Glu; $Xaa^{10}$ is Ala, Leu, Ile, Val, pentylglycine or Met; $Xaa^{11}$ is Ala or Ser; $Xaa^{12}$ is Ala or Lys; $Xaa^{13}$ is Ala or Gln; $Xaa^{14}$ is Ala, Leu, Ile, pentylglycine, Val or Met; $Xaa^{15}$ is Ala or Glu; $Xaa^{16}$ is Ala or Glu; $Xaa^{17}$ is Ala or Glu; $Xaa^{19}$ is Ala or Val; $Xaa''$ is Ala or Arg; $Xaa^{21}$ is Ala or Leu; $Xaa^{22}$ is Phe, Tyr or naphthylalanine; $Xaa^{23}$ is Ile, Val, Leu, pentylglycine, tert-butylglycine or Met; $Xaa^{24}$ is Ala, Glu or Asp; $Xaa^{25}$ is Ala, Trp, Phe, Tyr or naphthylalanine; $Xaa^{26}$ is Ala or Leu; $Xaa^{27}$ is Ala or Lys; $Xaa^{28}$ is Ala or Asn; $Z_1$ is absent or —OH, —$NH_2$, Gly-$Z_2$, Gly Gly-$Z_2$, Gly Gly $Xaa^{31}$-$Z_2$, Gly Gly $Xaa^{31}$ Ser-$Z_2$, Gly Gly $Xaa^{31}$ Ser Ser-$Z_2$ (SEQ ID NO: 14), Gly Gly $Xaa^{31}$ Ser Ser Gly-$Z_2$ (SEQ ID NO: 15), Gly Gly $Xaa^{31}$ Ser Ser Gly Ala-$Z_2$ (SEQ ID NO: 16), Gly Gly $Xaa^{31}$ Ser Ser Gly Ala $Xaa^{36}$-$Z_2$ (SEQ ID NO: 17), Gly Gly $Xaa^{31}$ Ser Ser Gly Ala $Xaa^{36}$ $Xaa^{37}$-$Z_2$ (SEQ ID NO: 18), Gly Gly $Xaa^{31}$ Ser Ser Gly Ala $Xaa^{36}$ $Xaa^{37}$ $Xaa^{38}$-$Z_2$ (SEQ ID NO: 19) or Gly Gly $Xaa^{31}$ Ser Ser Gly Ala $Xaa^{36}$ $Xaa^{37}$ $Xaa^{38}$ $Xaa^{39}$-$Z_2$ (SEQ ID NO: 27), wherein $Xaa^{31}$, $Xaa^{36}$, $Xaa^{37}$ and $Xaa^{38}$ are independently Pro, homoproline, 3Hyp, 4Hyp, thioproline, N-alkylglycine, N-alkylpentylglycine or N-alkylalanine, and $Z_2$ is —OH or —$NH_2$;

In certain embodiments, an exendin agonist for use as described herein is an exendin analog. As used herein, an "analog" refers to a peptide whose sequence was derived from that of a base reference peptide, e.g., an exendin such as exendin-3 or exendin-4, or a GLP-1 receptor agonist, and includes insertions, substitutions, extensions, and/or deletions of the reference amino acid sequence. In certain embodiments, analogs have at least 50% amino acid sequence identity with the base peptide. In other embodiments, analogs have at least 60%, 70%, 80%, 90%, or 95% amino acid sequence identity with the base peptide. In other embodiments, analogs comprise not more than 20, not more that 15, not more than 10, not more than 5 or not more than 3 amino acids insertions, substitutions, extensions and/or deletions. Such analogs may comprise conservative or non-conservative amino acid substitutions including but limited to non-natural amino acids and L and D stereoisomeric forms.

As used herein, identity or sequence identity means the degree of sequence relatedness between polypeptide or polynucleotide sequences, as determined by the match between strings of such sequences. Identity can be readily calculated by known methods including, but not limited to, those described in *Computational Molecular Biology, Lesk*, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073(1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387(1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76-80(1994); Birren, et al., *Genome Analysis*, 1: 543-559(1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215: 403-410(1990)).

In certain embodiments, the well-known Smith Waterman algorithm is used to determine identity. The choice of parameter values for matches, mismatches, and insertions or deletions is discretionary, although some parameter values have been found to yield more biologically realistic results than others. In one embodiment, the set of parameter values used for the Smith-Waterman algorithm is set forth in the "maximum similarity segments" approach, which uses values of 1 for a matched residue and −⅓ for a mismatched residue (a residue being either a single nucleotide or single amino acid). Waterman, *Bull. Math. Biol.* 46; 473(1984). Insertions and deletions (indels), x, are weighted as $x_k=1+\frac{1}{3}k$, where k is the number of residues in a given insert or deletion. Id.

The peptide or analog can be modified to further improve its agonist activity or other desirable property such as duration of action. Such modifications include, but are not limited to, derivatizations including phosphorylation, glycosylation, crosslinking, acylation, alkylation, proteolytic cleavage, linkage to an antibody molecule, membrane molecule or other ligand. The modified peptide or analog can be carboxy-terminal amidated or provided in its free carboxy-terminal hydroxy form.

The peptide or analog can also be further derivatized by chemical alterations such as amidation, glycosylation, acylation, sulfation, phosphorylation, acetylation, and cyclization. Such chemical alterations can be obtained through chemical or biochemical methodologies, as well as through in-vivo processes, or any combination thereof. Derivatives of the peptide or analog disclosed herein can also include conjugation to one or more polymers or small molecule substituents. One type of polymer conjugation is linkage or attachment of polyamino acids (e.g., poly-his, poly-arg, poly-lys, poly-glu, etc.) and/or fatty acid chains of various lengths to the N- or C-terminus or amino acid residue side chains of the peptide or analog. Small molecule substituents include short alkyls and constrained alkyls (e.g., branched, cyclic, fused, adamantyl), and aromatic groups.

In one embodiment, the peptide or analog thereof can be coupled to polyethylene glycol (PEG) by one of several strategies. Those skilled in the art will be able to utilize well-known techniques for linking one or more PEG polymers to the peptide or analog, described herein. Suitable PEG polymers typically are commercially available or can be made by techniques well know to those skilled in the art. In one embodiment, the polyethylene glycol polymers have molecular weights between 500 and 20,000 and can be branched or straight chain polymers. In other embodiments, the peptide or analog thereof are modified by the addition of polyamide chains of precise lengths as described, for example, in U.S. Pat. No. 6,552,167, the content of which is incorporated by reference in its entirety and for all purposes. In other embodiments, the peptide or analog thereof are modified by the addition of alkyl-PEG moieties as described in U.S. Pat. Nos. 5,359,030 and 5,681,811, the contents of which are incorporated by reference in their entirety and for all purposes.

An attachment of a PEG on an intact peptide or protein can be accomplished by coupling to amino, carboxyl or thiol groups. Such groups will typically be the N and C termini and on the side chains of such naturally occurring amino acids as lysine, aspartic acid, glutamic acid and cysteine. Since the compounds described herein can be prepared by solid phase peptide chemistry techniques, a variety of moieties containing diamino and dicarboxylic groups with orthogonal protecting groups can be introduced for conjugation to PEG.

The peptide or analog thereof can be linked to one or more macromolecules other than polyethylene glycol. Examples of such macromolecules include albumin, gelatin and antibodies. When the macromolecule is an antibody it can be a single chain antibody, an intact antibody, e.g. a catalytic antibody at the antibody's catalytic site via an appropriate hapten linker, or a fragment of an antibody, such as an Fc or Fab fragment. Further examples are described herein.

GLP-1 Receptor Agonist Compounds

Some embodiments useful in the practice of the methods described herein contemplate exendin, exendin agonists and GLP-1 receptor agonists linked to a protraction protein. Accordingly, in some embodiments, exendin, exendin agonists and GLP-1 receptor agonist compounds contemplated herein include without limitation those described in Published Application WO 2005/058958, entitled "Novel GLP-1 Analogues Linked to Albumin-Like Agents," and in U.S. application Ser. No. 11/454,348 (U.S. Publication No. US 2007/0093417), filed Jun. 16, 2006, both of which applications are herein incorporated by reference in their entireties and for all purposes, which purposes include the drug compounds are linked to a protraction protein and formulations thereof taught therein. Useful compounds in the context of linked protraction proteins include compounds with structure of Formula IV GLP-1 agonist-L-RR-protraction protein            IV wherein "GLP-1 agonist" is a polypeptide which is an agonist of the human GLP-1 receptor as known in the art or as described herein, "L" is a linker connecting an amino acid side chain of the GLP-1 agonist or the C-terminal amino acid residue of the GLP-1 agonist with RR, "RR" is the remains of a reactive residue that has formed a covalent bond with an amino acid residue of the protraction protein, and the "protraction protein" is a protein having a molar weight of at least 5 kDa and having a plasma half-life of at least 24 hours in human plasma. In some embodiments, the protraction protein is synthesized by a non-mammalian organism. In some embodiments, the protraction protein is prepared synthetically.

In certain embodiments related to compounds with structure of Formula IV, the protraction protein is recombinant human serum albumin (HSA) (SEQ ID NO: 4). In certain embodiments, the protraction protein is an HSA variant. In certain embodiments, the HSA variant has at least 80%, 90%, 95%, 96%, 97%, 98%, or even 99% amino acid sequence identity with respect to HSA. In certain embodiments, the HSA variant has reduced binding affinities towards copper and nickel as compared to the corresponding binding affinities of HSA towards copper and nickel. In certain embodiments, the protraction protein is an N-terminal fragment of HSA, or an analogue thereof. In certain embodiments, the protraction protein is a HSA variant comprising a modification of the Asp-Ala-His-Lys (SEQ ID NO: 28) N-terminal sequence. In certain embodiments, the protraction protein comprises at least one deletion among the three N-terminal amino acid residues Asp-Ala-His. In certain embodiments, the protraction protein comprises an N-terminal extension, for example without limitation, Glu$^{-3}$ Ala$^{-2}$ Glu$^{-1}$ Phe$^{0}$-HSA (1-585) or an N-terminal fragment thereof. In certain embodiments, the HSA variant is selected from the group consisting of HSA(2-585), HSA(3-585), HSA(4-585), Asp-Ala-HSA (4-585), Xaa$^{3}$-HSA(1-585) where Xaa$^{3}$ is an amino acid residue which has substituted the His residue occupying position 3 in HSA, and N-terminal fragments thereof. In certain embodiments, the protraction protein comprises an amino acid sequence of from 60-200 amino acid residues, the amino acid sequence being identical to a fragment of HSA or a fragment of HSA with one or more (e.g., 1, 2, 3, 4, 5 or even more) amino acid substitutions and/or deletions.

In further embodiments contemplating compounds with structure of Formula IV, the protraction protein is the Fc portion of an immunoglobulin, an analogue or a fragment thereof. In certain embodiments, the GLP-1 agonist has at least 50% amino acid identity with either GLP-1(7-37) or Exendin-4(1-39). In certain embodiments, the GLP-1 agonist has at least 80%, at least 85%, at least 90%, at least 95%, or even 100% amino acid identity with either GLP-1(7-37) or Exendin-4(1-39).

In certain embodiments contemplating compounds with structure of Formula IV, the GLP-1 agonist comprises the amino acid sequence of Formula V (SEQ ID NO: 29):

Xaa$^7$-Xaa$^8$-Glu-Gly-Thr-Phe-Thr-Ser-Asp-Xaa$^{16}$-Ser-   V

Xaa$^{18}$-Xaa$^{19}$-Xaa$^{20}$-Glu-Xaa$^{22}$-Xaa$^{23}$-Ala-Xaa$^{25}$-

Xaa$^{26}$-Xaa$^{27}$-Phe-Ile-Xaa$^{30}$-Trp-Leu-Xaa$^{33}$-Xaa$^{34}$-

Xaa$^{35}$-Xaa$^{36}$-Xaa$^{37}$-Xaa$^{38}$-Xaa$^{39}$-Xaa$^{40}$-Xaa$^{41}$-Xaa$^{42}$-

Xaa$^{43}$-Xaa$^{44}$-Xaa$^{45}$-Xaa$^{46}$ wherein Xaa$^7$ is L-histidine, D-histidine, desamino-histidine, 2-amino-histidine, □-hydroxy-histidine, homohistidine, N□-acetyl-histidine, □-fluoromethyl-histidine, □-methyl-histidine, 3-pyridylalanine, 2-pyridylalanine or 4-pyridylalanine; Xaa$^8$ is Ala, D-Ala, Gly, Val, Leu, Ile, Lys, Aib, (1-aminocyclopropyl)carboxylic acid, (1-aminocyclobutyl) carboxylic acid, 1-aminocyclopentyl)carboxylic acid, (1-aminocyclohexyl)carboxylic acid, (1-aminocycloheptyl) carboxylic acid, or (1-aminocyclooctyl)carboxylic acid; Xaa$^{16}$ is Val or Leu; Xaa$^{18}$ is Ser, Lys or Arg; Xaa$^{19}$ is Tyr or Gln; Xaa$^{20}$ is Leu or Met; Xaa$^{22}$ is Gly, Glu or Aib; Xaa$^{23}$ is Gln, Glu, Lys or Arg; Xaa$^{25}$ is Ala or Val; Xaa$^{26}$ is Lys, Glu or Arg; Xaa$^{27}$ is Glu or Leu; Xaa$^{30}$ is Ala, Glu or Arg; Xaa$^{33}$ is Val or Lys; Xaa$^{34}$ is Lys, Glu, Asn or Arg; Xaa$^{35}$ is Gly or Aib; Xaa$^{36}$ is Arg, Gly or Lys; Xaa$^{37}$ is Gly, Ala, Glu, Pro, Lys, amide or is absent; Xaa$^{38}$ is Lys, Ser, amide or is absent. Xaa$^{39}$ is Ser, Lys, amide or is absent; Xaa$^{40}$ is Gly, amide or is absent; Xaa$^{41}$ is Ala, amide or is absent; Xaa$^{42}$ is Pro, amide or is absent; Xaa$^{43}$ is Pro, amide or is absent; Xaa$^{44}$ Pro, amide or is absent; Xaa$^{45}$ is Ser, amide or is absent; Xaa$^{46}$ is amide or is absent; provided that if Xaa$^{38}$, Xaa$^{39}$, Xaa$^{40}$, Xaa$^{41}$, Xaa$^{42}$, Xaa$^{43}$, Xaa$^{44}$, Xaa$^{45}$ or Xaa$^{46}$ is absent then each amino acid residue downstream is also absent.

In certain embodiments, in compounds with structure of Formula IV, the GLP-1 agonist is protected against DPP-IV by substitutions known in the art. In certain embodiments, the GLP-1 agonist is substituted at position 8. In certain embodiments, the GLP-1 agonist comprises an Aib residue (aminoisobutyric acid) at position 8. In certain embodiments, the amino acid residue in position 7 of the GLP-1 peptide (e.g., the N-terminal of GLP-1(7-37)) is selected from the group consisting of D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine and 4-pyridylalanine. In certain embodiments, the GLP-1 agonist comprises no more than 12, no more than 6, no more than 4, or no more than 2 amino acid residues which have been exchanged, added or deleted as compared to GLP-1(7-37) or Exendin-4(1-39). In certain embodiments, the GLP-1 agonist comprises no more than 4 amino acid residues which are not encoded by the genetic code.

In further embodiments contemplating compounds with structure of Formula IV, the GLP-1 agonist is selected from the group consisting of [Arg$^{34}$]GLP-1(7-37), [Arg$^{26,34}$]GLP-1(7-37)Lys, [Lys$^{36}$Arg$^{26,34}$]GLP-1(7-36), [Aib$^{8,22,35}$]GLP-1 (7-37), [Aib$^{8,35}$]GLP-1(7-37), [Aib$^{8,22}$]GLP-1(7-37), [Aib$^{8,22,35}$Arg$^{26,34}$]GLP-1(7-37)Lys, [Aib$^{8,35}$Arg$^{26,34}$]GLP-1(7-37)Lys, [Aib$^{8,22}$Arg$^{26,34}$]GLP-1(7-37)Lys, [Aib$^{8,22,35}$Arg$^{26,34}$]GLP-1(7-37)Lys, [Aib$^{8,35}$Arg$^{26,34}$]GLP-1(7-37) Lys, [Aib$^{8,22,35}$Arg$^{26}$]GLP-1(7-37)Lys, [Aib$^{8,35}$Arg$^{26}$]GLP-1(7-37)Lys, [Aib$^{8,22}$Arg$^{26}$]GLP-1(7-37)Lys, [Aib$^{8,22,35}$Arg$^{34}$]GLP-1(7-37)Lys, [Aib$^{8,35}$Arg$^{34}$]GLP-1(7-37)Lys, [Aib$^{8,22}$Arg$^{34}$]GLP-1(7-37)Lys, [Aib$^{8,22,35}$Ala$^{37}$]GLP-1(7-37)Lys, [Aib$^{8,35}$Ala$^{37}$]GLP-1(7-37)Lys, [Aib$^{8,22}$Ala$^{37}$]GLP-1(7-37)Lys, [Aib$^{8,22,35}$Ala$^{37}$]GLP-1(7-37)Lys, [Aib$^{8,35}$Lys$^{37}$]GLP-1(7-37) and [Aib$^{8,22}$Lys$^{37}$]GLP-1(7-37). In certain embodiments, the GLP-1 agonist is exendin-4(1-39). In certain embodiments, the GLP-1 agonist is ZP-10 with structure [Ser$^{38}$Lys$^{39}$]Exendin-4(1-39)LysLysLysLysLys-amide (poly-Lys disclosed as SEQ ID NO: 30).

In further embodiments contemplating compounds with structure of Formula IV, the GLP-1 agonist is attached to the moiety "-L-RR-protraction protein" via the side chain of the amino acid residue in position 23, 26, 34, 36 or 38 (i.e., relative to GLP-1(7-37)), corresponding to position 17, 20, 28, 30 or 32 relative to Exendin-4(1-39). In further embodiments, the GLP-1 agonist is attached to the moiety "-L-RR-protraction protein" via the side chain of the C-terminal amino acid residue. In further embodiments, the GLP-1 agonist is attached to the moiety "-L-RR-protraction protein" via the side chain of an amino acid residue selected from arginine, lysine, cysteine, glutamic acid, aspartic acid, histidine, serine, threonine and tyrosine.

In further embodiments contemplating compounds with structure of Formula IV, the linker L is selected from the group consisting of the bivalent connecting chemical groups amide, amine, thioethers, ethers, urethanes, carbamates, hydrazines, oximes, oxazolidines or thiazolidines.

Exemplary compounds with structure of Formula IV contemplated by the methods described herein include, without limitation, GLP-1 agonist —C(═O)CH$_2$O(CH$_2$)$_2$O(CH$_2$)$_2$—RR-protraction protein, GLP-1 agonist —C(═O)(CH$_2$)$_n$(OCH$_2$CH$_2$)$_m$—RR-protraction protein, GLP-1 agonist —S(═O)$_2$(CH$_2$)$_n$(OCH$_2$CH$_2$)$_m$—RR-protraction protein, GLP-1 agonist —CH$_2$(CH$_2$)$_n$(OCH$_2$CH$_2$)$_m$—RR-protraction protein, GLP-1 agonist —C(═O)O(CH$_2$)$_n$(OCH$_2$CH$_2$)$_m$—RR-protraction protein, wherein n is an integer in the range from 0 to 10, and m is an integer in the range from 0 to 100.

Further exemplary compounds with structure of Formula IV contemplated by the methods described herein include, without limitation, GLP-1 agonist-L-NC(═O)CH$_2$— sulphur in cysteine residue in protraction protein, GLP-1 agonist-L-S(═O)$_2$(CH$_2$)$_2$— sulphur in cysteine residue in protraction protein, GLP-1 agonist-L-NC(═O)CH$_2$— sulphur in cysteine residue in protraction protein, and GLP-1 agonist-L-RR'-sulphur in cysteine residue in protraction protein, wherein RR' is 2,5-dioxo-pyrrolidine-1,3-diyl.

Further exemplary compounds with structure of Formula IV contemplated herein include, without limitation, S-γ$^{34}$-(1-{2-[2-(2-([Lys$^{32}$]-exendin-(1-39)amide-N-ε$^{32}$-yl)acetyloxyethoxy)ethylcarbamoyl]ethyl}-2,5-dioxo-pyrrolidin-3-yl)

Albumin, wherein Albumin is recombinant Albagen (New Century Pharma, recombinant HSA(2-585)); S-γ³⁴-(1-{2-[2-(2-([Lys²⁰]-exendin-(1-39)amide-N-ε-²⁰-yl)acetyloxy-ethoxy)ethylcarbamoyl]ethyl}-2,5-dioxo-pyrrolidin-3-yl) Albumin, wherein Albumin is recombinant Albagen; S-γ³⁴-(1-{2-[2-(2-([Arg¹²,Lys²⁷]-exendin-(1-39)amide-N-ε²⁷-yl)acetyloxyethoxy)ethylcarbamoyl]ethyl}-2,5-dioxo-pyrroli-din-3-yl) Albumin, wherein Albumin is recombinant Albagen; and S-γ³⁴-(1-{2-[2-(2-([Arg¹²,²⁷,Lys³²]-exendin-(1-39)amide-N-ε³²-yl)acetyloxyethoxy)ethylcarbamoyl] ethyl}-2,5-dioxo-pyrrolidin-3-yl) Albumin, wherein Albumin is recombinant Albagen.

Some embodiments of the methods described herein contemplate exendins, exendin agonists, and GLP-1 receptor agonists linked to a protracting tag. Accordingly, in some embodiments, compounds contemplated herein include without limitation those described in Published Application WO 2007/068718, entitled "Polypeptide Protracting Tags," filed Dec. 13, 2006, which application is herein incorporated by reference in its entirety and for all purposes, which purposes include the protracting tags, and the exendins, exendin agonists, and GLP-1 receptor agonists linked to protracting tags and formulations thereof taught therein. The protracting tags taght therein can be used with any of the exendin, exendin agonists or GLP-1 receptor agonists described herein. Useful compounds in this context include compounds with structure of Formula VI

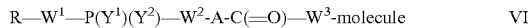

wherein A represents —(CH₂)₁₋₂₀— in which one or more methylene groups are optionally replaced by a diradical selected from the group consisting of —O—, —S—, —NH— and —CH=CH— and which is optionally substituted with one or more substituent(s) selected from the group consisting of C₁₋₆-alkyl, C₁₋₆-alkoxy or carboxy; R represents C₁₋₂₀-alkyl- in which one or more methylene groups are optionally replaced by a diradical selected from the group consisting of —O—, —S—, —NH— and —CH=CH— and which is optionally substituted with one or more substituent(s) selected from the group consisting of aryl, haloaryl, cyanoaryl, heteroaryl, C₃₋₁₀-cycloalkyl, aryl-C₃₋₁₀-cycloalkyl, diaryl-C₃₋₁₀-cycloalkyl, carboxyl, 5-tetrazolyl, acylaminosulfonyl, sulfonylaminocarbonyl, and a straight or branched C₁₋₆-alkyl; or C₃₋₁₀-cycloalkyl- optionally substituted with one or more substituent(s) selected from the group consisting of aryl, haloaryl, cyanoaryl, heteroaryl, C₃₋₁₀-cycloalkyl, carboxyl, 5-tetrazolyl, acylaminosulfonyl, sulfonylaminocarbonyl, and a straight or branched C₁₋₆-alkyl; W¹ and W² independently are —O—, —CH₂— or —S—; Y¹ is —OH or —SH; Y² is =O or =S; W³ is a bond or a spacer; and the term "molecule" represents a fragment obtained by formal abstraction of a hydrogen atom from an amino group, a hydroxy group, or a mercapto group of an exendin, exendin agonist, or GLP-1 receptor agonist; with the proviso that at least either A represents —(CH₂)₁₁₋₂₀— in which one or more methylene groups are optionally replaced by a diradical selected from the group consisting of —O—, —S—, —NH— and —CH=CH— and which is optionally substituted with one or more substituent(s) selected from the group consisting of C₁₋₆-alkyl, C₁₋₆-alkoxy or carboxy, or R represents C₁₁₋₂₀-alkyl- in which one or more methylene groups are optionally replaced by a diradical selected from the group consisting of —O—, —S—, —NH— and —CH=CH— and which is optionally substituted with one or more substituent(s) selected from the group consisting of aryl, haloaryl, cyanoaryl, heteroaryl, C₃₋₁₀-cycloalkyl, aryl-C₃₋₄₀-cycloalkyl, diaryl-C₃₋₁₀-cycloalkyl, carboxyl, 5-tetrazolyl, acylaminosulfonyl, sulfonylaminocarbonyl, and a straight or branched C₁₋₆-alkyl.

In certain embodiments contemplating compounds with structure of Formula VI, spacer W³ is selected from the group consisting of oligo(ethylene glycol), an amino acid or a combination thereof.

In certain embodiments contemplating compounds with structure of Formula VI, the molecule comprises the amino acid sequence with structure of Formula VII (SEQ ID NO: 31):

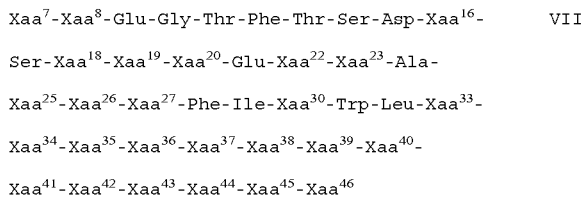

wherein Xaa⁷ is L-histidine, D-histidine, desamino-histidine, 2-amino-3-(2-aminoimidazol-4-yl)propionic acid, □-hydroxy-histidine, homohistidine, Nᵋ-acetyl-histidine, □-fluoromethyl-histidine, □-methyl-histidine, 3-pyridylalanine, 2-pyridylalanine or 4-pyridylalanine; Xaa⁸ is Ala, Gly, Val, Leu, Ile, Lys, Aib, 1-aminocyclopropanecarboxylic acid, 1-aminocyclobutanecarboxylic acid, 1-aminocyclopentanecarboxylic acid, 1-aminocyclohexanecarboxylic acid, 1-aminocycloheptanecarboxylic acid, or 1-aminocyclooctanecarboxylic acid; Xaa¹⁶ is Val or Leu; Xaa¹⁸ is Ser, Lys or Arg; Xaa¹⁹ is Tyr or Gln; Xaa²⁰ is Leu or Met; Xaa²² is Gly, Glu or Aib; Xaa²³ is Gln, Glu, Lys or Arg; Xaa²⁵ is Ala or Val; Xaa²⁶ is Lys, Glu or Arg; Xaa²⁷ is Glu or Leu; Xaa³⁰ is Ala, Glu or Arg; Xaa³³ is Val or Lys; Xaa³⁴ is Lys, Glu, Asn or Arg; Xaa³⁵ is Gly or Aib; Xaa³⁶ is Arg, Gly or Lys; Xaa³⁷ is Gly, Ala, Glu, Pro, Lys, amide or is absent; Xaa³⁸ is Lys, Ser, amide or is absent; Xaa³⁹ is Ser, Lys, amide or is absent; Xaa⁴⁰ is Gly, amide or is absent; Xaa⁴¹ is Ala, amide or is absent; Xaa⁴² is Pro, amide or is absent; Xaa⁴³ is Pro, amide or is absent; Xaa⁴⁴ is Pro, amide or is absent; Xaa⁴⁵ is Ser, amide or is absent; Xaa⁴⁶ is amide or is absent; provided that if Xaa³⁸, Xaa³⁹, Xaa⁴⁰, Xaa⁴¹, Xaa⁴², Xaa⁴³, Xaa⁴⁴, Xaa⁴⁵ Xaa⁴⁶ is absent then each amino acid residue downstream is also absent.

In certain embodiments contemplating compounds with structure of Formula VI, the molecule is selected from GLP-1(7-35), GLP-1(7-36), GLP-1(7-36)-amide, GLP-1(7-37), GLP-1(7-38), GLP-1(7-39), GLP-1(7-40), GLP-1(7-41) or an analogue thereof. In certain embodiments, the molecule is selected from the group consisting of Arg³⁴GLP-1(7-37), Lys³⁸Arg²⁶,³⁴GLP-1(7-38), Lys³⁸Arg²⁶,³⁴GLP-1(7-38)-OH, Lys³⁶Arg²⁶,³⁴GLP-1(7-36), Aib⁸,²²,³⁵GLP-1(7-37), Aib⁸,³⁵GLP-1(7-37), Aib⁸,²²GLP-1(7-37), Aib⁸,²²,³⁵Arg²⁶,³⁴Lys³⁸GGP-1(7-38), Aib⁸,³⁵Arg²⁶,³⁴Lys³⁸GLP-1(7-38), Aib⁸,²² Arg²⁶,³⁴Lys³⁸GLP-1(7-38), Aib⁸,²²,³⁵Arg²⁶,³⁴jLys³⁸GLP-1(7-38), Aib⁸,³⁵Arg²⁶,³⁴Lys³⁸GLP-1(7-38), Aib⁸,²²,³⁵Arg²⁶Lys³⁸GLP-1(7-38), Aib⁸,³⁵Arg²⁶Lys³⁸GLP-1(7-38), Aib⁸,²²Arg²⁶Lys³⁸GLP-1(7-38), Aib⁸,²²,³⁵Arg³⁴Lys³⁸GLP-1(7-38), Aib⁸,³⁵Arg³⁴Lys³⁸GLP-1(7-38), Aib⁸,²²Arg³⁴Lys³⁸GLP-1(7-38), Aib⁸,²²,³⁵Ala³⁷Lys³⁸GLP-1(7-38), Aib⁸,³⁵Ala³⁷Lys³⁸GLP-1(7-38), Aib⁸,²²Ala³⁷Lys³⁸GLP-1(7-38), Aib⁸,²²,³⁵Lys³⁷GLP-1(7-37), Aib⁸,³⁵Lys³⁷GLP-1(7-37), and Aib⁸,²²Lys³⁷GLP-1(7-38).

Further exemplary compounds with structure of Formula VI include N-ε²⁶-((S)-4-[16-{(hydroxy)(octadecyloxy) phosphoryloxy}hexadecanoylamino]-4-carboxybutyryl)

[Aib⁸,Arg³⁴]GLP-1(7-37), N-ε²⁶-((S)-4-[16-{(hydroxy)(pentyloxy)phosphoryloxy}hexadecanoylamino]-4-carboxybutyryl)[Aib⁸, Arg³⁴]GLP-1(7-37), N-ε²⁶-((S)-4-[16-{(hydroxy)(dodecyloxy)phosphoryloxy}hexadecanoylamino]-4-carboxybutyryl) [Aib⁸, Arg³⁴]GLP-1(7-37), N-ε²⁶-((S)-4-[16-{(hydroxy)(methoxy)phosphoryl}nonadecanoylamino]-4-carboxybutyryl)[Aib⁸,Arg³⁴]GLP-1(7-37), and N-ε²⁶-(3-(2-{2-[2-(hexadecyloxy-hydroxy-phosphoryloxy)-ethoxy]-ethoxy}-ethoxy)-propionyl)-[Aib⁸,Arg³⁴]GLP-1(7-37).

Some embodiments of the methods described herein contemplate GLP-1 receptor agonist which are GLP-1 analogs having a modification of at least one non-proteogenic amino acid residues in positions 7 and/or 8 relative to GLP-1(7-37), and which GLP-1 receptor agonist is acylated with a moiety to the lysine residue in position 26, wherein the acylation moiety comprises at least two acidic groups, and wherein the acylation is optionally via a non-natural amino acid hydrophilic linker. Accordingly, in some embodiments, GLP-1 receptor agonist compounds contemplated in the practice of the methods described herein include without limitation those described in Published Application WO 2006/097537, filed Mar. 20, 2006, entitled "Acylated GLP-1 Compounds", which application is herein incorporated by reference in its entirety and for all purposes, which purposes include the GLP-1 receptor agonists and formulations thereof taught therein. Useful compounds for the methods described herein include GLP-1 analogs having non-proteogenic amino acid residues in positions 7 and/or 8 relative to GLP-1(7-37) which is acylated with a moiety to the lysine residue in position 26, and where said moiety comprises at least two acidic groups, wherein one such acidic group is attached terminally. In certain embodiments, the moiety attached at position 26 comprises a hydrophilic linker. In certain embodiments, the hydrophilic linker comprises at least five non-hydrogen atoms wherein 30-5-% are either N or O. In certain embodiments, the moiety attached at position 26 comprises an albumin binding moiety separated from the peptide by the hydrophilic linker. The term "albumin binding moiety" as used herein refers to a moiety which binds non-covalently to human serum albumin. In certain embodiments, the albumin binding moiety is a linear or branched lipophilic moiety containing 4-40 carbon atoms having a distal acid group.

In this context, exemplary GLP-1 receptor agonist compounds contemplated in the practice of the methods described herein include, without limitation, [Nε-(17-carboxy-heptadecanoyl)-Lys²⁶,Aib⁸,Arg³⁴]GLP-1-(7-37), [Nε-(19-carboxynonadecanoyl)-Lys²⁶,Aib⁸,Arg³⁴]GLP-1-(7-37), [Nε-(4-{[N-(2-carboxyethyl)-N-(15-carboxypentadecanoyl) amino]methyl}benzoyl)-Lys²⁶,Arg³⁴]GLP-1-(7-37), [Nε-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl]-Lys²⁶,Aib⁸,Arg³⁴]GLP-1-(7-37), [Nε-[2-(2-[2-(2-[2-(2-[4-(17-carboxynonadecanoylamino)-4(S)-carboxybutyrylamino]ethoxy)ethoxy]acetylamino) ethoxy]ethoxy)acetyl]-Lys²⁶,Aib⁸,Arg³⁴]GLP-1-(7-37), [Nε[2-(2-[2-(2-[2-(2-[4-(17-carboxyheptadecanoylamino)-4(S)-carboxybutyrylamino]ethoxy)ethoxy]acetylamino) ethoxy]ethoxy)acetyl]-Lys²⁶,3-(4-imidazolyl)propionyl⁷,Arg³⁴]GLP-1-(7-37), [Nε-[2-(2-[2-(2-[2-[4-(17-carboxyheptadecanoylamino)-(carboxymethyl-amino)acetylamino]ethoxy) ethoxy]acetylamino)ethoxy]ethoxy)acetyl]-Lys²⁶,Aib⁸,Arg³⁴]GLP-1-(7-37), [Nε-[2-(2-[2-(2-[2-(2-[4-(17-carboxyheptadecanoylamino)-3(S)-sulfopropionylamino]ethoxy)ethoxy]acetylamino) ethoxy]ethoxy)acetyl]-Lys²⁶,Aib⁸,Arg³⁴]GLP-1-(7-37), [Nε[2-(2-[2-(2-[2-(2-[4-(17-carboxyheptadecanoylamino)-4(S)-carboxybutyrylamino]ethoxy)ethoxy]acetylamino)ethoxy]ethoxy)acetyl]-Lys²⁶,Gly⁸,Arg³]GLP-1-(7-37), [Nε-[2-(2-[2-(2-[2-(2-[4-(17-carboxyheptadecanoylamino)-4(S)-carboxybutyrylamino]ethoxy)ethoxy]acetylamino) ethoxy]ethoxy)acetyl]-Lys²⁶,Aib⁸,Arg³⁴]GLP-1-(7-37)-amide, [Nε-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl]-Lys²⁶,Aib⁸,Arg³⁴,Pro³⁷]GLP-1-(7-37)amide, [Aib⁸, Nε-{2-(2-(2-(2-[2-(2-(4-(pentadecanoylamino)-4-carboxybutyrylamino)ethoxy)ethoxy]acetyl)ethoxy)ethoxy)acetyl}-Lys²⁶,Arg³⁴]GLP-1(7-37)-OH, [Nε-[2-(2-[2-(2-[2-(2-[4-{[N-(2-carboxyethyl)-N-(17-carboxyheptadecanoyl)amino]methyl}benzoyl)amino]ethoxy)ethoxy]acetylamino)ethoxy]ethoxy)acetyl]-Lys²⁶, Aib⁸,Arg³⁴]GLP-1(7-37), [N-α⁷-formyl, Nε-[2-(2-[2-(2-[2-(2-[4-(17-carboxyheptadecanoylamino)-4(S)-carboxybutyrylamino]ethoxy)ethoxy]acetylamino) ethoxy]ethoxy)acetyl]-Lys²⁶,Arg³⁴]GLP-1(7-37), Nε-[2-(2-[2-(2-[2-(2-[4-(17-carboxyheptadecanoylamino)-4(S)-carboxybutyrylamino]ethoxy)ethoxy]acetylamino) ethoxy]ethoxy)acetyl]-Lys²⁶,Aib⁸,Glu²²,Arg³⁴]GLP-1-(7-37), [Nε-{3-[2-(2-{2-[2-(2-{2-[2-(2-[4-(15-(N—((S)-1,3-dicarboxypropyl)carbamoyl)pentadecanoylamino)-(S)-4-carboxybutyrylamino]ethoxy)ethoxy]ethoxy}ethoxy) ethoxy]ethoxy}ethoxy)ethoxy]propionyl}-Lys²⁶,Aib⁸, Arg³⁴]GLP-1-(7-37), Nε-[2-(2-[2-(2-[2-(2-[4-{[N-(2-carboxyethyl)-N-(17-carboxyheptadecanoyl)amino]methyl}benzoyl)amino](4(S)-carboxybutyrylamino)ethoxy)ethoxy]acetylamino)ethoxy]ethoxy)acetyl]-Lys²⁶,Aib⁸, Arg³⁴]GLP-1(7-37), [Nε-{(S)-4-carboxy-4-((S)-4-carboxy-4-((S)-4-carboxy-4-(S)-4-carboxy-4-(19-carboxynonadecanoylamino)butyrylamino) butyrylamino) butyrylamino)butyrylamino}-Lys²⁶,Aib⁸,Arg³⁴]GLP-1-(7-37), [Nε-4-(17-carboxyheptadecanoylamino)-4(S)-carboxybutyryl-Lys²⁶,Aib⁸,Arg³⁴]GLP-1-(7-37), [Nε-{3-[2-(2-{2-[2-(2-{2-[2-(2-[4-(17-carboxyheptadecanoylamino)-4(S)-carboxybutyrylamino]ethoxy)ethoxy]ethoxy}ethoxy) ethoxy]ethoxy}ethoxy)ethoxy]propionyl}-Lys²⁶,Aib⁸, Arg³⁴]GLP-1-(7-37), [Nε-{2-(2-(2-(2-[2-(2-(4-(17-carboxyheptadecanoylamino)-4-carboxybutyrylamino)ethoxy)ethoxy]acetyl)ethoxy)ethoxy)acetyl)}-Lys²⁶, Aib⁸,²²,²⁷,³⁰,³⁵,Arg³⁴,Pro³⁷]GLP-1(7-37)amide, [Nε-[2-(2-[2-(2-[4-(21-carboxyuneicosanoylamino)-4(S)-carboxybutyrylamino]ethoxy]ethoxy)acetyl]-Lys²⁶,Aib⁸,Arg³⁴]GLP-1-(7-37), [Nε-[2-(2-[2-(2-[2-(2-[4-(21-carboxyuneicosanoylamino)-4(S)-carboxybutyrylamino]ethoxy)ethoxy]acetylamino)ethoxy]ethoxy)acetyl]-Lys²⁶, Aib⁸,Arg³⁴]GLP-1-(7-37), and [N-α¹-formyl-Nε-[2-(2-[2-(2-[2-(2-[4-(19-carboxynonadecanoylamino)-4(S)-carboxybutyrylamino]ethoxy)ethoxy]acetylamino)ethoxy]ethoxy)acetyl]-Lys²⁶,Arg³⁴]GLP-1-(7-37).

Some embodiments of the methods described herein contemplate exendin, exendin agonists or GLP-1 receptor agonist, particularly analogs of GLP-1 and exendin, acylated with a diacid, and further in which the drug compound is optionally stabilized against DPP-IV by modification of at least one amino acid residue in positions 7-8 (relative to GLP-1(7-37)). Accordingly, in some embodiments, exendin agonist or GLP-1 receptor agonist compounds contemplated in the practice of the methods described herein include without limitation those described in Published Application WO 2006/037810, filed Oct. 7, 2005, entitled "Protracted GLP-1 Compounds," which application is herein incorporated by reference in its entirety and for all purposes, which purposes include the GLP-1 receptor agonist compounds and formulations thereof taught therein. Useful compounds in this context include acylated GLP-1 receptor agonists which are stabilized against DPP-IV activity by modification of at least one amino acid residue in positions 7-8, and wherein acylation is afforded with a diacid attached directly to the C-terminal amino acid residue of the GLP-1 analog. In certain embodiments, the diacid is attached to the ε-amino group of a lysine residue of the GLP-1 receptor agonist. In certain embodiments, the GLP-1 receptor agonist has an extended C-terminal wherein the compound comprises an amino acid residue in position 38 relative to the sequence GLP-1(7-37). In certain embodiments, the diacid is attached to Lys$^{38}$. In certain embodiments, the diacid is a dicarboxylic acid. In certain embodiments, the acylation group is a straight-chain or branched alkane α,ω-dicarboxylic acid. In certain embodiments, the acylation group has a structure selected from HOOC—(CH$_2$)$_{14}$CO—, HOOC—(CH$_2$)$_{15}$CO—, HOOC—(CH$_2$)$_{16}$CO—, HOOC—(CH$_2$)$_{17}$CO—, and HOOC—(CH$_2$)$_{18}$CO—. In certain embodiments, the GLP-1 receptor agonist comprises a modification of the N-terminal L-histidine in position 7 of the GLP-1 (7-37) sequence. In certain embodiments, the GLP-1 receptor agonist comprises imidazopropionyl$^7$, α-hydroxy-histidine$^7$ or N-methyl-histidine$^7$, D-histidine$^7$, desamino-histidine$^7$, 2-amino-histidine$^7$, β-hydroxy-histidine$^7$, homohistidine$^7$, N$^α$-acetyl-histidine$^7$, α-fluoromethyl-histidine$^7$, α-methyl-histidine$^7$, 3-pyridylalanine$^7$, 2-pyridylalanine$^7$ or 4-pyridylalanine$^7$. In certain embodiments, the GLP-1 receptor agonist comprises a substitution of the L-alanine in position 8 of the GLP-1(7-37) for another amino acid. In certain embodiments, the GLP-1 receptor agonist comprises Aib$^8$, Gly$^8$, Val$^8$, Ile$^8$, Leu$^8$, Ser$^8$ or Thr$^8$. In certain embodiments, the GLP-1 receptor agonist comprises a substitution of the L-alanine in position 8 of the GLP-1(7-37) sequence for (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid. In certain embodiments, the GLP-1 receptor agonist comprises no more than 15, no more than 10, no more than 6, or no more than 4 amino acid residues which have been exchanged, added, or deleted as compared with GLP-1(7-37). In certain embodiments, the GLP-1 receptor agonist useful in the practice of the methods described herein comprises only one lysine residue.

Exemplary acylated GLP-1 receptor agonist compounds contemplated in the practice of the methods described herein include, without limitation, [Aib$^8$Arg$^{26,34}$]GLP-1(7-37)Lys (17-carboxyheptadecanoyl)-OH, [Gly$^8$,Arg$^{26,34,36}$]GLP-1(7-37)Lys(17-carboxyheptadecanoylamino)-OH, [α-hydroxydesamino-His$^7$,Gly$^8$,Arg$^{26,34}$]GLP-1(7-37)Lys(17-carboxyheptadecanoyl)-OH, [Gly$^8$,Glu$^{22,23,30}$,Arg$^{18,26,34}$]GLP1(7-37)Lys(17-carboxyheptadecanoyl)-NH$_2$, and [Gly$^8$, Arg$^{26,34}$]GLP-1(7-37)Lys (19-carboxynonadecanoyl)-OH.

Some embodiments of the methods described herein contemplate exendin agonist compounds wherein one amino acid has been exchanged by a lysine residue which lysine residue is acylated with a diacid. Accordingly, in some embodiments, exendin agonist compounds contemplated in the practice of the methods described herein include without limitation those described in Published Application WO 2006/037811, filed Oct. 7, 2005, entitled "Protracted Exendin-4 Compounds," which application is herein incorporated by reference in its entirety and for all purposes, which purposes include the exendin agonist compounds and formulations thereof taught therein. Useful exendin agonist compounds for the practice of the methods described herein include exendin-4 analogs wherein one amino acid has been exchanged by a lysine residue, which lysine residue is acylated with a diacid. In certain embodiments, the exendin-4 analog comprises an acylated lysine residue in position 20 or 32. In certain embodiments, the diacid is a dicarboxylic acid. In certain embodiments, the acylation group is a straight-chain or branched alkane ☐,☐-dicarboxylic acid. In certain embodiments, the acylation group has the structure HOOC—(CH$_2$)$_n$CO—, wherein n is 12 to 20. In certain embodiments, the acylation group has a structure selected from HOOC—(CH$_2$)$_{14}$CO—, HOOC—(CH$_2$)$_{15}$CO—, HOOC—(CH$_2$)$_{16}$CO—, HOOC—(CH$_2$)$_{17}$CO—, and HOOC—(CH$_2$)$_{18}$CO—. In certain embodiments, exendin agonist compounds useful in the practice of the methods described herein are acylated exendin-4 analogs comprising no more than 15, no more than 10, no more than 6, or no more than 4 amino acid residues which have been exchanged, added or deleted as compared to exendin-4(1-39) (SEQ ID NO: 2). In certain embodiments, the exendin agonist useful in the practice of the methods described herein comprises only one lysine residue.

In the context of protracted exendin-4 compounds, exemplary exendin agonist compounds contemplated in the practice of the methods described herein include, without limitation, [N$^ε$-(17-carboxyheptadecanoic acid)Lys$^{20}$]exendin-4 (1-39)amide, [N$^ε$-(17-carboxy-heptadecanoyl)Lys$^{32}$]exendin-4(1-39)amide, [Desamino-His$^1$,N$^ε$-(17-carboxyheptadecanoyl)Lys$^{20}$]exendin-4(1-39)amide, [Arg$^{12,27}$, NLe$^{14}$,N$^ε$-(17-carboxy-heptadecanoyl)Lys$^{32}$]exendin-4(1-39)amide, [N$^ε$-(19-carboxynonadecanoylamino)Lys$^{20}$]exendin-4(1-39)-amide, [N$^ε$-(15-carboxypentadecanoylamino)Lys$^{20}$]exendin-4(1-39)-amide, [N$^ε$-(13-carboxytridecanoylamino)Lys$^{20}$]exendin-4(1-39)-amide, and [N$^ε$-(11-carboxyundecanoylamino)Lys$^{20}$]exendin-4(1-39)-amide.

Some embodiments of the methods described herein contemplate amino acid functionalization with a lipophilic substituent. Accordingly, in certain embodiments, GLP-1 receptor agonist compounds contemplated for the practice of the methods described herein include without limitation those described in U.S. Pat. No. 6,569,832, filed Nov. 10, 2000, entitled "Inhibition of Beta Cell Degeneration," which claims the benefit of U.S. Provisional Application No. 60/166,800, filed Nov. 22, 1999, and U.S. Provisional Application No. 60/185,845, filed Feb. 29, 2000, all of which applications are herein incorporated by reference in their entireties and for all purposes, which purposes include peptides having lipophilic substitution and formulations thereof taught therein. In certain embodiments, compounds are contemplated with the structure of Formula VIII (SEQ ID NO: 32)

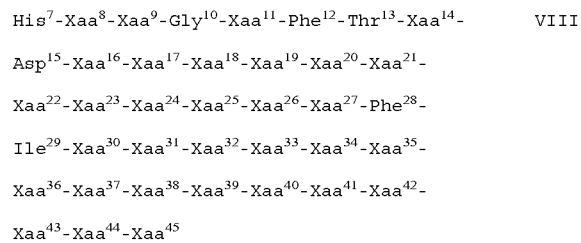

His$^7$-Xaa$^8$-Xaa$^9$-Gly$^{10}$-Xaa$^{11}$-Phe$^{12}$-Thr$^{13}$-Xaa$^{14}$- VIII

Asp$^{15}$-Xaa$^{16}$-Xaa$^{17}$-Xaa$^{18}$-Xaa$^{19}$-Xaa$^{20}$-Xaa$^{21}$-

Xaa$^{22}$-Xaa$^{23}$-Xaa$^{24}$-Xaa$^{25}$-Xaa$^{26}$-Xaa$^{27}$-Phe$^{28}$-

Ile$^{29}$-Xaa$^{30}$-Xaa$^{31}$-Xaa$^{32}$-Xaa$^{33}$-Xaa$^{34}$-Xaa$^{35}$-

Xaa$^{36}$-Xaa$^{37}$-Xaa$^{38}$-Xaa$^{39}$-Xaa$^{40}$-Xaa$^{41}$-Xaa$^{42}$-

Xaa$^{43}$-Xaa$^{44}$-Xaa$^{45}$ wherein Xaa$^8$ is Ala, Gly, Ser, Thr, Leu, Ile, Val, Glu, Asp, Met, or Lys, Xaa$^9$ is Glu, Asp, or Lys, Xaa$^{11}$ is Thr, Ala, Gly, Ser, Leu, Ile, Val, Glu, Asp, or Lys, Xaa$^{14}$ is Ser, Ala, Gly, Thr, Leu, Ile, Val, Glu, Asp, or Lys, Xaa$^{16}$ is Val, Ala, Gly, Ser, Thr, Leu, Ile, Tyr, Glu, Asp, or Lys, Xaa$^{17}$ is Ser, Ala, Gly, Thr, Leu, Ile, Val, Glu, Asp, or Lys, Xaa$^{18}$ is Ser, Ala, Gly, Thr, Leu, Ile, Val, Glu, Asp, or Lys, Xaa$^{19}$ is Tyr, Phe, Trp, Glu, Asp, or Lys, Xaa$^{20}$ is Leu, Ala, Gly, Ser, Thr, Leu, Ile, Val, Glu, Asp, or Lys, Xaa$^{21}$ is Glu, Asp, or Lys, Xaa$^{22}$ is Gly, Ala, Ser, Thr, Leu, Ile, Val, Glu, Asp, or Lys, $Xaa^{23}$ is Gln, Asn, Arg, Glu, Asp, or Lys, $Xaa^{24}$ is Ala, Gly, Ser, Thr, Leu, Ile, Val, Arg, Glu, Asp, or Lys, $Xaa^{25}$ is Ala, Gly, Ser, Thr, Leu, Ile, Val, Glu, Asp, or Lys, $Xaa^{26}$ is Lys, Arg, Gln, Glu, Asp, or His, $Xaa^{27}$ is Glu, Asp, or Lys, $Xaa^{36}$ is Ala, Gly, Ser, Thr, Leu, Ile, Val, Glu, Asp, or Lys, $Xaa^{31}$ is Trp, Phe, Tyr, Glu, Asp, or Lys, $Xaa^{32}$ is Leu, Gly, Ala, Ser, Thr, Ile, Val, Glu, Asp, or Lys, $Xaa^{33}$ is Val, Gly, Ala, Ser, Thr, Leu, Ile, Glu, Asp, or Lys, $Xaa^{34}$ is Lys, Arg, Glu, Asp, or His, $Xaa^{35}$ is Gly, Ala, Ser, Thr, Leu, Ile, Val, Glu, Asp, or Lys, $Xaa^{36}$ is Arg, Lys, Glu, Asp, or His, $Xaa^{37}$ is Gly, Ala, Ser, Thr, Leu, Ile, Val, Glu, Asp, or Lys, or is deleted, $Xaa^{38}$ is Arg, Lys, Glu, Asp, or His, or is deleted, $Xaa^{39}$ is Arg, Lys, Glu, Asp, or His, or is deleted, $Xaa^{40}$ is Asp, Glu, or Lys, or is deleted, $Xaa^{41}$ is Phe, Trp, Tyr, Glu, Asp, or Lys, or is deleted, $Xaa^{42}$ is Pro, Lys, Glu, or Asp, or is deleted, $Xaa^{43}$ is Glu, Asp, or Lys, or is deleted, $Xaa^{44}$ is Glu, Asp, or Lys, or is deleted, and $Xaa^{45}$ is Val, Glu, Asp, or Lys, or is deleted, or a $C_{1-6}$-ester, amide, $C_{1-6}$-alkylamide, or $C_{1-6}$-dialkylamide thereof and/or a pharmaceutically acceptable salt thereof, provided that (i) when the amino acid at position 37, 38, 39, 40, 41, 42, 43 or 44 is deleted, then each amino acid downstream (i.e., toward the C-terminus) of the amino acid is also deleted, (ii) the derivative of the GLP-1 analog contains only one or two Lys, (iii) the ε-amino group of one or both Lys is optionally substituted with a lipophilic substituent optionally via a spacer, and (iv) the total number of different amino acids between the derivative of the GLP-1 analog and the corresponding native form of GLP-1 or fragment thereof does not exceed six.

In certain embodiments, in compounds with structure of Formula VIII, $Xaa^8$ is Val. In certain embodiments, the ε-amino group of one Lys residue is substituted with a lipophilic substituent optionally via a spacer. In certain embodiments, the ε-amino group of more than one Lys residue is substituted with a lipophilic substituent optionally via a spacer. In certain embodiments, the ε-amino group of two Lys residues are independently substituted with a lipophilic substituent optionally via a spacer.

Exemplary compounds with structure of Formula VIII include, without limitation: $Lys^{34}(N^\epsilon-(\gamma$-glutamyl$(N^\alpha$-tetradecanoyl)))GLP-1(7-37); $Arg^{26,34}$, $Lys^8(N^\epsilon-(\gamma$-glutamyl$(N^\alpha$-hexadecanoyl)))GLP-1(7-37); $Arg^{34}$, $Lys^{26}$ $(N^\epsilon(\gamma$-glutamyl$(N^\alpha$-dodecanoyl)))GLP-1(7-37); $Arg^{34}$, $Lys^{26}$ $(N^\epsilon$ (β-alanyl$(N^\alpha$-hexadecanoyl)))GLP-1(7-37); $Arg^{34}$, $Lys^{26}(N^\epsilon$ (α-glutamyl $(N^\alpha$-hexadecanoyl)))GLP-1(7-37); $Arg^{34}$, $Lys^{26}$ $(N^\epsilon$(piperidinyl-4-carbonyl (N-hexadecanoyl)))GLP-1(7-37); and $Arg^{34}$, $Lys^{26}(N^\epsilon(\gamma$-glutamyl$(N^\alpha$-decanoyl)))GLP-1 (7-37).

Some embodiments of the methods described herein further contemplate amino acid functionalization with a lipophilic substituent. Accordingly, in certain embodiments, GLP-1 receptor agonist compounds contemplated for the practice of the methods described herein include without limitation compounds described in U.S. Pat. No. 6,268,343 filed Feb. 26, 1999, entitled "Derivatives of GLP-1 Analogs," which is herein incorporated by reference in its entirety and for all purposes, which purposes include the lipophilic substituted peptides and formulations thereof taught therein. In certain embodiments, compounds are contemplated with the structure of Formula IX (SEQ ID NO: 33):

$His^7-Xaa^8-Xaa^9-Gly^{10}-Xaa^{11}-Phe^{12}-Thr^{13}-Xaa^{14}-$ IX $Asp^{15}-Xaa^{16}-Xaa^{17}-Xaa^{18}-Xaa^{19}-Xaa^{20}-Xaa^{21}-$ $Xaa^{22}-Xaa^{23}-Xaa^{24}-Xaa^{25}-Xaa^{26}-Xaa^{26}-Xaa^{27}-$

-continued $Phe^{28}-Ile^{29}-Xaa^{30}-Xaa^{31}-Xaa^{32}-Xaa^{33}-Xaa^{34}-$ $Xaa^{35}-Xaa^{36}-Xaa^{37}$ wherein $Xaa^8$ is Ala, $Xaa^9$ is Glu, $Xaa^{11}$ is Thr, $Xaa^{14}$ is Ser, $Xaa^{16}$ is Val, $Xaa^{17}$ is Ser, $Xaa^{18}$ is Ser, $Xaa^{19}$ is Tyr, $Xaa^{20}$ is Leu, $Xaa^{21}$ is Glu, $Xaa^{22}$ is Gly, $Xaa^{23}$ is Gln, $Xaa^{24}$ is Ala, $Xaa^{25}$ is Ala, $Xaa^{26}$ is Lys, $Xaa^{27}$ is Glu, $Xaa^{30}$ is Ala, $Xaa^{31}$ is Trp, $Xaa^{32}$ is Leu, $Xaa^{33}$ is Val, $Xaa^{34}$ is Arg, $Xaa^{35}$ is Gly, $Xaa^{36}$ is Arg, and $Xaa^{37}$ is Gly, wherein (a) the ε-amino group of $Lys^{26}$ is substituted with a lipophilic substituent, optionally via a spacer, (b) the lipophilic substituent is (i) $CH_3(CH_2)_n$CO— wherein n is 6, 8, 10, 12, 14, 16, 18, 20 or 22, (ii) $HOOC(CH_2)_m$CO— wherein m is 10, 12, 14, 16, 18, 20 or 22, or (iii) lithocholoyl, and (c) the spacer is (i) an unbranched alkane α,ω-dicarboxylic acid group having from 1 to 7 methylene groups, (ii) an amino acid residue except Cys, or (iii) γ-aminobutanoyl.

In certain embodiments, in the GLP-1 derivative of Formula IX, the lipophilic substituent is linked to the α-amino group of Lys via a spacer. In certain embodiments, the spacer is γ-glutamyl. In certain embodiments, the spacer is β-asparagyl. In certain embodiments, the spacer is glycyl. In certain embodiments, the spacer is γ-aminobutanoyl. In certain embodiments, the spacer is β-alanyl.

In certain embodiments, the compound with structure of Formula IX is $Lys^{26}(N^\epsilon$-tetradecanoyl), $Arg^{34}$-GLP-1(7-37). In certain embodiments, the compound with structure of Formula IX is $Lys^{26}(N^\epsilon$-(ω-carboxynonadecanoyl)), $Arg^{34}$-GLP-1(7-37). In certain embodiments, the compound with structure of Formula IX is $Lys^{26}(N^\epsilon$-(ω-carboxyheptadecanoyl)), $Arg^{34}$-GLP-1(7-37). In certain embodiments, the compound with structure of Formula IX is $Lys^{26}(N^\epsilon$-(ω-carboxyundecanoyl)), $Arg^{34}$-GLP-1(7-37). In certain embodiments, the compound with structure of Formula IX is $Lys^{26}$ $(N^\epsilon$-(ω-carboxypentadecanoyl)), $Arg^{34}$-GLP-1(7-37). In certain embodiments, the compound with structure of Formula IX is $Lys^{26}(N^\epsilon$-lithocholoyl), $Arg^{34}$-GLP-1(7-37). In certain embodiments, the compound with structure of Formula IX is $Lys^{26}(N^\epsilon$-(γ-glutamyl$(N^\alpha$-hexadecanoyl))), $Arg^{34}$-GLP-1(7-37). In certain embodiments, the compound with structure of Formula IX is $Lys^{26}(N^\epsilon$-(γ-glutamyl$(N^\alpha$-tetradecanoyl))), $Arg^{34}$-GLP-1(7-37). In certain embodiments, the compound with structure of Formula IX is $Lys^{26}$ $(N^\epsilon$-(γ-glutamyl$(N^\alpha$-lithocholoyl))), $Arg^{34}$-GLP-1(7-37). In certain embodiments, the compound with structure of Formula IX is $Lys^{26}(N^\epsilon$-(γ-glutamyl$(N^\alpha$-octadecanoyl))), $Arg^{34}$-GLP-1(7-37). In certain embodiments, the compound with structure of Formula IX is $Lys^{26}(N^\epsilon$-decanoyl), $Arg^{34}$-GLP-1(7-37). In certain embodiments, the compound with structure of Formula IX is $Lys^{26}(N^\epsilon$-hexadecanoyl), $Arg^{34}$-GLP-1(7-37). In certain embodiments, the compound with structure of Formula IX is $Lys^{26}(N^\epsilon$-octanoyl), $Arg^{34}$-GLP-1 (7-37). In certain embodiments, the compound with structure of Formula IX is $Lys^{26}(N^\epsilon$-dodecanoyl), $Arg^{34}$-GLP-1(7-37). In certain embodiments, the compound with structure of Formula IX is $Lys^{26}(N^\epsilon$(γ-aminobutyroyl-$(N^\gamma$-hexadecanoyl))), $Arg^{34}$-GLP-1(7-37). In certain embodiments, the compound with structure of Formula IX is $Lys^{26}(N^\epsilon$-(γ-D-glutamyl$(N^\alpha$-hexadecanoyl))), $Arg^{34}$-GLP-1(7-37). In certain embodiments, the compound with structure of Formula IX is $Lys^{26}$ $(N^\epsilon$-(γ-glutamyl$(N^\alpha$-dodecanoyl))), $Arg^{34}$-GLP-1(7-37). In certain embodiments, the compound with structure of Formula IX is $Lys^{26}(N^\epsilon$-(β-alanyl$(N^\alpha$-hexadecanoyl))), $Arg^{34}$-GLP-1(7-37). In certain embodiments, the compound with structure of Formula IX is $Lys^{26}(N^\epsilon$-(α-glutamyl$(N^\alpha$-hexadecanoyl))), Arg$^{34}$-GLP-1(7-37). In certain embodiments, the compound with structure of Formula IX is Lys$^{26}$(N$^\epsilon$-(γ-glutamyl(N$^\alpha$-decanoyl))), Arg$^{34}$-GLP-1(7-37).

Some embodiments of the methods described herein contemplate conjugates of an exendin, exendin agonist or GLP-1 receptor agonist to a macromolecule. Useful conjugated peptides for the methods described herein include exendins, exendin agonists and GLP-1 receptor agonists and derivatives thereof conjugated to a macromolecule. In certain embodiments, the macromolecule is a peptide, a blood-protein-binding peptide, a hormone, a polypeptide, an albumin, a polyamino acid, a fatty acyl group, a diacid, a water soluble polymer, an immunoglobulin or an immunoglobulin fragment, or a catalytic antibody or fragment thereof. In certain embodiments, the macromolecule is a blood protein. In one embodiment, the macromolecule is albumin. Methods known in the art can be used to link an exendin, exendin agonist or GLP-1 receptor agonist peptide to a macromolecule. In certain embodiments, the peptide is linked to albumin according to any technique known to those of skill in the art. In some embodiments, the peptide is modified to include a reactive group which can react with available reactive functionalities on albumin to form a covalent linkage. In certain embodiments, two of said macromolecules are present and are selected from the group consisting of a peptide, a blood-protein-binding peptide, a hormone, a polypeptide, an albumin, a polyamino acid, a fatty acyl group, a diacid, a water soluble polymer, an immunoglobulin or an immunoglobulin fragment, or a catalytic antibody or fragment thereof. Accordingly, in some embodiments, compounds contemplated in the practice of the methods described herein include without limitation those described in Published Application WO 2007/053946, entitled "Method of Treating Diabetes and/or Obesity with Reduced Nausea Side Effects using an Insulinotropic Peptide Conjugated to Albumin," which application is herein incorporated by reference in its entirety and for all purposes, which purposes include the exendin, exendin agonist or GLP-1 receptor agonist conjugates and formulations thereof taught therein.

In some embodiments, compounds conjugated with blood proteins include modified peptides comprising a reactive group which reacts with amino groups, hydroxyl groups or thiol groups on blood proteins to form stable covalent bonds. Exemplary reactive groups include NHS(N-hydroxysuccinimide), sulfo-NHS(N-hydroxy-sulfosuccinimide), MBS (maleimide-benzoyl-succinimide), GMBS (gamma-maleimid-butyryloxy succinimide ester), and MPA (maleimidopropionic acid), and the like. Exemplary reactive group containing peptides include without limitation GLP-1(1-36)-Lys$^{37}$(ε-MPA)-NH$_2$; GLP-1(1-36)-Lys$^{37}$(ε-AEEA-AEEA-MPA)-NH$_2$; GLP-1(7-36)-Lys$^{37}$(ε-MPA)-NH$_2$; GLP-1(7-36)-Lys$^{37}$(ε-AEEA-AEEA-MPA)-NH$_2$, D-Ala2 GLP-1(7-36)-Lys$^{37}$(ε-MPA)-NH$_2$; Exendin-4(1-39)-Lys$^{40}$(ε-MPA)-NH$_2$; Exendin-4(1-39)-Lys$^{40}$(ε-AEEA-AEEA-MPA)-NH$_2$; Exendin-3(1-39)-Lys$^{40}$(ε-MPA)-NH$_2$; Exendin-3(1-39)-Lys$^{40}$(ε-AEEA-AEEA-MPA)-NH$_2$; Lys$^{26}$(ε-MPA)GLP-1(7-36)-NH$_2$; GLP-1(7-36)-EDA-MPA; and Exendin-4(1-39)-EDA-MPA. "AEEA" refers to the linking group [2-(2-amino) ethoxy)]ethoxy acetic acid. "EDA" refers to ethylenediamine. Methods for preparing compounds containing reactive groups, and for the covalent attachment of peptides with blood proteins are well known in the art.

In some embodiments, the conjugated peptide comprises albumin Cys$^{34}$ thiol covalently linked to a [2-[2-[2-maleimidopropionamido(ethoxy)ethoxy]acetamide linker on the ε-amino of a lysine of the exendin, exendin agonist or GLP-1 receptor agonist peptide. In certain embodiments, the lysine has been added to the native peptide sequence. In certain embodiments, the lysine has been added to the carboxy terminus of the peptide. In certain embodiments, the peptide is selected from the group consisting of GLP-1, exendin-3, and exendin-4, and analogs and derivatives thereof including each of the species described herein. In certain embodiments, the peptide is exendin-4(1-39). In certain embodiments, the albumin is human serum albumin. In certain embodiments, the albumin is recombinant serum albumin as known in the art. In certain embodiments, the albumin is recombinant human serum albumin. In certain embodiments, the conjugated peptide comprises recombinant human serum albumin Cys$^{34}$ thiol covalently linked to a [2-[2-[2 maleimidopropionamido (ethoxy)ethoxy]acetamide linker on the ε-amino of the carboxy terminal lysine of exendin-4(1-39)Lys.

Some embodiments of the methods described herein contemplate an exendin or exendin agonist or GLP-1 receptor agonist coupled with polyethylene glycol (PEG). Accordingly, in some embodiments, GLP-1 receptor agonist compounds contemplated in the practice of the methods described herein include without limitation those described in Published Application WO 2006/124529, filed May 11, 2006, entitled "GLP-1 Pegylated Compounds," which application is herein incorporated by reference in its entirety and for all purposes, which purposes include the pegylated compounds useful for the methods described herein and formulation thereof taught therein. Useful compounds contemplated in this context include compounds with structure of Formula X (SEQ ID NO: 34)

```
His-Xaa⁸-Glu-Gly-Thr-Phe-Thr-Ser-Asp-Val-Ser-Ser-    X
Tyr-Leu-Glu-Xaa²²-Gln-Ala-Ala-Lys-Glu-Phe-He-Ala-
Trp-Leu-Xaa³³-Lys-Gly-Gly-Pro-Ser-Ser-Gly-Ala-
Pro-Pro-Pro-Cys⁴⁵-Xaa⁴⁶
``` wherein Xaa$^8$ is D-Ala, Gly, Val, Leu, Ile, Ser, or Thr; Xaa$^{22}$ is Gly, Glu, Asp, or Lys; Xaa$^{33}$ is Val or Ile Xaa$^{46}$ is Cys or Cys-NH$_2$, and wherein one PEG molecule is covalently attached to Cys$^{45}$ and one PEG molecule is covalently attached to Cys$^{46}$ or Cys$^{46}$—NH$_2$. The term "pegylated" when referring to a GLP-1 receptor agonist refers to a GLP-1 receptor agonist that is chemically modified by covalent attachment of two molecules of polyethylene glycol or a derivative thereof. Furthermore, it is intended that the term "PEG" refers to polyethylene glycol or a derivative thereof as are known in the art (see, e.g., U.S. Pat. Nos. 5,445,090; 5,900,461; 5,932,462; 6,436,386; 6,448,369; 6,437,025; 6,448,369; 6,495,659; 6,515,100 and 6,514,491). In one embodiment of pegylated GLP-1 receptor agonist compounds, PEG (or a derivative thereof) is covalently attached to two introduced cysteine residues in the GLP-1 receptor agonist. In a further embodiment the two introduced cysteine residues in the GLP-1 receptor agonist are at position 45 and 46. In certain embodiments, the PEG polymers have molecular weights between 500 and 100,000 daltons, or between 5,000 and 40,000 daltons, or between 20,000 and 60,000 daltons, or between 20,000 and 40,000 daltons, and may be linear or branched molecules, and may be polyethylene glycol derivatives as described in the art. In still a further embodiment the PEG is a 20 kilodalton linear methoxy PEG maleimide.

Some embodiments of the methods described herein contemplate analogs of GLP-1 useful as GLP-1 receptor agonists. Accordingly, in some embodiments, GLP-1 receptor agonist compounds contemplated herein include without limitation those described in Published Application WO 98/43658, filed Mar. 25, 1998, entitled "Glucagon-like Peptide-1 Analogs," which application is herein incorporated by reference in its entirety and for all purposes, which purposes include the GLP-1 receptor agonists and formulations thereof taught therein. In this context, compound useful in the practice of the methods described herein include GLP-1 receptor agonists with structure of Formula XI (SEQ ID NO: 35):

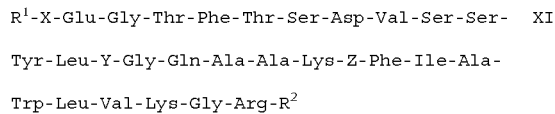

or a pharmaceutically acceptable salt thereof, wherein $R^1$ is selected from the group consisting of His, D-histidine, desamino-histidine, 2-amino-histidine, □-hydroxy-histidine, homohistidine, □-fluoromethylhistidine, and □-methyl-histidine; X is selected from the group consisting of Met, Asp, Lys, Thr, Leu, Asn, Gln, Phe, Val and Tyr; Y and Z are independently selected from the group consisting of Glu, Gln, Ala, Thr, Ser, and Gly, and; $R^2$ is selected from the group consisting of $NH_2$ and Gly-OH; provided that, if $R^1$ is His, X is Ala or Val, Y is Glu and Z is Glu, then $R^2$ is $NH_2$. Exemplary compounds with structure of Formula XI include $Met^8GLP-1(7-36)NH_2$ and $Thr^8GLP-1(7-37)-OH$.

Some embodiments of the methods described herein contemplate analogs of GLP-1 useful as GLP-1 receptor agonists. Accordingly, in some embodiments, GLP-1 receptor agonist compounds contemplated in the practice of the methods described herein include without limitation those described in U.S. Pat. No. 5,512,549, filed Oct. 18, 1994, entitled "Glucagon-like Insulinotropic Peptide Analogs, Compositions, and Methods of Use," which application is herein incorporated by reference in its entirety and for all purposes, which purposes include the GLP-1 receptor agonists and formulations thereof described therein. In this context, compounds useful in the practice of the methods described herein include GLP-1 receptor agonists with structure of Formula XII (SEQ ID NO: 36):

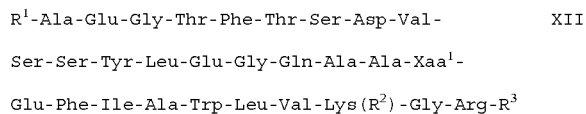

wherein $R^1$ is selected from the group consisting of 4-imidazopropionyl, 4-imidazoacetyl, or 4-imidazo-□,□-dimethylacetyl; $R^2$ is selected from the group consisting of $C_5$-$C_{10}$ unbranched acyl, or is absent; $R^3$ is selected from the group consisting of Gly-OH or $NH_2$; and, $Xaa^1$ is Lys or Arg. In certain embodiments, $R^1$ is 4-imidazopropionyl, $R^2$ is $C_8$ unbranched acyl, $R^3$ is Gly-OH, and $Xaa^1$ is Arg. In certain embodiments, $R^2$ is absent. In certain embodiments, $R^1$ is 4-imidazoacetyl and $R^2$ is $C_8$ unbranched acyl. In certain embodiments, $R^1$ is 4-imidazo-□,□-dimethyl-acetyl and $R^2$ is $C_8$ unbranched acyl. Exemplary compounds with the structure of Formula XII include, without limitation, [Arg$^{26}$]GLP-1(8-37)OH, [Lys$^{34}$-N□-Octanoyl]GLP-1(7-37))OH, N-Imidazopropionyl-GLP-1(8-37)OH, N-Imidazopropionyl-[Arg$^{26}$]GLP-1(8-37)OH, N-imidazopropionyl-[Arg$^{26}$, Lys$^{34}$-N□-Octanoyl]GLP-1(8-37))OH, N-imidazoacetyl-[Arg$^{26}$]GLP-1(8-37))OH, N-[Imidazole-□,□-dimethyl-acetyl]GLP-1(8-37)OH, and N-imidazoacetyl-GLP-1(8-36)NH$_2$.

In some embodiments, exendin and exendin agonist and GLP-1 receptor agonist compounds contemplated in the practice of the methods described herein include without limitation those prepared as in or described in Published Application WO 02/098348, filed May 21, 2002, entitled "GLP-1 Formulations with Protracted Time Action," and U.S. Pat. No. 7,144,863, which is a national stage filing thereof, which applications are herein incorporated by reference in their entireties and for all purposes, including the particles and their making described therein. Provided for the methods herein is a composition comprising particles wherein the particles are comprised of an exendin, exendin agonist or GLP-1 receptor agonist complexed with a basic polypeptide. The basic polypeptide can be selected from the group consisting of polylysine, polyarginine, polyornithine, protamine, putrescine, spermine, spermidine, and histone. The mass ratio of compound to basic polypeptide in the composition is between about 4:1 and about 10:1. The mean number diameter of the particles is between 1 μm and 5 μm. In one embodiment the compound comprises any one of the exendin, exendin agonists or GLP-1 receptor agonists described herein or in WO 02/098348.

"Basic polypeptides" include but are not limited to basic proteins or polyamines. Examples of basic proteins or polyamines are polylysine, polyarginine, polyornithine, protamine, putrescine, spermine, spermidine, and histone. In one embodiment basic polypeptides are polyarginine, protamine, polylysine, polyaspartic acid, polyglutamic acid, and polyornithine. In another embodiment the basic peptide is polylysine, polyarginine, and protamine. In yet a further embodiment is protamine. Protamine is the generic name of a group of strongly basic proteins present in sperm cell nuclei in salt like combination with nucleic acids. Commercially available protamines can be isolated from mature fish sperm and are usually obtained as the sulfate. The peptide composition of a specific protamine may vary depending on which family, genera or species of fish it is obtained from. Protamine from salmon or trout can be separated into two, three, or more main fractions of proteins that may be separated further. The different parent peptides consist of about 30 amino acids of which more than 20 are arginines. The average molecular weight of protamine is about 4,300. Commercially available protamine sulfate is approximately 80% protamine. "Particle" in the context of compounds described in the present specification refers to a solid material complex comprising an exendin, exendin agonist or GLP-1 receptor agonist compound and a basic polypeptide. The particles optionally comprise divalent metal ions. The particles are comprised of either crystalline or amorphous material or a mixture of crystalline and amorphous material. A crystalline particle is a particle comprised primarily of individual or clusters of microcrystals, rods, needles, or plates or mixtures thereof. The crystalline particles can be comprised of small clusters of plate-like microcrystals. Further, the crystalline particles can be homogeneous in size and shape (unimodal) and appear as small clusters of plate-like microcrystals. The particles of the present invention have a number diameter that ranges from about 0.5 μm to about 12 μm. Particles can have a number diameter that ranges from about 1 μm to about 5 μm. Further, the particles can have a number diameter that ranges from about 1 μm to about 3 μm. The number mean diameter of the crystalline particles in a composition can be from about 1 μm to about 5 μm. Further, the number mean diameter of the crystalline particles in a composition can be from about 1 μm to about 3 μm. Even further, the number mean diameter of the crystalline particles in a composition is from about 3 μm to about 5 μm. Yet even further, the number mean diameter of the crystalline particles in a composition is from about 4 µm to about 5 µm. Yet even further, 90% of the particles in the composition are less than 12 µm. Further yet, 90% of the particles in the composition are less than 9 µm, and in a further embodiment most are less than 7 µm. The number diameters can be determined using a Coulter Multisizer II (Coulter Electronics Limited, Luton, Beds, England). The Coulter Multisizer uses an electrical sensing zone technique. Particle size, volume, and surface area distributions are calculated based on measurable changes in electrical resistance produced by non-conductive particles suspended in an electrolyte. An amorphous particle for the purposes of the present invention refers to a particle comprising a precipitate, but lacking matter in a crystalline state and a definable form or structure as determined by polarized light microscopy.

Accordingly, the particles formed from an exendin, exendin agonist or GLP-1 receptor agonist, such as a GLP-1 compound described herein or in WO 02/098348 and a basic polypeptide can be added together at a ratio between about 4:1 and about 10:1 (weight per weight) (w/w), further at a ratio between about 5:1 and about 10:1 (w/w), even further at a ratio between about 6:1 and about 10:1 (w/w), and yet even further at a ratio between about 7:1 and about 9:1 (w/w) (compound:basic polypeptide). Additionally, in one embodiment the composition is a mixture of particle preparations wherein particles formed from mixing, precipitating, or crystallizing a compound and a basic polypeptide at one ratio are mixed with particles formed from mixing, precipitating, or crystallizing a compound and a basic polypeptide at another ratio. The particles are soluble in that the amount of drug compound in particle form will dissolve in phosphate buffered saline (PBS) in a given desired period of time. Typically, a dried particle preparation is suspended in phosphate buffered saline (PBS) such that the final concentration of drug compound is 1 mg/mL. The resulting suspension is gently stirred for one hour at room temperature. Solubility is then determined by measuring the concentration of the drug compound released, such as by UV absorbance measurements or HPLC. In one embodiment the solubility range for the particles in PBS can range from about 0.5 mg/ml to about 0.1 mg/ml.

In one embodiment the particle composition can be administered by a pulmonary route, to a lower airway of the patient, or inhaled through the mouth of the patient. The particle composition can be delivered from an inhalation device suitable for pulmonary administration and capable of depositing the composition in the lungs of the patient, for example the device can be a nebulizer, a metered-dose inhaler, a dry powder inhaler, or a sprayer.

Embodiments of the methods described herein contemplate an exendin, exendin agonist or GLP-1 receptor agonist linked to a macromolecule, such as a peptide, a blood-protein-binding peptide, a hormone, a polypeptide, an albumin, a polyamino acid, a fatty acyl group, a diacid, a water soluble polymer, an immunoglobulin or an immunoglobulin fragment, such as an Fc fragment, or a catalytic antibody or fragment thereof. Such macromolecules provide a longer circulating half-life compared to the unconjugated compound, while maintaining bioactivity and often improving solubility compared to the unconjugated drug compound. Accordingly, compounds contemplated in the practice of the methods described herein include without limitation those described in Published Application WO 02/46227, filed Nov. 29, 2001, entitled "GLP-1 Fusion Proteins," and related published applications WO 2004/110472 and WO 2006/068910, which applications are herein incorporated by reference in their entirety and for all purposes, which purposes include the macromolecules described therein and their exendin, exendin agonist and GLP-1 receptor agonist conjugates and methods of making and formulating. In this context the heterologous fusion proteins (conjugates) comprise an exendin, exendin agonist or a GLP-1 receptor agonist compound fused to or conjugated to human albumin, a human albumin analog, a human albumin fragment, an immunoglobulin, the Fc portion of an immunoglobulin, an analog of the Fc portion of an immunoglobulin, or a fragment of the Fc portion of an immunoglobulin. Typically, the C-terminus of the compound can be fused directly, or fused via a peptide linker, to the N-terminus of the macromolecule, such as an albumin or Fc protein. In the case of a catalytic macromolecule, such as a catalytic antibody, the compound is conjugated to a linker that is recognized by the catalytic antibody hapten biding site, which then covalently reacts with the linker, thus conjugating the compound at a precise location on the antibody. These heterologous fusion proteins are biologically active and have an increased half-life compared to native exendin or GLP-1 or their unconjugated analog or derivative form. The macromolecule can have a long circulating half-life, such as human serum albumin or the Fc portion of an immunoglobulin, or in any event the conjugate will have a longer circulating half-life than the unconjugated drug.

In one embodiment the heterologous fusion proteins comprise an exendin, exendin agonist or a GLP-1 receptor compound fused to human albumin, a human albumin analog, a human albumin fragment, the Fc portion of an immunoglobulin, an analog of the Fc portion of an immunoglobulin, or a fragment of the Fc portion of an immunoglobulin. The C-terminus of the drug compound may be fused directly, or fused via a peptide linker, to the N-terminus of an albumin, IgG or Fc protein. These heterologous fusion proteins are biologically active and have an increased half-life compared to the unconjugated compound.

Accordingly, in one embodiment are the formulas of heterologous proteins DE-L-M and DG-L-M, where DE is an exendin or exendin agonist and DG is a GLP-1 receptor agonist, such as Val8-GLP-1(7-36) or analog thereof, and wherein L is an optionally present linker and M is a macromolecule. In one embodiment the heterologous fusion protein comprises a first polypeptide DE or DG with a N-terminus and a C-terminus fused to a second polypeptide M with a N-terminus and a C-terminus wherein the first polypeptide is exendin or exendin agonist or is a GLP-1 receptor agonist and the second polypeptide is selected from the group consisting of a) the Fc portion of an immunoglobulin; b) an analog of the Fc portion of an immunoglobulin; and c) fragments of the Fc portion of an immunoglobulin, and wherein the C-erminus of the first polypeptide is fused to the N-terminus of the second polypeptide. In yet another embodiment, the heterologous fusion protein comprises a first polypeptide DE OR DG with a N-terminus and a C-terminus fused to a second polypeptide M with a N-terminus and a C-terminus wherein the first polypeptide is a GLP-1 compound and the second polypeptide is selected from the group consisting of a) the Fc portion of an immunoglobulin; b) an analog of the Fc portion of an immunoglobulin; and c) fragments of the Fc portion of an immunoglobulin, and wherein the C-terminus of the first polypeptide is fused to the N-terminus of the second polypeptide via a peptide linker. Accordingly, in another embodiment of the formulates DE-L-M and DG-L-M, the second polypeptide M is selected from the group consisting of a) human albumin; b) human albumin analogs; and c) fragments of human albumin, and wherein the C-terminus of the first polypeptide DE or DG is fused to the N-terminus of the second polypeptide. In yet another embodiment, M is selected from the group consisting of 20 a) human albumin; b) human albumin analogs; and c) fragments of human albumin, and wherein the C-terminus of the first polypeptide is fused to the N-terminus of the second polypeptide via a peptide linker. For example, the peptide linker can be a) a glycine rich peptide; b) a peptide having the sequence [Gly-Gly-Gly-Gly-Ser]$_n$ (SEQ IN NO: 37) where n is 1, 2, 3, 4, 5, or 6; and c) a peptide having the sequence [Gly-Gly-Gly-Gly-Ser]$_3$ (SEQ IN NO: 38). The Fc portion of an Ig can be selected from the group consisting of: IgG1, IgG2, IgG3, IgG4, IgE, IgA, IgD, or IgM. The Fc portion of an Ig can be selected from the group consisting of IgG1, IgG2, IgG3, and IgG4. The Fc portion can be an IgG4 immunoglobulin. In still further embodiment the blood protein, albumin or IgG is human. In yet another embodiment the Fc portion comprises the hinge, CH2, and CH3 domains. Further examples of linkers for use with any of the macromolecules including FC and albumin fusions, include a linker that is a G-rich peptide linker having the sequence Gly-Gly-Gly-Gly-Ser-Gly-Gly-Gly-Gly-Ser-Gly-Gly-Gly-Gly-Ser (SEQ ID NO: 38). Other examples of linkers include, but are not limited to, Gly-Ser-Gly-Gly-Gly Gly-Ser-Gly-Gly-Gly-Gly-Ser-Gly-Gly-Gly-Gly-Ser-Gly-Gly-Gly-Gly-Ser (SEQ ID NO: 39); Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser (SEQ ID NO: 40); Asp-Ala Ala-Ala-Lys-Glu-Ala-Ala-Ala-Lys-Asp-Ala-Ala-Ala-Arg-Glu-Ala-Ala-Ala-Arg-Asp Ala-Ala-Ala-Lys (SEQ ID NO; 41 and Asn-Val-Asp-His-Lys-Pro-Ser-Asn-Thr-Lys-Val Asp-Lys-Arg (SEQ ID NO: 42).

Thus, in one embodiment the drug compounds described herein and in WO02/46227 can be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class. As used herein, the Fc portion of an immunoglobulin has the meaning commonly given to the term in the field of immunology. Specifically, this term refers to an antibody fragment which is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W.H. Freeman and Co., 1992, the teachings of which are herein incorporated by reference. The Fc portion can further include one or more glycosylation sites. There are five types of human immunoglobulin Fc regions with different effect or and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which has different effect or functions. G1, G2, and G3 can bind Clq and fix complement while G4 cannot. Even though G3 is able to bind Clq more efficiently than G1, G1 is more effective at mediating complement-directed cell lysis. G2 fixes complement very inefficiently. The Clq binding site in IgG is located at the carboxy terminal region of the CH2 domain. All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain. IgA can exist both in a monomeric and dimeric form held together by a J-chain. IgA is the second most abundant Ig in serum, but it has a half-life of only 6 days. IgA has three effect or functions. It binds to an IgA specific receptor on macrophages and eosinophils, which drives phagocytosis and degranulation, respectively. It can also fix complement via an unknown alternative pathway. IgM is expressed as either a pentamer or a hexamer, both of which are held together by a J-chain. IgM has a serum half-life of 5 days. It binds weakly to Clq via a binding site located in its CH3 domain. IgD has a half-life of 3 days in serum. It is unclear what effect or functions are attributable to this Ig. IgE is a monomeric Ig and has a serum half-life of 2.5 days. IgE binds to two Fc receptors which drives degranulation and results in the release of proinflammatory agents. Depending on the desired effect, the heterologous fusion proteins may contain any of the isotopes described above or may contain mutated Fc regions wherein the complement and/or Fc receptor binding functions have been altered. Thus, the heterologous-fusion proteins may contain the entire Fc portion of an immunoglobulin, fragments of the Fc portion of an immunoglobulin, or analogs thereof fused to an exendin, exendin agonist or a GLP-1 receptor agonist compound.

The fusion proteins can consist of single chain proteins or as multi-chain polypeptides. Two or more Fc fusion proteins can be produced such that they interact through disulfide bonds that naturally form between Fc regions. These multimers can be homogeneous with respect to the drug compound or they may contain different drug compounds fused at the N-terminus of the Fc portion of the fusion protein. Regardless of the final structure of the fusion protein, the Fc or Fc-like region must serve to prolong the in vivo plasma half-life of the drug compound fused at the N-terminus. Furthermore, the fused drug compound must retain some biological activity.

Since the Fc region of IgG produced by proteolysis has the same in vivo half-life as the intact IgG molecule and Fab fragments are rapidly degraded, it is believed that the relevant sequence for prolonging half-life reside in the CH2 and/or CH3 domains. Further, it has been shown in the literature that the catabolic rates of IgG variants that do not bind the high-affinity Fc receptor or Clq are indistinguishable from the rate of clearance of the parent wild-type antibody, indicating that the catabolic site is distinct from the sites involved in Fc receptor or Clq binding. (Wawrzynczak et al., (1992) Molecular Immunology 5 29:221). Site-directed mutagenesis studies using a marine IgG1 Fc region suggested that the site of the IgG1 Fc region that controls the catabolic rate is located at the CH2-CH3 domain interface. Based on these studies, Fc regions can be modified at the catabolic site to optimize the half-life of the fusion proteins. In one embodiment the Fc region used for the heterologous fusion proteins can be derived from an IgG1 or an IgG4 Fc region. Yet further the Fc region can be IgG4 or derived from IgG4. Even further the IgG Fc region contains both the CH2 and CH3 regions including the hinge region.

Thus in another embodiment the exendin, exendin agonist or GLP-1 receptor agonist compound can be fused directly or via a peptide linker to albumin or an analog, fragment, or derivative thereof. Generally the albumin proteins making up part of the fusion proteins can be derived from albumin cloned from any species. However, human albumin and fragments and analogs thereof reduce the risk of the fusion protein being immunogenic in humans. Human serum albumin (HSA) consists of a single non-glycosylated polypeptide chain of 585 amino acids with a formula molecular weight of 66,500. The amino acid sequence of human SA is provided below. (See also Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747). A variety of polymorphic variants as well as analogs and fragments of albumin have been described. (See Weitkamp, et al., (1973) Ann. Hum. Genet. 37:219). For example, EP322094 disclose shorter forms of HSA. Thus in some embodiments the albumin comprises any of fragments HSA(1-373), HSA(1-388), HSA(1-389), HSA(1-369), and HSA(1 5 419) and fragments between 1-369 and 1-419. EP 399666 discloses albumin fragments that include HSA(1-177) and HSA(1-200) and fragments between HSA(1-177) and HSA(1-200). It is understood that the heterologous fusion protein is biologically active and has a longer plasma half-life than the unconjugated drug compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the drug compound of interest.

Specific examples of heterologous fusion proteins having biological activity and increased half-life are Val8-GLP-1-HSA, Val8-GLP-1-[Gly-Gly-Gly-Gly-Ser]3-HSA peptide disclosed as SEQ ID NO: 38, Exendin-4-HSA and Exendin-4-[Gly-Gly-Gly-Gly-Ser]3-HSA (peptide disclosed as SEQ ID NO: 38). Further examples are Val8-GLP-1-CEX-IgG1, Val8-Glu9-GLP-1-CEx-IgG1, Exendin-4-C2-IgG1, Exendin-4-Linker-IgG1, Gly-Glu-GLP-1-CEx-Linker-HSA, Gly-Glu-GLP-1-CEx-Linker-IgG4. CEx refers to a C-terminal extension and comprises the sequence of Ser-Ser-Gly-Ala-Pro-Pro-Pro-Ser (SEQ ID NO: 43). Linker in the above conjugates is Gly-Gly-Gly-Gly-Ser-Gly-Gly-Gly-Gly-Ser-Gly-Gly Gly-Gly-Ser (SEQ ID NO: 38); C2 is Ser-Ser-Gly-Ala-Ser-Ser-Gly-Ala (SEQ ID NO: 44). The amino acid sequences of these fusion proteins and their components (e.g. HAS) are: Val8-GLP-1-Human serum albumin amino acid sequence (SEQ ID NO: 5), Val-GLP-1-Linker-Human serum albumin amino acid sequence (SEQ ID NO: 6), Gly-Glu-GLP-1-CEx-Linker-Human serum albumin amino acid sequence (SEQ ID NO: 7), Exendin-4-Human serum albumin amino acid sequence (SEQ ID NO: 8), Val8-GLP-1-IgG1 amino acid sequence (SEQ ID NO: 9), Val-GLP-1-Cex-IgG1 amino acid sequence (SEQ ID NO: 10), and Exendin-4-C2-IgG1 amino acid sequence (SEQ ID NO: 11), In further embodiments, the Fc analogs and fusions contemplated herein in the practice of the methods described herein include without limitation those Fc variants and fusion proteins described in Published Application WO 2004/110472, filed Jun. 10, 2004, entitled "Fusion Proteins," which application is herein incorporated by reference in its entirety and for all purposes, including for its specific Fc sequences and linkers. As noted above, the Fc can contain substituted amino acids at various positions that lessen or eliminate effecter function and/or do not have glycosylation sites and thus have reduced heterogeneity during expression. Furthermore, the substitutions can be those that do not induce an immune response after repeated and prolonged administration of the heterologous fusion protein. The heterologous fusion proteins can contain an Fc portion which is derived from human IgG4, but comprises one or more substitutions compared to the wild-type human sequence. The IgG4 Fc portion of the heterologous fusion proteins may contain one or more of the following substitutions: substitution of proline for glutamate at residue 233, alanine or valine for phenylalanine at residue 234 and; alanine or glutamate for leucine at residue 235 (KU numbering, Kabat, E. A. et al. (1991) Sequences of Proteins of Immunological Interest, 5th Ed. U.S. Dept. of Health and Human Services, Bethesda, Md., NIH Publication no. 91-3242). These residues corresponds to positions 16, 17 and 18 in the Fc formula provided below. Further, removing the N-linked glycosylation site in the IgG4 Fc region by substituting Ala for Asn at residue 297 (KU numbering) which corresponds to position 80 of the Fc formula is another way to ensure that residual effecter activity is eliminated in the context of a heterologous fusion protein. In addition, the IgG4 Fc portion of the heterologous fusion proteins can contain a substitution that stabilizes heavy chain dimer formation and prevents the formation of half-IgG4 Fc chains. The heterologous fusion proteins can exist as dimers joined together by disulfide bonds and various non-covalent interactions. Wild-type IgG4 contains a Pro-Pro-Cys-Pro-Ser-Cys (SEQ ID NO: 45) motif beginning at residue 224 (KU numbering). This motif in a single active therapeutic peptide-Fc chain forms disulfide bonds with the corresponding motif in another active therapeutic to peptide-Fc chain. However, the presence of serine in the motif causes the formation of single chain heterologous fusion proteins. Accordingly, the IgG4 sequence in yet a further embodiment can be modified such that serine at position at 228 (KU numbering) is substituted with proline (amino acid residue 11 in the FC formula below). The C-terminal lysine residue present in the native molecule may be deleted in the IgG4 derivative Fc portion of the heterologous fusion proteins (position 230 of the Fc formula; deleted lysine referred to as des K). Heterologous fusion proteins expressed in some cell types wherein lysine is encoded by the C-terminal codon are heterogeneous in that a portion of the molecules have lysine as the C-terminal amino acid and a portion have lysine deleted. The deletion is due to protease action during expression in some types of mammalian cells. Thus, to avoid this heterogeneity, a heterologous fusion expression constructs can lack a C-terminal codon for lysine.

In vivo function and stability of any of the heterologous fusion proteins described herein can be optimized by adding small peptide linkers to prevent potentially unwanted domain interactions. Further, a glycine rich linker provides some structural flexibility such that the active therapeutic peptide portion can interact productively with its receptor on target cells. These linkers, however, can significantly increase the risk that the heterologous fusion protein will be immunogenic in vivo. Thus, in one embodiment the linker length is no longer than necessary to prevent unwanted domain interactions and/or optimize biological activity and/or stability.

Fc sequences with such properties as described above for use in the heterologous fusion proteins described herein can comprise the formula (SEQ ID NO: 46):

Xaa$^1$-Glu-Ser-Lys-Tyr-Gly-Pro-Pro-Cys-Pro-Pro-Cys-Pro-Ala-Pro Xaa$^{16}$-Xaa$^{17}$-Xaa$^{18}$-

Gly-Gly-Pro-Ser-Val-Phe-Leu-Phe-Pro-Pro-Lys-Pro Lys-Asp-Thr-Leu-Met-Ile-Ser-Arg-

-continued

```
Thr-Pro-Glu-Val-Thr-Cys-Val Val-Val-Asp-Val-Ser-Gln-Glu-Asp-Pro-Glu-Val-Gln-

Phe-Asn-Trp Tyr-Val-Asp-Gly-Val-Glu-Val-His-Asn-Ala-Lys-Thr-Lys-Pro-Arg Glu-

Glu-Gln-Phe-Xaa⁸⁰-Ser-Thr-Tyr-Arg-Val-Val-Ser-Val-Leu-Thr-Val-Leu-His-Gln-Asp-

Trp-Leu-Asn-Gly-Lys-Glu-Tyr-Lys-Cys-Lys Val-Ser-Asn-Lys-Gly-Leu-Pro-Ser-Ser-Ile-

Glu-Lys-Thr-Ile-Ser Lys-Ala-Lys-Gly-Gln-Pro-Arg-Glu-Pro-Gln-Val-Tyr-Thr-Leu-Pro

Pro-Ser-Gln-Glu-Glu-Met-Thr-Lys-Asn-Gln-Val-Ser-Leu-Thr-Cys Leu-Val-Lys-Gly-

Phe-Tyr-Pro-Ser-Asp-Ile-Ala-Val-Glu-Trp-Glu Ser-Asn-Gly-Gln-Pro-Glu-Asn-Asn-Tyr-

Lys-Thr-Thr-Pro-Pro-Val Leu-Asp-Ser-Asp-Gly-Ser-Phe-Phe-Leu-Tyr-Ser-Arg-Leu-

Thr-Val Asp-Lys-Ser-Arg-Trp-Gln-Glu-Gly-Asn-Val-Phe-Ser-Cys-Ser-Val Met-His-

Glu-Ala-Leu-His-Asn-His-Tyr-Thr-Gln-Lys-Ser-Leu-Ser-Leu-Ser-Leu-Gly-Xaa²³⁰,
``` wherein Xaa at position 1 is Ala or absent; Xaa at position 16 is Pro or Glu; Xaa at position 17 is Phe, Val, or Ala; Xaa at position 18 is Leu, Glu, or Ala; Xaa at position 80 is Asn or Ala; and; Xaa at position 230 is Lys or is absent.

In one embodiment GLP-1-Fc fusions include the following proteins: Gly8-Glu22-Gly36-GLP-1(7-37)-1L-IgG4 (S228P), Gly8-Glu22-Gly36-GLP-1(7-37)-1L-IgG4 (S228P, F234A, L235A), Gly8-Glu22-Gly36-GLP-1(7-37)-1 L-IgG4 (S228P, N297A), Gly8-Glu22-Gly36-GLP-i(7-37)-1L-IgG4 (S228P, F234A, L235A, N297A), Gly8-Glu22-Gly36-GLP-1(7-37)-i.5L-IgG4 (S228P), Gly8-Glu22-Gly36-GLP-i(7-37)-1.5L-IgG4 (S228P, F234A, L235A), Gly8-Glu22-Glu36-GLP-1(7-37)-1. 5L-IgG4 (S228P, N297A), Gly8-Glu22-Gly36-GLP-1(7-37)-1.5L-IgG4 (S228P, F234A, L235A, N297A), Gly8-Glu22-Gly36-GLP-i(7-37)-2L-IgG4 (S228P), Gly8-Glu22-Gly36-GLP-i(7-37)-2L-IgG4 (S228P, F234A, L235A), Gly8-Glu22-Gly36-GLP-i (7-37)-2L-IgG4 (S228P, N297A), and Gly8-Glu22-Gly36-GLP-i (7-37)-2L-IgG4 (S228P, F234A, L235A, N297A), and the Val8 and des-K forms of all of the above. The nomenclature used herein to refer to specific fusion proteins is defined as follows: Specific substitutions to the GLP-1 portion of the fusion protein are indicated using the specific amino acid being substituted followed by the residue number. GLP-1(7-37) indicates that the GLP-1 portion of the mature fusion protein begins with His at position 7 and ends with Gly at position 37. L refers to a linker with the sequence Gly-Gly-Gly-Gly-Ser-Gly-Gly-Gly-Gly-Ser-Gly-Gly-Gly-Gly-Ser (SEQ ID NO: 38). The number immediately preceding the L refers to the number of linkers separating the GLPL 1 portion from the Fc portion. A linker specified as 1.5L refers to the sequence Gly-Ser-Gly-Gly-Gly-Gly-Ser-Gly-Gly-Gly-Gly-Ser-Gly-Gly-Gly-Gly-Ser-Gly-Gly-Gly-Gly-Ser (SEQ ID NO: 39). IgG4 refers to an analog of the human IgG4 Fc sequence specified shown in the above published application as SEQ ID NO. 7. Substitutions in the IgG4 Fc portion of the fusion protein are indicated in parenthesis. The wild-type amino acid is specified by its common abbreviation followed by the position number in the context of the entire IgG4 sequence using the EU numbering system followed by the amino acid being substituted at that position specified by its common abbreviation.

In some embodiments, exendin and exendin agonist and GLP-1 receptor agonist heterologous fusion compounds contemplated in the practice of the methods as described herein include without limitation those prepared as in or described in Published Application WO 2006/068910, filed Dec. 15, 2005, entitled "GLP 1 Analog Fusion Protein Formulations," which application is herein incorporated by reference in its entirety and for all purposes, including the formulations of Fc containing fusions. As described herein are a more stable solution formulation for heterologous fusions of an Fc macromolecule and an exendin, exendin agonist or GLP-1 receptor agonist described herein. A formulation comprising a therapeutically effective amount of an Fc fusion at a pH between about pH 6 and about pH 8.5, between about pH 6 and about pH 7.5, between about pH 6 and about pH 7, between about pH 6.5 and about pH 7.5, or between about pH 6 and about pH 6.5, and even further about pH 6 or about 6.5, provide greater chemical stability than when compared to an Fc fusion at a pH outside the described ranges. The pH of the Fc fusion formulations is adjusted to provide acceptable stability, to maintain the solubility and bioactivity of the exendin, exendin agonist or GLP-1 receptor agonist Fc-conjugate and be acceptable for parenteral administration. In one embodiment, the pH of the fusion formulation can be adjusted to between about pH 6 and about pH 8.5, between about pH 6 and about pH 7.5, between about pH 6 and about pH 7, between about pH 6.5 and about pH 7.5, or between about pH 6 and about pH 6.5, and in yet further, about pH 6 or about 6.5. The formulations comprising an Fc fusion may optionally encompass a pharmaceutically acceptable buffer. However, the selection and concentration of the buffer shall be such that the formulation can be adjusted to the described ranges that provide acceptable stability and bioactivity. Examples of pharmaceutically acceptable buffers for the Fc fusions include phosphate buffers like dibasic sodium phosphate, TRIS, acetate, such as sodium acetate, citrate, such as sodium citrate, sodium tartarate, basic amino acids such as histidine, lysine or arginine, or neutral amino acids such as glycine and glycyl-glycine. Other pharmaceutically acceptable buffers are known in the art. In a further embodiment the buffer is selected from the group consisting of citrate, phosphate and TRIS. The skilled artisan will recognize that the selection of the buffer is dependent upon the described pH ranges and the pKa of the buffer. In one embodiment, the concentration of a buffer is between about 1 mM and 30 mM. Yet further the concentration is between about 4 mM and 14 mM or between about 5 mM and 20 mM. Yet further the concentration is between about 10 mM and 20 mM. Even further the concentration is about 10 mM or about 20 mM. The Fc fusion formulations may optionally encompass a preservative. However, the selection and concentration of the preservative shall be such that the formulation can be adjusted to the described ranges that provide acceptable stability and bioactivity. Among preservatives known in the art as being effective and acceptable in parenteral formulations are phenolic preservatives, alkylparabens, benzyl alcohol, chlorobutanol, resorcinol, and other similar preservatives, and various mixtures thereof. Examples of phenolic derivatives include cresols and phenol or a mixture of cresols and phenol. Examples of cresols include meta-cresol, ortho-cresol, para-cresol, chloro-cresol, or mixtures thereof. Alkylparaben refers to a C1 to C4 alkyl paraben, or mixtures thereof. Examples of alkylparabens include methylparaben, ethylparaben, propylparaben, or butylparaben. The concentration of the preservative is known to one skilled in the art. The concentrations must be sufficient to maintain preservative effectiveness by retarding microbial growth. In one embodiment the preservative is meta-cresol or phenol. In general, the concentration of meta-cresol is between about 2.0 to about 8.0 mg/mL, about 2.5 mg/mL to about 4.5 mg/mL, and about 2.0 mg/mL to about 4.0 mg/mL. Further, the concentration of preservative in the Fc formulation is about 2.7 mg/mL. In another embodiment, the concentration of phenol is between about 2.0 to about 10.0 mg/mL, and about 4.0 to about 8.0 mg/mL. Even further the preservative in the formulation is about 5.0 mg/mL. The Fc fusion formulations may optionally encompass an isotonicity agent. However, the selection and concentration of the isotonicity agent shall be such that the formulation can be adjusted to the described ranges that provide acceptable stability and bioactivity. Isotonicity agents refer to compounds that are tolerated physiologically and impart a suitable tonicity to the formulation to prevent the net flow of water across cell membranes. Examples of such compounds include glycerin (or glycerol), salts, e.g., NaCl, and sugars, e.g., dextrose, mannitol, and sucrose. These compounds are commonly used for such purposes at known concentrations. One or more isotonicity agents may be added to adjust the ionic strength or tonicity. In one embodiment the isotonicity agent is NaCl. The concentration of NaCl can be between about 10 mM and 500 mM, between about 50 mM and 200 mM, and even further is about 150 mM. In another embodiment, the isotonicity agent is mannitol. The concentration of the mannitol can be between about 1% (weight (w)/volume (v)) and 10% (w/v), and further is between about 2% (w/v) and 8% (w/v). In another embodiment, the isotonicity agent is glycerin. The concentration of the glycerin can be between about 12 mg/mL and 25 mg/mL, between about 12 mg/mL and 20 mg/mL, and further is about 17 mg/ml. The formulations may optionally encompass a solubility enhancer. However, the selection and concentration of the solubility enhancer shall be such that the Fc fusion formulation can be adjusted to the described ranges that provide acceptable stability and bioactivity. Solubility enhancers provide stability such that the Fc fusion remains soluble for an extended period of time under the conditions of storage. In one embodiment the solubility enhancer is nicotinamide. In general, the concentration of nicotinamide is between 0.01 and 2 molar. Other ranges of nicotinamide concentration are: between 0.05 molar and 1.5 molar; between 0.1 molar and 1.0 molar; between 0.1 molar and 0.5 molar; between 0.5 molar and 1.0 molar; and between 0.15 molar and 0.25 molar. Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) may optionally be added to the formulation. In one embodiment the solubilizer is Tween 20® or Tween80®. In general, the concentration of Tween 20® or Tween8O® is between 0.001% and 0.05%, between 0.005% and 0.05%; between 0.0075% and 0.05%; and between 0.01% and 0.05%.

Accordingly, a stable solution Fc formulation can comprise a therapeutically effective amount of an exendin-, exendin agonist- or a GLP-1 receptor agonist-Fc fusion at a pH of between about pH 6 and about pH 8.5 wherein the Fc fusion comprises an Fc portion of an immunoglobulin comprising the sequence (SEQ ID NO: 47):

```
Ala-Glu-Ser-Lys-Tyr-Gly-Pro-Pro-Cys-Pro-Pro-Cys-Pro-Ala-Pro-Xaa16-Xaa17-Xaa18-
Gly-Gly-Pro-Ser-Val-Phe-Leu-Phe-Pro-Pro-Lys-Pro-Lys-Asp-Thr-Leu-Met-Ile-Ser-Arg-
Thr-Pro-Glu-Val-Thr-Cys-Val-Val-Val-Asp-Val-Ser-Gln-Glu-Asp-Pro-Glu-Val-Gln-
Phe-Asn-Trp-Tyr-Val-Asp-Gly-Val-Glu-Val-His-Asn-Ala-Lys-Thr-Lys-Pro-Arg-Glu-
Glu-Gln-Phe-Xaa80-Ser-Thr-Tyr-Arg-Val-Val-Ser-Val-Leu-Thr-Val-Leu-His-Gln-Asp-
Trp-Leu-Asn-Gly-Lys-Glu-Tyr-Lys-Cys-Lys-Val-Ser-Asn-Lys-Gly-Leu-Pro-Ser-Ser-
Ile-Glu-Lys-Thr-Ile-Ser-Lys-Ala-Lys-Gly-Gln-Pro-Arg-GIu-Pro-Gln-Val-Tyr-Thr-Leu-
Pro-Pro-Ser-Gln-Glu-Glu-Met-Thr-Lys-Asn-Gln-Val-Ser-Leu-Thr-Cys-Leu-Val-Lys-
Gly-Phe-Tyr-Pro-Ser-Asp-Ile-Ala-Val-Glu-Trp-Glu-Ser-Asn-Gly-Gln-Pro-Glu-Asn-
Asn-Tyr-Lys-Thr-Thr-Pro-Pro-Val-Leu-Asp-Ser-Asp-Gly-Ser-Phe-Phe-Leu-Tyr-Ser-
Arg-Leu-Thr-Val-Asp-Lys-Ser-Arg-Trp-Gln-Glu-Gly-Asn-Val-Phe-Ser-Cys-Ser-Val-
Met-His-Glu-Ala-Leu-His-Asn-His-Tyr-Thr-Gln-Lys-Ser-Leu-Ser-Leu-Ser-Leu-Gly-
Xaa230,
``` wherein Xaa at position 16 is Pro or Glu; Xaa at position 17 is Phe, Val, or Ala; Xaa at position 18 is Leu, Glu, or Ala; Xaa at position 80 is Asn or Ala; and Xaa at position 230 is Lys or is absent. Even further the stable solution Fc formulation is between about pH 6 and about pH 7.5. Yet further the stable solution Fc formulation is between about pH 6 and about pH 7, is between about pH 6 and about pH 6.5, is about pH 6 or is about pH 6.5. In one embodiment the Fc formulation further comprises Tween 20® and/or Tween 80, and NaCl, and m-Cresol.

In a further embodiment the compound fused to the Fc, optionally via linker, comprises a GLP-1 analog comprising a sequence selected from the group consisting of:
a)     His-Xaa$^8$-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp- Leu-Val-Lys-Gly-Gly-Gly (SEQ ID NO: 48) wherein Xaa⁸ is selected from Gly and Val;
b) His-Xaa⁸-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Lys-Asn-Gly-Gly-Gly (SEQ ID NO: 49) wherein Xaa⁸ is selected from Gly and Val;
c) His-Xaa⁸-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly-Pro (SEQ ID NO: 50) wherein Xaa⁸ is selected from Gly and Val;
d) His-Xaa⁸-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Lys-Asn-Gly-Gly-Pro (SEQ ID NO: 51) wherein Xaa⁸ is selected from Gly and Val;
e) His-Xaa⁸-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Gly (SEQ ID NO: 52) wherein Xaa⁸ is selected from Gly and Val; and
f) His-Xaa⁸-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Lys-Asn-Gly-Gly (SEQ ID NO: 53) wherein Xaa⁸ is selected from Gly and Val.

Definitions

In accordance with the present invention and as used herein, the following terms are defined to have the following meanings, unless explicitly stated otherwise.

The term amino acid refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic, acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "proteogenic amino acid" refers to alanine, arginine, asparagine, aspartic acid, cysteine, cystine, glutamine, glutamic acid, glycine, histidine, hydroxyproline, isoleucine, leucine, lysine, methionine, phenylalanine, proline, serine, threonine, tryptophan, tyrosine, or valine. The term "non-proteogenic amino acid" refers to an amino acid which can be incorporated into a peptide via peptide bonds but is not a proteogenic amino acid; examples are, without limitation, γ-carboxyglutamate, ornithine, phosphoserine, the D-amino acids (e.g., D-alanine, D-glutamine and the like), Aib (α-aminoisobutyric acid), Abu (α-aminobutyric acid), Tie (tert-butylglycine), 3-aminomethyl benzoic acid, anthranilic acid, des-amino-Histidine, the beta analogs of amino acids (e.g., β-alanine and the like), D-histidine, 2-amino-histidine, β-hydroxy-histidine, homohistidine, Nᵅ-acetyl-histidine, α-fluoromethyl-histidine, α-methyl-histidine, 3-pyridylalanine, 2-pyridylalanine, 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, (1-aminocyclooctyl) carboxylic acid, and the like. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term amino acid analog refers to an amino acid wherein either the C-terminal carboxy group, the N-terminal amino group or side-chain functional group has been chemically modified to another functional group. For example, aspartic acid-(β-methyl ester) is an amino acid analog of aspartic acid; N-ethylglycine is an amino acid analog of glycine; or alanine carboxamide is an amino acid analog of alanine.

The term amino acid residue refers to radicals having the structure: (1) —C(O)—R—NH—, wherein R typically is —CH(R')—, wherein R' is an amino acid side chain, typically H or a carbon containing substituent; or (2)

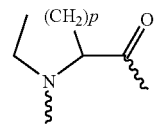

wherein p is 1, 2 or 3 representing the azetidinecarboxylic acid, proline or pipecolic acid residues, respectively.

The term lower referred to herein in connection with organic radicals such as alkyl groups defines such groups with up to and including about 6, up to and including 4 and advantageously one or two carbon atoms. Such groups may be straight chain or branched chain.

Pharmaceutically acceptable salt includes salts of the compounds described herein derived from the combination of such compounds and an organic or inorganic acid. In practice, the use of the salt form amounts to use of the base form. The compounds are useful in both free base and salt form.

The terms "therapeutically effective," "therapeutically effective amount," "effective amount" and the like indicate that the materials or amount of material is effective to prevent, alleviate, or ameliorate one or more symptoms of a disease or medical condition, and/or to prolong the survival of the subject being treated.

In addition, the following abbreviations are as defined: "ACN" or "CH₃CN" refers to acetonitrile; "Boc", "tBoc" or "Tboc" refers to t-butoxy carbonyl; "DCC" refers to N,N'-dicyclohexylcarbodiimide; "Fmoc" refers to fluorenylmethoxycarbonyl; "HBTU" refers to 2-(1H-benzotriazol-1-yl)-1,1,3,3,-tetramethyluronium hexafluorophosphate; "HOBt" refers to 1-hydroxybenzotriazole monohydrate; "homoP" or hpro" refers to homoproline; "MeAla" or "Nme" refers to N-methylalanine; "naph" refers to naphthylalanine; "pG" or "pGly" refers to pentylglycine; "tBuG" refers to tertiary-butylglycine; "ThioP" or "tPro" refers to thioproline; "3Hyp" refers to 3-hydroxyproline; "4Hyp" refers to 4-hydroxyproline; NAG" refers to N-alkylglycine; NAPG" refers to N-alkylpentylglycine; "Norval" refers to norvaline; and "Norleu" refers to norleucine.

Preparation of Compounds

The exendins, exendin agonists and GLP-1 receptor agonists described herein may be prepared using standard solid-phase peptide synthesis techniques and preferably an automated or semiautomated peptide synthesizer. The exendins, exendin agonists and GLP-1 receptor agonists may be prepared using any method known by one skilled in the art, including those described in U.S. application Ser. No, 09/756, 690, "Use of Exendins and Agonists Thereof For Modulation of Triglyceride Levels and Treatment of Dyslipidemia" which was filed Jan. 9, 2001, and which is herein incorporated by reference in its entirety and for all purposes. In one embodiment, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives, and 4-methylbenzhydryl-amine resin used in the peptide synthesizer may be purchased from for example Applied Biosystems Inc. (Foster City, Calif.). The following side-chain protected amino acids may be purchased from Applied Biosystems, Inc.: Boc-Arg (Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His(Trt), Fmoc-Asn(Trt), and Fmoc-Gln (Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6-12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10µ, 2.2×25 cm; Vydac, Hesperia, Calif.) may be used to isolate peptides, and purity may be determined using a C4, C8 or C18 analytical column (5µ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., *The Pico Tag Method: A Manual of Advanced Techniques for Amino Acid Analysis*, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried out on a VG-Trio machine.

Peptide compounds useful in the methods described herein may also be prepared using recombinant DNA techniques, using methods known in the art. See, e.g., Sambrook et al., *Molecular Cloning: A Laboratory Manual*, 2d Ed., Cold Spring Harbor (1989). Non-peptide compounds useful for the methods described herein may be prepared by art-known methods. For example, phosphate-containing amino acids and peptides containing such amino acids may be prepared using methods known in the art. See, e.g., Bartlett and Landen, *Biorg. Chem.* 14:356-377(1986).

In certain embodiments, methods described herein comprise administering to a subject one or more exendin, exendin agonist or GLP-1 receptor agonist. In certain embodiments, methods described herein comprise administering to a subject in need of treatment one or more exendin, exendin agonist or GLP-1 receptor agonist. For administration, compositions useful in the methods described herein may conveniently be provided in the form of formulations suitable for parenteral (including intravenous, intramuscular, and subcutaneous), nasal, bucal or oral administration. In some cases, it will be convenient to provide an exendin, exendin agonist or GLP-1 receptor agonist and a therapeutically effective amount of another lipid-controlling agent, for example without limitation a statin, in a single composition or solution for administration together. In other cases, it may be more advantageous to administer the additional agent separately from said exendin, exendin agonist or GLP-1 receptor agonist. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2 S (1988).

Compounds useful in the methods described herein can be provided as parenteral compositions for injection or infusion. Exemplary formulations are those described and claimed in U.S. application Ser. No. 60/116,380, "Novel Exendin Agonist Formulations and Methods of Administration Thereof," which was filed on Jan. 14, 1999 and published as U.S. Patent Publication 20030087820 A1 on May 8, 2003, both of which are herein incorporated by reference in their entireties and for all purposes.

Formulations include, for example, compounds suspended in an inert oil, suitably a vegetable oil such as sesame, peanut, olive oil, or other acceptable carrier. In one embodiment, they are suspended in an aqueous carrier, for example, in an isotonic buffer solution at a pH of about 3.0 to about 8.0, in one embodiment, at a pH of about 3.5 to about 5.0. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. Formulations may also include a preservative. An exemplary preservative is m-cresol, for example, 0.3% m-cresol. A form of repository or "depot" slow release preparation may be used so that therapeutically effective amounts of the preparation are delivered into the bloodstream over many hours or days following transdermal injection or delivery.

In certain embodiments of any of the methods described herein, the peptide or analog thereof can be administered in a polymer-based sustained release device. Such polymer-based sustained release devices are described, for example, in Published Application WO2005/102293A1 and U.S. Patent Publication 2005/0271702, for example, which are incorporated herein by reference in their entireties and for all purposes. Accordingly, in one embodiment, the exendin, exendin agonist and GLP-1 receptor agonist, which are biologically active polypeptides, can be formulated as a composition for the sustained release of the biologically active polypeptide comprising a biocompatible polymer, the biologically active polypeptide and a sugar, wherein the ratio of serum $C_{max}$ to $C_{ave}$ is about 3 or less, which avoids an undesirable initial release of peptide after injection that leads to nausea in the subject. In certain embodiments, the sustained release composition comprises the polypeptide from about 0.1% w/w to about 10% w/w of the total weight of the sustained release composition. In certain embodiments, the sustained release composition comprises the polypeptide from about 0.5% w/w to about 5% w/w of the total weight of the sustained release composition. The sustained release composition can comprise a total pore volume of the composition from about 0.1 mL/g or less as determined using mercury intrusion porosimetry, as known in the art.

The sustained release composition can comprise the sugar present from about 0.01% w/w to about 10% w/w of the total weight of the sustained release composition. The sugar can be present from about 0.1% w/w to about 5% w/w of the total weight of the sustained release composition. The sugar can be selected from a monosaccharide, a disaccharide, a sugar alcohol or a combination thereof. In certain embodiments, the sugar is selected from sucrose, mannitol and combinations thereof. The biocompatible polymer can be selected from the group consisting of poly(lactides), poly(glycolides), poly(lactide-co-glycolides), poly(lactic acids), poly(glycolic acids), poly(lactic acid co-glycolic acids), polycaprolactone, polycarbonates, polyesteramides, polyanhydrides, poly(amino acids), polyorthoesters, polycyanoacrylates, poly(p dioxanone), poly(alkylene oxalate)s, biodegradable polyurethanes, blends thereof and copolymers thereof. In further embodiments the polymer comprises poly(lactide-co-glycolide), and further can be a 50:50 poly(lactide-co-glycolide). In certain embodiments the sustained release composition comprises, or in other embodiments consists essentially of, a biocompatible polymer having dispersed therein an exendin, exendin agonist or a GLP-1 receptor agonist, or can be exendin-4, at about 3% w/w or more and sucrose at about 2% w/w or more of the weight of the composition. In such embodiments the biocompatible polymer can be without limitation a poly(lactide-co-glycolide), and further the ratio of serum $C_{max}$ to $C_{ave}$ is about 3 or less, and the total pore volume of the composition is about 0.1 mL/g or less as determined using mercury intrusion porosimetry, as known in the art. Accordingly, in certain embodiments of the methods described herein there is provided a composition for the sustained release of the biologically active polypeptide comprising a 50:50 DL PLG 4A polymer, about 3 to 5% (w/w) exendin-4, and about 2% (w/w) sucrose, wherein the ratio of serum $C_{max}$ to $C_{ave}$ is about 3 or less and the total pore volume of the composition is about 0.1 mL/g or less. An injectable composition suitable for passage through a 25 gauge needle can comprise a sustained release composition comprising a 50:50 DL PLG 4A polymer, about 3 to 5% (w/w) exendin-4, and about 2% (w/w) sucrose, wherein the ratio of serum $C_{max}$ to $C_{ave}$ is about 3 or less and the total pore volume of the composition is about 0.1 mL/g or less, suspended in an injection vehicle comprising sodium carboxymethylcellulose at 3.0% (w/v), sodium chloride at 0.9% (w/v), and Polysorbate 20, NF (Tween 20) at 0.1% (v/v) in water.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride can be used when buffers containing sodium ions is desired.

Compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Acetate salts are a further embodiment. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical compositions can be administered by different routes including intravenously, intraperitoneal, subcutaneous, and intramuscular, orally, topically, transmucosally, or by pulmonary inhalation. Exemplary methods of administration are discussed herein as well as in U.S. Application No. 60/116,380, "Novel Exendin Agonist Formulations and Methods of Administration Thereof," which was filed on Jan. 14, 1999 and published as US patent publication 20030087820 A1 on May 8, 2003, both of which are herein incorporated by reference in their entirety and for all purposes. Suitable excipients may be carrier molecules that include large, slowly metabolized macromolecules such as proteins, polysaccharides, polylactic acids, polyglycolic acids, polymeric amino acids, amino acid copolymers, and inactive virus particles. Liposomes are also included within the definition of pharmaceutically acceptable excipients.

If desired, solutions of the above compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, eg., a Triton).

Compositions useful in the practice of the methods described herein are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an exendin, exendin agonist or GLP-1 receptor agonist, for example, exendin-3, and/or exendin-4, with or without another fibrinogen-lowering agent. The term "effective amount" refers to an amount of a pharmaceutical agent used to treat, ameliorate, prevent, or eliminate the identified condition (e.g., disease or disorder), or to exhibit a detectable therapeutic or preventative effect. The effect can be detected by, for example, chemical markers, antigen levels, or time to a measurable event, such as morbidity or mortality. Therapeutic effects include, for example, decreasing the concentration of fibrinogen, decreasing the risk of one or more cardiovascular diseases or conditions, treating one or more cardiovascular diseases or conditions or a combination thereof. Effective amounts for a given situation can be determined by routine experimentation that is within the skill and judgment of the clinician.

For an exendin, exendin agonist or GLP-1 receptor agonist, the effective fibrinogen reducing amount can be estimated initially for example, in animal models, such as rat or mouse models. An animal model may also be used to determine the appropriate concentration range and route of administration. Such information can then be used to determine useful doses and routes for administration in humans.

Efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are generally more effective. The data obtained from cell culture assays and animal studies may be used in formulating a range of dosage for human use. The dosage contained in such compositions can be within a range of circulating concentrations that include an $ED_{50}$ with little or no toxicity. The dosage may vary within this range depending upon the dosage form employed, sensitivity of the patient, and the route of administration.

In certain embodiments, therapeutically effective amounts of an exendin, exendin agonist or GLP-1 receptor agonist for use in treating a subject in need, such as, for example, a subject with an elevated fibrinogen concentration include those that lower fibrinogen concentration. As will be recognized by those in the field, an effective amount of therapeutic agent will vary with many factors including the age, weight and health of the patient, the nature and extent of the condition, the patient's physical condition, the blood fibrinogen concentration, the therapeutic or combination of therapeutics selected for administration and other factors.

The therapeutically effective daily plasma fibrinogen controlling dose of the compounds contemplated herein may typically be in the range of from about 0.5 µg to about 3 µg, about 20 µg to about 30 µg, about 0.5 µg to about 1 mg/day, about 1 µg to about 1 mg/day, and, more specifically, from about 1 µg to about 20 µg or from about 1 µg to about 500 µg/day for a 70 kg patient, administered in a single or divided doses. Still more specifically, the therapeutically effective daily plasma fibrinogen controlling dose of the compounds will typically be in the range of from about 1 µg to about 100 µg/day and, more specifically 1 µg to about 50 µg, about 1 µg to about 3 µg to about 20 µg to about 50 µg/day, for a 70 kg patient, administered in a single or divided doses. It is intended that the use of a 70 kg patient is for exemplary purposes and that the above doses can be converted to a per kg basis for administration to a patient having a body weight of greater than or less that 70 kg.

Various exemplary dosages are described in U.S. Application Ser. No. 60/116,380, entitled, "Novel Exendin Agonist Formulations and Methods of Administration Thereof," which was filed on Jan. 14, 1999 and published as US patent publication 20030087820 A1 on May 8, 2003, both of which are herein incorporated by reference in their entirety and for all purposes.

Exemplary doses for twice daily administration include about 0.01 to 0.3 µg per kilogram, about 0.01 to 0.05 µg per kilogram, and about 0.1 to 0.3 µg per kilogram. Other exemplary doses based upon patient weight for compounds having approximately the potency of exendin-4 range from 0.005 µg/kg per dose to about 0.2 µg/kg per dose. In a further embodiment, doses based upon patient weight for compounds having approximately the potency of exendin-4 range from 0.02 µg/kg per dose to about 0.1 µg/kg per dose. Yet further, doses based upon patient weight for compounds having approximately the potency of exendin-4 range from 0.05 µg/kg per dose to about 0.1 µg/kg per dose. These doses are administered from 1 to 4 times per day, or from 1 to 2 times per day.

In certain embodiments, one or more exendins, exendin agonists or GLP-1 receptor agonists may be administered as long-acting formulations, such as for example a formulation for once or twice weekly administration. Any long-acting formulation known to the skilled artisan may be administered. Exemplary, non-limiting long-acting formulations include those as provided in International Application Nos. PCT/US2004/011547, filed Apr. 15, 2004, and PCT/US2005/012989, filed Apr. 15, 2005 (WO2005102293), and corresponding U.S. Published Applications 20050271702 and 20050271702, each of which are herein incorporated by reference in their entireties. Doses of exendin, exendin agonist or GLP-1 receptor agonist will normally be less if given by continuous infusion.

The exact dose to be administered is determined by the attending clinician and is dependent upon where the particular compound lies within the above quoted range, as well as upon the age, weight and condition of the individual, and the mode of administration. Administration may begin upon diagnosis of a need, such as for example diagnosis of an elevated fibrinogen concentration and may continue until the desired fibrinogen concentration is reached or while the desired concentration is maintained.

With respect to the methods described herein, administration may be by injection, including intravenous, subcutaneous or intramuscular. Administration may also be by non-injectable routes, for example, via the respiratory tract, the mouth, and the gut. Orally active compounds may be taken orally, however dosages should be increased 5-10 fold. Solid dosage forms, such as those useful for oral, buccal, sublingual, intra-tracheal, nasal or pulmonary delivery may be used. Additionally, preserved or unpreserved liquid formulations or dry powder may be used.

The optimal formulation and mode of administration of compounds of the present application to a patient depend on factors known in the art such as the disease or disorder associated with elevated fibrinogen concentrations, the desired effect, and the type of patient. In certain embodiments, the exendin or exendin agonist or GLP-1 receptor agonist is administered independent of the timing of a meal or not for the purpose of controlling prandial, post-prandial or fasting blood glucose levels.

To assist in understanding the present invention, the following Examples are included. The experiments relating to this invention should not, of course, be construed as limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. Those of skill in the art will understand that the techniques described in these examples represent techniques described by the inventors to function well in the practice of the invention, and as such constitute exemplary modes for the practice thereof. However, those of skill in the art should appreciate that, in light of the present disclosure, many changes can be made in the specific methods that are disclosed and still obtain a like or similar result without departing from the spirit and scope of the invention.

Example 1

Administration of Exendin

Fifty two patients participated in a test meal study which was part of a 1-year, 13-country, open-label trial comparing exenatide (exendin-4) and biphasic insulin aspart 30/70 (n=505). Patients with type 2 diabetes inadequately controlled by sulphonylurea and metformin are randomized to exenatide (n=30) or biphasic insulin aspart (n=22). For test meal data, postprandial glucose incremental $AUC_{0-4h}$ is calculated at baseline and week 52. Patients received 5 µg of exenatide BID for a 4-week treatment initiation period, followed by 48 weeks of exenatide therapy at 10 µg BID.

Traditional and nontraditional cardiovascular (CV) markers, including precursor brain natriuretic protein, oxidized LDL-C, highly sensitive C-reactive protein, and apolipoproteins A1 and B, are measured during the fasting state using standard assays.

Changes in lipoprotein particle size and concentration from baseline to endpoint are shown in Table 1.

TABLE 1

|  | Exenatide Δ mean (SEM) | Insulin Δ mean (SEM) | Between-Group Difference |
|---|---|---|---|
| LDL Particle Size (nm) | +0.33 (0.10) p = .001 | +0.11 (0.12) p = .356 | p = .144 |
| HDL Particle Size (nm) | +0.11 (0.04) p = .013 | +0.04 (0.05) p = .391 | p = .318 |
| VLDL Particle Size (nm) | −3.2 (1.9) p = .097 | −1.6 (2.2) p = .482 | p = .590 |
| Total LDL (nmol/L) | −87.3 (62.2) p = .169 | +5.0 (75) p = .947 | p = .348 |
| Large LDL (nmol/L) | +68.4 (27.3) p = .017 | +37.7 (32.8) p = .258 | p = .479 |
| Small LDL (nmol/L) | −146.4 (67.7) p = .037 | −25.8 (81.2) p = .753 | p = .262 |
| Very Small LDL (nmol/L) | −126.8 (53.9) p = .024 | −17.0 (64.6) p = .794 | p = .201 |
| Total HDL (µmol/L) | +0.33 (0.79) p = .678 | +2.5 (0.9) p = .012 | p = .088 |
| Large HDL (µmol/L) | +0.69 (0.33) p = .042 | +1.0 (0.4) p = .014 | p = .528 |
| Total VLDL (nmol/L) | −9.3 (5.5) p = .097 | +12.9 (6.6) p = .056 | p = .014 |
| Small VLDL (nmol/L) | −2.1 (3.4) p = .547 | +8.5 (4.2) p = .049 | p = .064 |

Example 2

Measurement of Lipoprotein Concentration and Particle Diameter

Lipoprotein subclass particle concentrations and average particle diameters are measured using proton nuclear magnetic resonance spectroscopy. See e.g., Festa et al., Nuclear Magnetic Resonance Lipoprotein Abnormalities in Prediabetic Subjects in the Insulin Resistance Artherosclerosis Study, *Circulation*, 111:3465-3472(2005).

The particle concentrations of different lipoprotein subclasses are obtained by measuring the amplitudes of the characteristic lipid methyl NMR signals. The signal amplitudes of various subclasses are extracted from the overall lipid methyl group signal with a spectral deconvolution algorithm (LipoScience, Inc.). See e.g., Festa. VLDL and LDL particle concentrations are given in nanomoles per liter. HDL particle concentrations are provided in micromoles per liter.

Average particle sizes (in nanometers diameter) are computed as the sum of the diameter of the particle subclass multiplied by the relative mass percentage of the subclass as estimated from the amplitude of its methyl NMR signal.

Particle concentrations and sizes are compared before and after administration of an exendin or exendin agonist. See e.g., Table 1.

Example 3

Measurement of Fibrinogen Concentration

Fibrinogen activity is measured by the von Clauss clotting method. By the von Clauss clotting method, thrombin is added to a test sample and the time until clotting is measured. Fibrinogen concentration is determined by comparing clotting time for the test sample to the clotting time of a standard curve for various reference plasmas.

Fibrinogen is measured at baseline, Week 16, Week 52, or at early termination of the study.

Exemplary fibrinogen levels (g/L) are provided in Table 2.

TABLE 2

| Week | Exenatide | | | Insulin Aspart | | |
|---|---|---|---|---|---|---|
| | n | Mean | (SEM) | n | Mean | (SEM) |
| Baseline | 18 | 4.54 | (0.28) | 14 | 4.22 | (0.31) |
| Endpoint (LOCF) | 18 | 3.95 | (0.22) | 14 | 4.16 | (0.33) |

LOCF = last post-baseline measurement carried forward.

All patents and other references cited herein are indicative of the level of skill of those skilled in the art to which the references pertain, and are incorporated by reference in their entireties and for all purposes, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms to describe distinct subject matter. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

We claim:

1. A method for decreasing the concentration of fibrinogen in a subject in need thereof comprising administering to the subject a therapeutically effective amount a pharmaceutical composition comprising a glucagon-like peptide-1 (GLP-1) receptor agonist compound, wherein the GLP-1 receptor agonist compound is an exendin, an exendin analog, a GLP-1, or a GLP-1 analog.

2. The method of claim 1, wherein the pharmaceutical composition is administered parenterally, nasally, bucally, or orally.

3. The method of claim 1, wherein the pharmaceutical composition is administered by injection.

4. The method of claim 1, wherein the pharmaceutical composition is a sustained release pharmaceutical composition.

5. The method of claim 1, wherein the sustained release pharmaceutical composition comprises the GLP-1 receptor agonist compound, a biocompatible polymer, and a sugar.

6. The method of claim 1, wherein the GLP-1 receptor agonist compound is exendin-4.

7. The method of claim 1, wherein the GLP1 receptor agonist compound is conjugated to at least one macromolecule.

8. The method of claim 7, wherein the macromolecule is a peptide, a blood-protein-binding peptide, a hormone, a polypeptide, an albumin, a polyamino acid, a fatty acyl group, a diacid, a water soluble polymer, an immunoglobulin, an immunoglobulin fragment, a catalytic antibody, or a fragment of a catalytic antibody.

9. The method of claim 7, wherein the GLP-1 receptor agonist compound is conjugated to two macromolecules selected from the group consisting of a peptide, a blood-protein-binding peptide, a hormone, a polypeptide, an albumin, a polyamino acid, a fatty acyl group, a diacid, a water soluble polymer, an immunoglobulin, an immunoglobulin fragment, a catalytic antibody, and a catalytic antibody fragment.

10. The method of claim 1, wherein the GLP-1 receptor agonist compound is a compound of Formula, (I); a compound of Formula (II); a compound of Formula (III); a compound of Formula (IV); a compound of Formula (V); a compound of Formula (VI); a compound of Formula (VII); a compound of Formula (VIII); a compound of Formula (IX); a compound of Formula (X); a compound of Formula (XI); a compound of Formula (XII); exendin-3(SEQ ID NO:1); exendin-4(SEQ ID NO:2); exendin-4(1-30)(SEQ ID NO:54); exendin-4(1-27)(SEQ ID NO:55); exendin-4(1-28)(SEQ ID NO:56); $^{14}$Leu, $^{25}$Phe-exendin-4(SEQ ID NO:57); $^{14}$Leu-exendin-4(SEQ ID NO:58); $^{14}$Leu, $^{25}$Phe-exendin-4(1-28)(SEQ ID NO:59); $^{14}$Leu-exendin-4(1-28)(SEQ ID NO:60); [N$^\epsilon$-(17-carboxyheptadecanoic acid)Lys$^{20}$]exendin-4(1-39)amide(SEQ ID NO:61); [N$^\epsilon$-(17-carboxy-heptadecanoyl)Lys$^{32}$]exendin-4(1-39)amide(SEQ ID NO:62); exendin-4(1-39)-Lys$^{40}$($\epsilon$-(maleimidopropionic acid))-NH$_2$ (SEQ ID NO:63); exendin-4(1-39)-Lys$^{40}$($\epsilon$-((2-(2-amino)ethoxy acetic acid)-((2-(2-amino)ethoxy acetic acid)-(maleimidopropionic acid))-NH$_2$(SEQ ID NO:64); GLP-1(SEQ ID NO:3); GLP-1(7-37)(SEQ ID NO:65); or Arg$^{34}$Lys$^{26}$(N$^\epsilon$($\gamma$-glutamyl (N$^\alpha$-decanoyl)))GLP-1(7-37)(SEQ ID NO:66).

11. The method of claim 1, wherein the GLP-1 receptor agonist compound is complexed with a basic polypeptide.

12. The method of claim 1, wherein the GLP1 receptor agonist compound is complexed with a basic polypeptide selected from the group consisting of polylysine, polyarginine, polyornithine, protamine, putrescine, spermine, spermidine, and histone; and wherein the ratio of GLP-1 receptor agonist compound to basic polypeptide is between about 4:1 and about 10:1.

13. A method for treating an elevated level of fibrinogen in a subject in need thereof comprising administering to the subject a therapeutically effective amount a glucagon-like peptide-1 (GLP-1) receptor agonist compound, wherein the GLP-1 receptor agonist compound is an exendin, an exendin analog, a GLP-1, or a GLP-1 analog.

14. The method of claim 13, wherein the GLP-1 receptor agonist compound is a compound of Formula (I); a compound of Formula (II); a compound of Formula (III); a compound of Formula (IV); a compound of Formula (V); a compound of Formula (VI); a compound of Formula (VII); a compound of Formula (VIII); a compound of Formula (IX); a compound of Formula (X); a compound of Formula (XI); a compound of Formula (XII); exendin-3(SEQ ID NO:1); exendin-4(SEQ ID NO:2); exendin-4(1-30)(SEQ ID NO:54); exendin-4(1-27)(SEQ ID NO:55); exendin-4(1-28)(SEQ ID NO:56); $^{14}$Leu, $^{25}$Phe-exendin-4(SEQ ID NO:57); $^{14}$Leu-exendin-4(SEQ ID NO:58); $^{14}$Leu, $^{25}$Phe-exendin-4(1-28)(SEQ ID NO:59); $^{14}$Leu-exendin-4(1-28)(SEQ ID NO:60);
- [N$^\epsilon$-(17-carboxyheptadecanoic acid)Lys$^{20}$]exendin-4(1-39)amide (SEQ ID NO:61);
- [N$^\epsilon$-(17-carboxy-heptadecanoyl)Lys$^{32}$]exendin-4(1-39) amide (SEQ ID NO:62); exendin-4(1-39)-Lys$^{40}$($\epsilon$-(maleimidopropionic acid))-NH$_2$(SEQ ID NO:63); exendin-4(1-39)-Lys$^{40}$($\epsilon$-((2-(2-amino)ethoxy acetic acid)-((2-(2-amino)ethoxy acetic acid)-(maleimidopropionic acid))-NH$_2$(SEQ ID NO:64); GLP-1(SEQ ID NO:3); GLP-1(7-37)(SEQ ID NO:65); or Arg$^{34}$Lys$^{26}$(N$^\epsilon$($\gamma$-glutamyl(N$^\alpha$-decanoyl)))GLP-1(7-37)(SEQ ID NO:66).

15. A method for decreasing the concentration of fibrinogen in a subject in need thereof comprising administering to the subject a therapeutically effective amount of a particle comprising a glucagon-like peptide- 1 (GLP- 1) receptor agonist compound and a basic polypeptide, wherein the GLP-1 receptor agonist compound is an exendin, an exendin analog, a GLP-1, or a GLP-1 analog.

16. The method of claim 15, wherein the basic polypeptide is polylysine, polyarginine, polyornithine, protamine, putrescine, spermine, spermidine, or histone; and wherein the particle comprises the GLP-1 receptor agonist compound and the basic polypeptide in a ratio between about 4:1 and about 10:1; and the mean number diameter of the particle is between 1 μm and 5 μm.

17. The method of claim 15, wherein the GLP-1 receptor agonist compound is a compound of Formula (I); a compound of Formula (II); a compound of Formula (III); a compound of Formula (IV); a compound of Formula (V); a compound of Formula (VI); a compound of Formula (VII); a compound of Formula (VIII); a compound of Formula (IX); a compound of Formula (X); a compound of Formula (XI); a compound of Formula (XII); exendin-3(SEQ ID NO:1); exendin-4 (SEQ ID NO:2); exendin-4(1-30)(SEQ ID NO:54); exendin-4(1-27)(SEQ ID NO:55); exendin-4(1-28)(SEQ ID NO:56); $^{14}$Leu, $^{25}$Phe-exendin-4(SEQ ID NO:57); $^{14}$Leu-exendin-4 (SEQ ID NO:58); $^{14}$Leu, $^{25}$Phe-exendin-4(1-28)(SEQ ID NO:59); $^{14}$Leu-exendin-4(1-28)(SEQ ID NO:60);
- [N$^\epsilon$-(17-carboxyheptadecanoic acid)Lys$^{20}$]exendin-4(1-39)amide(SEQ ID NO:61);
- [N$^\epsilon$-(17-carboxy-heptadecanoyl)Lys$^{32}$]exendin-4(1-39) amide(SEQ ID NO:62); exendin-4(1-39)-Lys$^{40}$($\epsilon$-(maleimidopropionic acid))-NH$_2$(SEQ ID NO:63); exendin-4(1-39)-Lys$^{40}$($\epsilon$((2-(2-amino)ethoxy acetic acid)-((2-(2-amino)ethoxy acetic acid)-(maleimidopropionic acid))-NH$_2$(SEQ ID NO:64); GLP-1(SEQ ID NO:3); GLP-1(7-37)(SEQ ID NO:65); or Arg$^{34}$Lys$^{26}$(N$^\epsilon$($\gamma$-glutamyl(N$^\alpha$-decanoyl)))GLP-1(7-37)(SEQ ID NO:66).

18. The method of claim 15, wherein the GLP-1 receptor agonist compound is conjugated to at least one macromolecule.

19. A method for decreasing the concentration of fibrinogen in a human in need thereof comprising administering to the human a therapeutically effective amount a pharmaceutical composition comprising exenatide to decrease the concentration of fibrinogen in the human.

* * * * *

SEQUENCE LISTING

```
<160> NUMBER OF SEQ ID NOS: 66

<210> SEQ ID NO 1
<211> LENGTH: 39
<212> TYPE: PRT
<213> ORGANISM: Heloderma horridum

<400> SEQUENCE: 1

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 37
<212> TYPE: PRT
<213> ORGANISM: Homo sapiens
```

<400> SEQUENCE: 3

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 4
<211> LENGTH: 585
<212> TYPE: PRT
<213> ORGANISM: Homo sapiens

<400> SEQUENCE: 4

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

```
Glu Ala Lys Asp Val Phe Leu Gly Met Phe Leu Tyr Glu Tyr Ala Arg
            325                 330                 335

Arg His Pro Asp Tyr Ser Val Val Leu Leu Arg Leu Ala Lys Thr
        340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
        580                 585

<210> SEQ ID NO 5
<211> LENGTH: 616
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Asp
                20                  25                  30

Ala His Lys Ser Glu Val Ala His Arg Phe Lys Asp Leu Gly Glu Glu
        35                  40                  45

Asn Phe Lys Ala Leu Val Leu Ile Ala Phe Ala Gln Tyr Leu Gln Gln
    50                  55                  60

Cys Pro Phe Glu Asp His Val Lys Leu Val Asn Glu Val Thr Glu Phe
65                  70                  75                  80

Ala Lys Thr Cys Val Ala Asp Glu Ser Ala Glu Asn Cys Asp Lys Ser
                85                  90                  95
```

```
Leu His Thr Leu Phe Gly Asp Lys Leu Cys Thr Val Ala Thr Leu Arg
                100                 105                 110

Glu Thr Tyr Gly Glu Met Ala Asp Cys Cys Ala Lys Gln Glu Pro Glu
            115                 120                 125

Arg Asn Glu Cys Phe Leu Gln His Lys Asp Asp Asn Pro Asn Leu Pro
        130                 135                 140

Arg Leu Val Arg Pro Glu Val Asp Val Met Cys Thr Ala Phe His Asp
145                 150                 155                 160

Asn Glu Glu Thr Phe Leu Lys Lys Tyr Leu Tyr Glu Ile Ala Arg Arg
                165                 170                 175

His Pro Tyr Phe Tyr Ala Pro Glu Leu Leu Phe Phe Ala Lys Arg Tyr
            180                 185                 190

Lys Ala Ala Phe Thr Glu Cys Cys Gln Ala Ala Asp Lys Ala Ala Cys
        195                 200                 205

Leu Leu Pro Lys Leu Asp Glu Leu Arg Asp Glu Gly Lys Ala Ser Ser
210                 215                 220

Ala Lys Gln Arg Leu Lys Cys Ala Ser Leu Gln Lys Phe Gly Glu Arg
225                 230                 235                 240

Ala Phe Lys Ala Trp Ala Val Ala Arg Leu Ser Gln Arg Phe Pro Lys
                245                 250                 255

Ala Glu Phe Ala Glu Val Ser Lys Leu Val Thr Asp Leu Thr Lys Val
            260                 265                 270

His Thr Glu Cys Cys His Gly Asp Leu Leu Glu Cys Ala Asp Asp Arg
        275                 280                 285

Ala Asp Leu Ala Lys Tyr Ile Cys Glu Asn Gln Asp Ser Ile Ser Ser
290                 295                 300

Lys Leu Lys Glu Cys Cys Glu Lys Pro Leu Leu Glu Lys Ser His Cys
305                 310                 315                 320

Ile Ala Glu Val Glu Asn Asp Glu Met Pro Ala Asp Leu Pro Ser Leu
                325                 330                 335

Ala Ala Asp Phe Val Glu Ser Lys Asp Val Cys Lys Asn Tyr Ala Glu
            340                 345                 350

Ala Lys Asp Val Phe Leu Gly Met Phe Leu Tyr Glu Tyr Ala Arg Arg
        355                 360                 365

His Pro Asp Tyr Ser Val Val Leu Leu Leu Arg Leu Ala Lys Thr Tyr
370                 375                 380

Glu Thr Thr Leu Glu Lys Cys Cys Ala Ala Ala Asp Pro His Glu Cys
385                 390                 395                 400

Tyr Ala Lys Val Phe Asp Glu Phe Lys Pro Leu Val Glu Glu Pro Gln
                405                 410                 415

Asn Leu Ile Lys Gln Asn Cys Glu Leu Phe Glu Gln Leu Gly Glu Tyr
            420                 425                 430

Lys Phe Gln Asn Ala Leu Leu Val Arg Tyr Thr Lys Lys Val Pro Gln
        435                 440                 445

Val Ser Thr Pro Thr Leu Val Glu Val Ser Arg Asn Leu Gly Lys Val
450                 455                 460

Gly Ser Lys Cys Cys Lys His Pro Glu Ala Lys Arg Met Pro Cys Ala
465                 470                 475                 480

Glu Asp Tyr Leu Ser Val Val Leu Asn Gln Leu Cys Val Leu His Glu
                485                 490                 495

Lys Thr Pro Val Ser Asp Arg Val Thr Lys Cys Cys Thr Glu Ser Leu
            500                 505                 510

Val Asn Arg Arg Pro Cys Phe Ser Ala Leu Glu Val Asp Glu Thr Tyr
        515                 520                 525
```

-continued

```
Val Pro Lys Glu Phe Asn Ala Glu Thr Phe Thr Phe His Ala Asp Ile
        530                 535                 540

Cys Thr Leu Ser Glu Lys Glu Arg Gln Ile Lys Lys Gln Thr Ala Leu
545                 550                 555                 560

Val Glu Leu Val Lys His Lys Pro Lys Ala Thr Lys Glu Gln Leu Lys
                565                 570                 575

Ala Val Met Asp Asp Phe Ala Ala Phe Val Glu Lys Cys Cys Lys Ala
            580                 585                 590

Asp Asp Lys Glu Thr Cys Phe Ala Glu Glu Gly Lys Lys Leu Val Ala
        595                 600                 605

Ala Ser Gln Ala Ala Leu Gly Leu
        610                 615

<210> SEQ ID NO 6
<211> LENGTH: 631
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Gly Ser Gly Gly Gly Gly Ser Gly Gly Gly Gly Ser Asp Ala
        35                  40                  45

His Lys Ser Glu Val Ala His Arg Phe Lys Asp Leu Gly Glu Glu Asn
    50                  55                  60

Phe Lys Ala Leu Val Leu Ile Ala Phe Ala Gln Tyr Leu Gln Gln Cys
65                  70                  75                  80

Pro Phe Glu Asp His Val Lys Leu Val Asn Glu Val Thr Glu Phe Ala
                85                  90                  95

Lys Thr Cys Val Ala Asp Glu Ser Ala Glu Asn Cys Asp Lys Ser Leu
            100                 105                 110

His Thr Leu Phe Gly Asp Lys Leu Cys Thr Val Ala Thr Leu Arg Glu
        115                 120                 125

Thr Tyr Gly Glu Met Ala Asp Cys Cys Ala Lys Gln Glu Pro Glu Arg
130                 135                 140

Asn Glu Cys Phe Leu Gln His Lys Asp Asp Asn Pro Asn Leu Pro Arg
145                 150                 155                 160

Leu Val Arg Pro Glu Val Asp Val Met Cys Thr Ala Phe His Asp Asn
                165                 170                 175

Glu Glu Thr Phe Leu Lys Lys Tyr Leu Tyr Glu Ile Ala Arg Arg His
            180                 185                 190

Pro Tyr Phe Tyr Ala Pro Glu Leu Leu Phe Phe Ala Lys Arg Tyr Lys
        195                 200                 205

Ala Ala Phe Thr Glu Cys Cys Gln Ala Ala Asp Lys Ala Ala Cys Leu
    210                 215                 220

Leu Pro Lys Leu Asp Glu Leu Arg Asp Glu Gly Lys Ala Ser Ser Ala
225                 230                 235                 240

Lys Gln Arg Leu Lys Cys Ala Ser Leu Gln Lys Phe Gly Glu Arg Ala
                245                 250                 255

Phe Lys Ala Trp Ala Val Ala Arg Leu Ser Gln Arg Phe Pro Lys Ala
            260                 265                 270
```

-continued

Glu Phe Ala Glu Val Ser Lys Leu Val Thr Asp Leu Thr Lys Val His
            275                 280                 285

Thr Glu Cys Cys His Gly Asp Leu Leu Glu Cys Ala Asp Asp Arg Ala
        290                 295                 300

Asp Leu Ala Lys Tyr Ile Cys Glu Asn Gln Asp Ser Ile Ser Ser Lys
305                 310                 315                 320

Leu Lys Glu Cys Cys Glu Lys Pro Leu Leu Glu Lys Ser His Cys Ile
                325                 330                 335

Ala Glu Val Glu Asn Asp Glu Met Pro Ala Asp Leu Pro Ser Leu Ala
            340                 345                 350

Ala Asp Phe Val Glu Ser Lys Asp Val Cys Lys Asn Tyr Ala Glu Ala
        355                 360                 365

Lys Asp Val Phe Leu Gly Met Phe Leu Tyr Glu Tyr Ala Arg Arg His
    370                 375                 380

Pro Asp Tyr Ser Val Val Leu Leu Leu Arg Leu Ala Lys Thr Tyr Glu
385                 390                 395                 400

Thr Thr Leu Glu Lys Cys Cys Ala Ala Ala Asp Pro His Glu Cys Tyr
                405                 410                 415

Ala Lys Val Phe Asp Glu Phe Lys Pro Leu Val Glu Glu Pro Gln Asn
            420                 425                 430

Leu Ile Lys Gln Asn Cys Glu Leu Phe Glu Gln Leu Gly Glu Tyr Lys
        435                 440                 445

Phe Gln Asn Ala Leu Leu Val Arg Tyr Thr Lys Lys Val Pro Gln Val
    450                 455                 460

Ser Thr Pro Thr Leu Val Glu Val Ser Arg Asn Leu Gly Lys Val Gly
465                 470                 475                 480

Ser Lys Cys Cys Lys His Pro Glu Ala Lys Arg Met Pro Cys Ala Glu
                485                 490                 495

Asp Tyr Leu Ser Val Val Leu Asn Gln Leu Cys Val Leu His Glu Lys
            500                 505                 510

Thr Pro Val Ser Asp Arg Val Thr Lys Cys Cys Thr Glu Ser Leu Val
        515                 520                 525

Asn Arg Arg Pro Cys Phe Ser Ala Leu Glu Val Asp Glu Thr Tyr Val
    530                 535                 540

Pro Lys Glu Phe Asn Ala Glu Thr Phe Thr Phe His Ala Asp Ile Cys
545                 550                 555                 560

Thr Leu Ser Glu Lys Glu Arg Gln Ile Lys Lys Gln Thr Ala Leu Val
                565                 570                 575

Glu Leu Val Lys His Lys Pro Lys Ala Thr Lys Glu Gln Leu Lys Ala
            580                 585                 590

Val Met Asp Asp Phe Ala Ala Phe Val Glu Lys Cys Cys Lys Ala Asp
        595                 600                 605

Asp Lys Glu Thr Cys Phe Ala Glu Glu Gly Lys Lys Leu Val Ala Ala
    610                 615                 620

Ser Gln Ala Ala Leu Gly Leu
625                 630

<210> SEQ ID NO 7
<211> LENGTH: 640
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

-continued

```
His Gly Glu Gly Thr Phe Thr Ser Asp Val Ser Ser Tyr Leu Glu
 1               5                  10                  15

Gln Ala Ala Lys Glu Phe Ile Ala Trp Leu Val Lys Gly Arg Gly Ser
             20                  25                  30

Ser Gly Ala Pro Pro Ser Gly Gly Gly Gly Ser Gly Gly Gly
             35                  40                  45

Gly Ser Gly Gly Gly Gly Ser Asp Ala His Lys Ser Glu Val Ala His
     50                  55                  60

Arg Phe Lys Asp Leu Gly Glu Glu Asn Phe Lys Ala Leu Val Leu Ile
 65              70                  75                  80

Ala Phe Ala Gln Tyr Leu Gln Gln Cys Pro Phe Glu Asp His Val Lys
                 85                  90                  95

Leu Val Asn Glu Val Thr Glu Phe Ala Lys Thr Cys Val Ala Asp Glu
                100                 105                 110

Ser Ala Glu Asn Cys Asp Lys Ser Leu His Thr Leu Phe Gly Asp Lys
            115                 120                 125

Leu Cys Thr Val Ala Thr Leu Arg Glu Thr Tyr Gly Glu Met Ala Asp
130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
                180                 185                 190

Tyr Leu Tyr Glu Ile Ala Arg Arg His Pro Tyr Phe Tyr Ala Pro Glu
            195                 200                 205

Leu Leu Phe Phe Ala Lys Arg Tyr Lys Ala Ala Phe Thr Glu Cys Cys
210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
        370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
            405                 410                 415

Ala Ala Ala Asp Pro His Glu Cys Tyr Ala Lys Val Phe Asp Glu Phe
```

```
                420              425              430
Lys Pro Leu Val Glu Pro Gln Asn Leu Ile Lys Gln Asn Cys Glu
            435              440              445
Leu Phe Glu Gln Leu Gly Glu Tyr Lys Phe Gln Asn Ala Leu Leu Val
        450              455              460
Arg Tyr Thr Lys Lys Val Pro Gln Val Ser Thr Pro Thr Leu Val Glu
465              470              475              480
Val Ser Arg Asn Leu Gly Lys Val Gly Ser Lys Cys Cys Lys His Pro
                485              490              495
Glu Ala Lys Arg Met Pro Cys Ala Glu Asp Tyr Leu Ser Val Val Leu
            500              505              510
Asn Gln Leu Cys Val Leu His Glu Lys Thr Pro Val Ser Asp Arg Val
        515              520              525
Thr Lys Cys Cys Thr Glu Ser Leu Val Asn Arg Arg Pro Cys Phe Ser
530              535              540
Ala Leu Glu Val Asp Glu Thr Tyr Val Pro Lys Glu Phe Asn Ala Glu
545              550              555              560
Thr Phe Thr Phe His Ala Asp Ile Cys Thr Leu Ser Glu Lys Glu Arg
                565              570              575
Gln Ile Lys Lys Gln Thr Ala Leu Val Glu Leu Val Lys His Lys Pro
            580              585              590
Lys Ala Thr Lys Glu Gln Leu Lys Ala Val Met Asp Asp Phe Ala Ala
        595              600              605
Phe Val Glu Lys Cys Cys Lys Ala Asp Asp Lys Glu Thr Cys Phe Ala
    610              615              620
Glu Glu Gly Lys Lys Leu Val Ala Ala Ser Gln Ala Ala Leu Gly Leu
625              630              635              640

<210> SEQ ID NO 8
<211> LENGTH: 624
<212> TYPE: PRT
<213> ORGANISM: Homo sapiens

<400> SEQUENCE: 8

His Gly Glu Gly Thr Phe Thr Ser Asp Leu Ser Lys Gln Met Glu Glu
1               5                  10                  15
Glu Ala Val Arg Leu Phe Ile Glu Trp Leu Lys Asn Gly Gly Pro Ser
            20                  25                  30
Ser Gly Ala Pro Pro Pro Ser Asp Ala His Lys Ser Glu Val Ala His
        35                  40                  45
Arg Phe Lys Asp Leu Gly Glu Glu Asn Phe Lys Ala Leu Val Leu Ile
    50                  55                  60
Ala Phe Ala Gln Tyr Leu Gln Gln Cys Pro Phe Glu Asp His Val Lys
65                  70                  75                  80
Leu Val Asn Glu Val Thr Glu Phe Ala Lys Thr Cys Val Ala Asp Glu
                85                  90                  95
Ser Ala Glu Asn Cys Asp Lys Ser Leu His Thr Leu Phe Gly Asp Lys
            100                 105                 110
Leu Cys Thr Val Ala Thr Leu Arg Glu Thr Tyr Gly Glu Met Ala Asp
        115                 120                 125
Cys Cys Ala Lys Gln Glu Pro Glu Arg Asn Glu Cys Phe Leu Gln His
    130                 135                 140
Lys Asp Asp Asn Pro Asn Leu Pro Arg Leu Val Arg Pro Glu Val Asp
145                 150                 155                 160
Val Met Cys Thr Ala Phe His Asp Asn Glu Glu Thr Phe Leu Lys Lys
```

```
                          165                 170                 175
Tyr Leu Tyr Glu Ile Ala Arg Arg His Pro Tyr Phe Tyr Ala Pro Glu
                180                 185                 190
Leu Leu Phe Phe Ala Lys Arg Tyr Lys Ala Ala Phe Thr Glu Cys Cys
            195                 200                 205
Gln Ala Ala Asp Lys Ala Ala Cys Leu Leu Pro Lys Leu Asp Glu Leu
        210                 215                 220
Arg Asp Glu Gly Lys Ala Ser Ser Ala Lys Gln Arg Leu Lys Cys Ala
225                 230                 235                 240
Ser Leu Gln Lys Phe Gly Glu Arg Ala Phe Lys Ala Trp Ala Val Ala
                245                 250                 255
Arg Leu Ser Gln Arg Phe Pro Lys Ala Glu Phe Ala Glu Val Ser Lys
            260                 265                 270
Leu Val Thr Asp Leu Thr Lys Val His Thr Glu Cys Cys His Gly Asp
        275                 280                 285
Leu Leu Glu Cys Ala Asp Asp Arg Ala Asp Leu Ala Lys Tyr Ile Cys
        290                 295                 300
Glu Asn Gln Asp Ser Ile Ser Ser Lys Leu Lys Glu Cys Cys Glu Lys
305                 310                 315                 320
Pro Leu Leu Glu Lys Ser His Cys Ile Ala Glu Val Glu Asn Asp Glu
                325                 330                 335
Met Pro Ala Asp Leu Pro Ser Leu Ala Ala Asp Phe Val Glu Ser Lys
            340                 345                 350
Asp Val Cys Lys Asn Tyr Ala Glu Ala Lys Asp Val Phe Leu Gly Met
            355                 360                 365
Phe Leu Tyr Glu Tyr Ala Arg Arg His Pro Asp Tyr Ser Val Val Leu
        370                 375                 380
Leu Leu Arg Leu Ala Lys Thr Tyr Glu Thr Thr Leu Glu Lys Cys Cys
385                 390                 395                 400
Ala Ala Ala Asp Pro His Glu Cys Tyr Ala Lys Val Phe Asp Glu Phe
                405                 410                 415
Lys Pro Leu Val Glu Glu Pro Gln Asn Leu Ile Lys Gln Asn Cys Glu
            420                 425                 430
Leu Phe Glu Gln Leu Gly Glu Tyr Lys Phe Gln Asn Ala Leu Leu Val
        435                 440                 445
Arg Tyr Thr Lys Lys Val Pro Gln Val Ser Thr Pro Thr Leu Val Glu
        450                 455                 460
Val Ser Arg Asn Leu Gly Lys Val Gly Ser Lys Cys Cys Lys His Pro
465                 470                 475                 480
Glu Ala Lys Arg Met Pro Cys Ala Glu Asp Tyr Leu Ser Val Val Leu
                485                 490                 495
Asn Gln Leu Cys Val Leu His Glu Lys Thr Pro Val Ser Asp Arg Val
            500                 505                 510
Thr Lys Cys Cys Thr Glu Ser Leu Val Asn Arg Arg Pro Cys Phe Ser
        515                 520                 525
Ala Leu Glu Val Asp Glu Thr Tyr Val Pro Lys Glu Phe Asn Ala Glu
        530                 535                 540
Thr Phe Thr Phe His Ala Asp Ile Cys Thr Leu Ser Glu Lys Glu Arg
545                 550                 555                 560
Gln Ile Lys Lys Gln Thr Ala Leu Val Glu Leu Val Lys His Lys Pro
                565                 570                 575
Lys Ala Thr Lys Glu Gln Leu Lys Ala Val Met Asp Asp Phe Ala Ala
            580                 585                 590
```

```
Phe Val Glu Lys Cys Cys Lys Ala Asp Asp Lys Glu Thr Cys Phe Ala
        595                 600                 605

Glu Glu Gly Lys Lys Leu Val Ala Ala Ser Gln Ala Ala Leu Gly Leu
    610                 615                 620

<210> SEQ ID NO 9
<211> LENGTH: 264
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260

<210> SEQ ID NO 10
<211> LENGTH: 272
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

His Val Glu Gly Thr Phe Thr Ser Asp Val Ser Ser Tyr Leu Glu Gly
```

```
  1               5                  10                 15
Gln Ala Ala Lys Glu Phe Ile Ala Trp Leu Val Lys Gly Arg Gly Ser
                20                  25                 30

Ser Gly Ala Pro Pro Ser Ala Glu Pro Lys Ser Cys Asp Lys Thr
            35                  40                  45

His Thr Cys Pro Pro Cys Pro Ala Pro Glu Leu Leu Gly Gly Pro Ser
 50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
                100                 105                110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
            130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
            195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Glu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
                260                 265                 270

<210> SEQ ID NO 11
<211> LENGTH: 272
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

His Gly Glu Gly Thr Phe Thr Ser Asp Leu Ser Lys Gln Met Glu Glu
 1               5                  10                 15

Glu Ala Val Arg Leu Phe Ile Glu Trp Leu Lys Asn Gly Gly Pro Ser
                20                  25                 30

Ser Gly Ala Ser Ser Gly Ala Ala Glu Pro Lys Ser Cys Asp Lys Thr
            35                  40                  45

His Thr Cys Pro Pro Cys Pro Ala Pro Glu Leu Leu Gly Gly Pro Ser
 50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
```

```
                    100                 105                 110
Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
        130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: His, Arg or Tyr
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Ala, Asp or Glu
<220> FEATURE:
<221> NAME/KEY: MOD_RES
<222> LOCATION: (6)..(6)
<223> OTHER INFORMATION: Phe, Tyr or naphthylalanine
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (9)..(9)
<223> OTHER INFORMATION: Asp or Glu
<220> FEATURE:
<221> NAME/KEY: MOD_RES
<222> LOCATION: (10)..(10)
<223> OTHER INFORMATION: Leu, Ile, Val, pentylglycine or Met
<220> FEATURE:
<221> NAME/KEY: MOD_RES
<222> LOCATION: (14)..(14)
<223> OTHER INFORMATION: Leu, Ile, pentylglycine, Val or Met
<220> FEATURE:
<221> NAME/KEY: MOD_RES
<222> LOCATION: (22)..(22)
<223> OTHER INFORMATION: Phe, Tyr or naphthylalanine
```

```
<220> FEATURE:
<221> NAME/KEY: MOD_RES
<222> LOCATION: (23)..(23)
<223> OTHER INFORMATION: Ile, Val, Leu, pentylglycine, tert-butylglycine
      or Met
<220> FEATURE:
<221> NAME/KEY: MOD_RES
<222> LOCATION: (24)..(24)
<223> OTHER INFORMATION: Glu or Asp
<220> FEATURE:
<221> NAME/KEY: MOD_RES
<222> LOCATION: (25)..(25)
<223> OTHER INFORMATION: Trp, Phe, Tyr or naphthylalanine
<220> FEATURE:
<221> NAME/KEY: MOD_RES
<222> LOCATION: (31)..(31)
<223> OTHER INFORMATION: Pro, hPro, 3Hyp, 4Hyp, thioproline,
      n-alkylglycine, n-alkylpentylglycine or n-alkylalanine
<220> FEATURE:
<221> NAME/KEY: MOD_RES
<222> LOCATION: (36)..(38)
<223> OTHER INFORMATION: Pro, hPro, 3Hyp, 4Hyp, thioproline,
      n-alkylglycine, n-alkylpentylglycine or n-alkylalanine
<220> FEATURE:
<221> NAME/KEY: MOD_RES
<222> LOCATION: (39)..(39)
<223> OTHER INFORMATION: Ser, Thr or Tyr

<400> SEQUENCE: 12

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
            35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: His, Arg or Tyr
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Ala, Asp or Glu
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (6)..(6)
<223> OTHER INFORMATION: Ala, Phe, Tyr or naphthylalanine
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ala, Ser or Thr
<220> FEATURE:
<221> NAME/KEY: MOD_RES
<222> LOCATION: (9)..(9)
<223> OTHER INFORMATION: Asp or Glu
<220> FEATURE:
```

-continued

```
<221> NAME/KEY: MOD_RES
<222> LOCATION: (10)..(10)
<223> OTHER INFORMATION: Ala, Leu, Ile, Val, pentylglycine or Met
<220> FEATURE:
<221> NAME/KEY: MOD_RES
<222> LOCATION: (11)..(11)
<223> OTHER INFORMATION: Ala or Ser
<220> FEATURE:
<221> NAME/KEY: MOD_RES
<222> LOCATION: (12)..(12)
<223> OTHER INFORMATION: Ala or Lys
<220> FEATURE:
<221> NAME/KEY: MOD_RES
<222> LOCATION: (13)..(13)
<223> OTHER INFORMATION: Ala or Gln
<220> FEATURE:
<221> NAME/KEY: MOD_RES
<222> LOCATION: (14)..(14)
<223> OTHER INFORMATION: Ala, Leu, Ile, pentylglycine, Val or Met
<220> FEATURE:
<221> NAME/KEY: MOD_RES
<222> LOCATION: (15)..(15)
<223> OTHER INFORMATION: Ala or Glu
<220> FEATURE:
<221> NAME/KEY: MOD_RES
<222> LOCATION: (16)..(16)
<223> OTHER INFORMATION: Ala or Glu
<220> FEATURE:
<221> NAME/KEY: MOD_RES
<222> LOCATION: (17)..(17)
<223> OTHER INFORMATION: Ala or Glu
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Ala or Arg
<220> FEATURE:
<221> NAME/KEY: MOD_RES
<222> LOCATION: (21)..(21)
<223> OTHER INFORMATION: Ala or Leu
<220> FEATURE:
<221> NAME/KEY: MOD_RES
<222> LOCATION: (22)..(22)
<223> OTHER INFORMATION: Ala, Phe, Tyr or naphthylalanine
<220> FEATURE:
<221> NAME/KEY: MOD_RES
<222> LOCATION: (23)..(23)
<223> OTHER INFORMATION: Ile, Val, Leu, pentylglycine, tert-butylglycine
      or Met
<220> FEATURE:
<221> NAME/KEY: MOD_RES
<222> LOCATION: (24)..(24)
<223> OTHER INFORMATION: Ala, Glu or Asp
<220> FEATURE:
<221> NAME/KEY: MOD_RES
<222> LOCATION: (25)..(25)
<223> OTHER INFORMATION: Ala, Trp, Phe, Tyr or naphthylalanine
<220> FEATURE:
<221> NAME/KEY: MOD_RES
<222> LOCATION: (26)..(26)
<223> OTHER INFORMATION: Ala or Leu
<220> FEATURE:
<221> NAME/KEY: MOD_RES
<222> LOCATION: (27)..(27)
<223> OTHER INFORMATION: Ala or Lys
<220> FEATURE:
<221> NAME/KEY: MOD_RES
<222> LOCATION: (28)..(28)
<223> OTHER INFORMATION: Ala or Asn
<220> FEATURE:
<221> NAME/KEY: MOD_RES
<222> LOCATION: (29)..(29)
<223> OTHER INFORMATION: Gly or not present
<220> FEATURE:
<221> NAME/KEY: MOD_RES
<222> LOCATION: (30)..(30)
<223> OTHER INFORMATION: Gly or not present
```

```
<220> FEATURE:
<221> NAME/KEY: MOD_RES
<222> LOCATION: (31)..(31)
<223> OTHER INFORMATION: Pro, hPro, 3Hyp, 4Hyp, thioproline,
      n-alkylglycine, n-alkylpentylglycine or n-alkylalanine or
      not present
<220> FEATURE:
<221> NAME/KEY: MOD_RES
<222> LOCATION: (32)..(32)
<223> OTHER INFORMATION: Ser or not present
<220> FEATURE:
<221> NAME/KEY: MOD_RES
<222> LOCATION: (33)..(33)
<223> OTHER INFORMATION: Ser or not present
<220> FEATURE:
<221> NAME/KEY: MOD_RES
<222> LOCATION: (34)..(34)
<223> OTHER INFORMATION: Gly or not present
<220> FEATURE:
<221> NAME/KEY: MOD_RES
<222> LOCATION: (35)..(35)
<223> OTHER INFORMATION: Ala or not present
<220> FEATURE:
<221> NAME/KEY: MOD_RES
<222> LOCATION: (36)..(38)
<223> OTHER INFORMATION: Pro, hPro, 3Hyp, 4Hyp, thioproline,
      n-alkylglycine, n-alkylpentylglycine or n-alkylalanine or
      not present

<400> SEQUENCE: 13

Xaa Xaa Xaa Gly Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
            35

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine

<400> SEQUENCE: 14

Gly Gly Xaa Ser Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine

<400> SEQUENCE: 15

Gly Gly Xaa Ser Ser Gly
1               5

<210> SEQ ID NO 16
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine

<400> SEQUENCE: 16

Gly Gly Xaa Ser Ser Gly Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine
<220> FEATURE:
<221> NAME/KEY: MOD_RES
<222> LOCATION: (8)..(8)
<223> OTHER INFORMATION: Pro, hPro, 3Hyp, 4Hyp, thioproline,
      n-alkylglycine, n-alkylpentylglycine or n-alkylalanine

<400> SEQUENCE: 17

Gly Gly Xaa Ser Ser Gly Ala Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine
<220> FEATURE:
<221> NAME/KEY: MOD_RES
<222> LOCATION: (8)..(9)
<223> OTHER INFORMATION: Pro, hPro, 3Hyp, 4Hyp, thioproline,
      n-alkylglycine, n-alkylpentylglycine or n-alkylalanine

<400> SEQUENCE: 18

Gly Gly Xaa Ser Ser Gly Ala Xaa Xaa
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine
<220> FEATURE:
<221> NAME/KEY: MOD_RES
```

```
<222> LOCATION: (8)..(10)
<223> OTHER INFORMATION: Pro, hPro, 3Hyp, 4Hyp, thioproline,
      n-alkylglycine, n-alkylpentylglycine or n-alkylalanine

<400> SEQUENCE: 19

Gly Gly Xaa Ser Ser Gly Ala Xaa Xaa Xaa
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, thioproline or n-methylalanine

<400> SEQUENCE: 20

Gly Gly Xaa Ser Ser
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, thioproline or n-methylalanine

<400> SEQUENCE: 21

Gly Gly Xaa Ser Ser Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, thioproline or n-methylalanine

<400> SEQUENCE: 22

Gly Gly Xaa Ser Ser Gly Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, thioproline or n-methylalanine
<220> FEATURE:
<221> NAME/KEY: MOD_RES
<222> LOCATION: (8)..(8)
<223> OTHER INFORMATION: Pro, hPro, thioproline or n-methylalanine
```

```
<400> SEQUENCE: 23

Gly Gly Xaa Ser Ser Gly Ala Xaa
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, thioproline or n-methylalanine
<220> FEATURE:
<221> NAME/KEY: MOD_RES
<222> LOCATION: (8)..(9)
<223> OTHER INFORMATION: Pro, hPro, thioproline or n-methylalanine

<400> SEQUENCE: 24

Gly Gly Xaa Ser Ser Gly Ala Xaa Xaa
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, thioproline or n-methylalanine
<220> FEATURE:
<221> NAME/KEY: MOD_RES
<222> LOCATION: (8)..(10)
<223> OTHER INFORMATION: Pro, hPro, thioproline or n-methylalanine

<400> SEQUENCE: 25

Gly Gly Xaa Ser Ser Gly Ala Xaa Xaa Xaa
1               5                   10

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: His, Arg, Tyr, Ala, Norval, Val or Norleu
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Ala, Asp or Glu
<220> FEATURE:
<221> NAME/KEY: MOD_RES
<222> LOCATION: (4)..(4)
<223> OTHER INFORMATION: Ala, Norval, Val, Norleu or Gly
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (6)..(6)
```

-continued

```
<223> OTHER INFORMATION: Phe, Tyr or naphthylalanine
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ala, Ser or Thr
<220> FEATURE:
<221> NAME/KEY: MOD_RES
<222> LOCATION: (9)..(9)
<223> OTHER INFORMATION: Ala, Norval, Val, Norleu, Asp or Glu
<220> FEATURE:
<221> NAME/KEY: MOD_RES
<222> LOCATION: (10)..(10)
<223> OTHER INFORMATION: Ala, Leu, Ile, Val, pentylglycine or Met
<220> FEATURE:
<221> NAME/KEY: MOD_RES
<222> LOCATION: (11)..(11)
<223> OTHER INFORMATION: Ala or Ser
<220> FEATURE:
<221> NAME/KEY: MOD_RES
<222> LOCATION: (12)..(12)
<223> OTHER INFORMATION: Ala or Lys
<220> FEATURE:
<221> NAME/KEY: MOD_RES
<222> LOCATION: (13)..(13)
<223> OTHER INFORMATION: Ala or Gln
<220> FEATURE:
<221> NAME/KEY: MOD_RES
<222> LOCATION: (14)..(14)
<223> OTHER INFORMATION: Ala, Leu, Ile, pentylglycine or Met
<220> FEATURE:
<221> NAME/KEY: MOD_RES
<222> LOCATION: (15)..(15)
<223> OTHER INFORMATION: Ala or Glu
<220> FEATURE:
<221> NAME/KEY: MOD_RES
<222> LOCATION: (16)..(16)
<223> OTHER INFORMATION: Ala or Glu
<220> FEATURE:
<221> NAME/KEY: MOD_RES
<222> LOCATION: (17)..(17)
<223> OTHER INFORMATION: Ala or Glu
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Ala or Arg
<220> FEATURE:
<221> NAME/KEY: MOD_RES
<222> LOCATION: (21)..(21)
<223> OTHER INFORMATION: Ala or Leu
<220> FEATURE:
<221> NAME/KEY: MOD_RES
<222> LOCATION: (22)..(22)
<223> OTHER INFORMATION: Phe, Tyr or naphthylalanine
<220> FEATURE:
<221> NAME/KEY: MOD_RES
<222> LOCATION: (23)..(23)
<223> OTHER INFORMATION: Ile, Val, Leu, pentylglycine,
      tert-butylglycine or Met
<220> FEATURE:
<221> NAME/KEY: MOD_RES
<222> LOCATION: (24)..(24)
<223> OTHER INFORMATION: Ala, Glu or Asp
<220> FEATURE:
<221> NAME/KEY: MOD_RES
<222> LOCATION: (25)..(25)
<223> OTHER INFORMATION: Ala, Trp, Phe, Tyr or naphthylalanine
<220> FEATURE:
<221> NAME/KEY: MOD_RES
<222> LOCATION: (26)..(26)
<223> OTHER INFORMATION: Ala or Leu
<220> FEATURE:
<221> NAME/KEY: MOD_RES
```

```
<222> LOCATION: (27)..(27)
<223> OTHER INFORMATION: Ala or Lys
<220> FEATURE:
<221> NAME/KEY: MOD_RES
<222> LOCATION: (28)..(28)
<223> OTHER INFORMATION: Ala or Asn
<220> FEATURE:
<221> NAME/KEY: MOD_RES
<222> LOCATION: (29)..(29)
<223> OTHER INFORMATION: Gly or not present
<220> FEATURE:
<221> NAME/KEY: MOD_RES
<222> LOCATION: (30)..(30)
<223> OTHER INFORMATION: Gly or not present
<220> FEATURE:
<221> NAME/KEY: MOD_RES
<222> LOCATION: (31)..(31)
<223> OTHER INFORMATION: Pro, hPro, 3Hyp, 4Hyp, thioproline,
      n-alkylglycine, n-alkylpentylglycine or n-alkylalanine or
      not present
<220> FEATURE:
<221> NAME/KEY: MOD_RES
<222> LOCATION: (32)..(32)
<223> OTHER INFORMATION: Ser or not present
<220> FEATURE:
<221> NAME/KEY: MOD_RES
<222> LOCATION: (33)..(33)
<223> OTHER INFORMATION: Ser or not present
<220> FEATURE:
<221> NAME/KEY: MOD_RES
<222> LOCATION: (34)..(34)
<223> OTHER INFORMATION: Gly or not present
<220> FEATURE:
<221> NAME/KEY: MOD_RES
<222> LOCATION: (35)..(35)
<223> OTHER INFORMATION: Ala or not present
<220> FEATURE:
<221> NAME/KEY: MOD_RES
<222> LOCATION: (36)..(39)
<223> OTHER INFORMATION: Pro, hPro, 3Hyp, 4Hyp, thioproline,
      n-alkylglycine, n-alkylpentylglycine or n-alkylalanine or
      not present

<400> SEQUENCE: 26

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa Xaa
        35

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, hPro, 3Hyp, 4Hyp, thioproline,
      n-alkylglycine, n-alkylpentylglycine or n-alkylalanine or
      not present
<220> FEATURE:
<221> NAME/KEY: MOD_RES
<222> LOCATION: (8)..(11)
<223> OTHER INFORMATION: Pro, hPro, 3Hyp, 4Hyp, thioproline,
      n-alkylglycine, n-alkylpentylglycine or n-alkylalanine or
      not present

<400> SEQUENCE: 27

Gly Gly Xaa Ser Ser Gly Ala Xaa Xaa Xaa Xaa
1               5                   10
```

```
<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Ala His Lys
1

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: His, D-His, desamino-histidine,
      2-amino-histidine, beta-hydroxy-histidine, hHis,
      N-alpha-acetyl-histidine, alpha-fluoromethyl-histidine,
      alpha-methyl-histidine, 3-pyridylalanine, 2-pyridylalanine or
      4-pyridylalanine
<220> FEATURE:
<221> NAME/KEY: MOD_RES
<222> LOCATION: (2)..(2)
<223> OTHER INFORMATION: Ala, D-Ala, Gly, Val, Leu, Ile, Lys, Aib, or
      not present
<220> FEATURE:
<221> NAME/KEY: MOD_RES
<222> LOCATION: (10)..(10)
<223> OTHER INFORMATION: Val or Leu
<220> FEATURE:
<221> NAME/KEY: MOD_RES
<222> LOCATION: (12)..(12)
<223> OTHER INFORMATION: Ser, Lys or Arg
<220> FEATURE:
<221> NAME/KEY: MOD_RES
<222> LOCATION: (13)..(13)
<223> OTHER INFORMATION: Tyr or Gln
<220> FEATURE:
<221> NAME/KEY: MOD_RES
<222> LOCATION: (14)..(14)
<223> OTHER INFORMATION: Leu or Met
<220> FEATURE:
<221> NAME/KEY: MOD_RES
<222> LOCATION: (16)..(16)
<223> OTHER INFORMATION: Gly, Glu or Aib
<220> FEATURE:
<221> NAME/KEY: MOD_RES
<222> LOCATION: (17)..(17)
<223> OTHER INFORMATION: Gln, Glu, Lys or Arg
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Lys, Glu or Arg
<220> FEATURE:
<221> NAME/KEY: MOD_RES
<222> LOCATION: (21)..(21)
<223> OTHER INFORMATION: Glu or Leu
<220> FEATURE:
<221> NAME/KEY: MOD_RES
<222> LOCATION: (24)..(24)
<223> OTHER INFORMATION: Ala, Glu or Arg
<220> FEATURE:
<221> NAME/KEY: MOD_RES
<222> LOCATION: (27)..(27)
<223> OTHER INFORMATION: Val or Lys
<220> FEATURE:
```

```
<221> NAME/KEY: MOD_RES
<222> LOCATION: (28)..(28)
<223> OTHER INFORMATION: Lys, Glu, Asn or Arg
<220> FEATURE:
<221> NAME/KEY: MOD_RES
<222> LOCATION: (29)..(29)
<223> OTHER INFORMATION: Gly or Aib
<220> FEATURE:
<221> NAME/KEY: MOD_RES
<222> LOCATION: (30)..(30)
<223> OTHER INFORMATION: Arg, Gly or Lys
<220> FEATURE:
<221> NAME/KEY: MOD_RES
<222> LOCATION: (31)..(31)
<223> OTHER INFORMATION: Gly, Ala, Glu, Pro, Lys or absent
<220> FEATURE:
<221> NAME/KEY: MOD_RES
<222> LOCATION: (32)..(32)
<223> OTHER INFORMATION: Lys, Ser or absent
<220> FEATURE:
<221> NAME/KEY: MOD_RES
<222> LOCATION: (33)..(33)
<223> OTHER INFORMATION: Ser, Lys or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ala or absent
<220> FEATURE:
<221> NAME/KEY: MOD_RES
<222> LOCATION: (36)..(36)
<223> OTHER INFORMATION: Pro or absent
<220> FEATURE:
<221> NAME/KEY: MOD_RES
<222> LOCATION: (37)..(37)
<223> OTHER INFORMATION: Pro or absent
<220> FEATURE:
<221> NAME/KEY: MOD_RES
<222> LOCATION: (38)..(38)
<223> OTHER INFORMATION: Pro or absent
<220> FEATURE:
<221> NAME/KEY: MOD_RES
<222> LOCATION: (39)..(39)
<223> OTHER INFORMATION: Ser or absent
<220> FEATURE:
<223> OTHER INFORMATION: provided that if Xaa32, Xaa33, Xaa34, Xaa35,
      Xaa36, Xaa37, Xaa38 or Xaa39 is absent then each amino acid
      residue downstream is also absent

<400> SEQUENCE: 29

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa
        35

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Lys Lys Lys Lys
1               5

<210> SEQ ID NO 31
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: His, D-His, desamino-histidine, 2-amino-3-(2-
      aminoimidazol-4-yl)propionic acid, beta-hydroxy-His, hHis,
      N-alpha-acetyl-His, alpha-fluoromethyl-His, alpha-methyl-His, 3-
      pyridylalanine, 2-pyridylalanine or 4-pyridylalanine
<220> FEATURE:
<221> NAME/KEY: MOD_RES
<222> LOCATION: (2)..(2)
<223> OTHER INFORMATION: Ala, Gly, Val, Leu, Ile, Lys, Aib, or
      not present
<220> FEATURE:
<221> NAME/KEY: MOD_RES
<222> LOCATION: (10)..(10)
<223> OTHER INFORMATION: Val or Leu
<220> FEATURE:
<221> NAME/KEY: MOD_RES
<222> LOCATION: (12)..(12)
<223> OTHER INFORMATION: Ser, Lys or Arg
<220> FEATURE:
<221> NAME/KEY: MOD_RES
<222> LOCATION: (13)..(13)
<223> OTHER INFORMATION: Tyr or Gln
<220> FEATURE:
<221> NAME/KEY: MOD_RES
<222> LOCATION: (14)..(14)
<223> OTHER INFORMATION: Leu or Met
<220> FEATURE:
<221> NAME/KEY: MOD_RES
<222> LOCATION: (16)..(16)
<223> OTHER INFORMATION: Gly, Glu or Aib
<220> FEATURE:
<221> NAME/KEY: MOD_RES
<222> LOCATION: (17)..(17)
<223> OTHER INFORMATION: Gln, Glu, Lys or Arg
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Lys, Glu or Arg
<220> FEATURE:
<221> NAME/KEY: MOD_RES
<222> LOCATION: (21)..(21)
<223> OTHER INFORMATION: Glu or Leu
<220> FEATURE:
<221> NAME/KEY: MOD_RES
<222> LOCATION: (24)..(24)
<223> OTHER INFORMATION: Ala, Glu or Arg
<220> FEATURE:
<221> NAME/KEY: MOD_RES
<222> LOCATION: (27)..(27)
<223> OTHER INFORMATION: Val or Lys
<220> FEATURE:
<221> NAME/KEY: MOD_RES
<222> LOCATION: (28)..(28)
<223> OTHER INFORMATION: Lys, Glu, Asn or Arg
<220> FEATURE:
<221> NAME/KEY: MOD_RES
<222> LOCATION: (29)..(29)
<223> OTHER INFORMATION: Gly or Aib
<220> FEATURE:
<221> NAME/KEY: MOD_RES
<222> LOCATION: (30)..(30)
<223> OTHER INFORMATION: Arg, Gly or Lys
<220> FEATURE:
<221> NAME/KEY: MOD_RES
<222> LOCATION: (31)..(31)
<223> OTHER INFORMATION: Gly, Ala, Glu, Pro, Lys or absent
<220> FEATURE:
<221> NAME/KEY: MOD_RES
<222> LOCATION: (32)..(32)
```

```
<223> OTHER INFORMATION: Lys, Ser or absent
<220> FEATURE:
<221> NAME/KEY: MOD_RES
<222> LOCATION: (33)..(33)
<223> OTHER INFORMATION: Ser, Lys or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ala or absent
<220> FEATURE:
<221> NAME/KEY: MOD_RES
<222> LOCATION: (36)..(36)
<223> OTHER INFORMATION: Pro or absent
<220> FEATURE:
<221> NAME/KEY: MOD_RES
<222> LOCATION: (37)..(37)
<223> OTHER INFORMATION: Pro or absent
<220> FEATURE:
<221> NAME/KEY: MOD_RES
<222> LOCATION: (38)..(38)
<223> OTHER INFORMATION: Pro or absent
<220> FEATURE:
<221> NAME/KEY: MOD_RES
<222> LOCATION: (39)..(39)
<223> OTHER INFORMATION: Ser or absent
<220> FEATURE:
<223> OTHER INFORMATION: provided that if Xaa32, Xaa33, Xaa34, Xaa35,
      Xaa36, Xaa37, Xaa38 or Xaa39 is absent then each amino acid
      residue downstream is also absent

<400> SEQUENCE: 31

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa
        35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (2)..(2)
<223> OTHER INFORMATION: Ala, Gly, Ser, Thr, Leu, Ile, Val, Glu, Asp,
      Met or Lys
<220> FEATURE:
<221> NAME/KEY: MOD_RES
<222> LOCATION: (3)..(3)
<223> OTHER INFORMATION: Glu, Asp or Lys
<220> FEATURE:
<221> NAME/KEY: MOD_RES
<222> LOCATION: (5)..(5)
<223> OTHER INFORMATION: Thr, Ala, Gly, Ser, Leu, Ile, Val, Glu, Asp or
      Lys
<220> FEATURE:
<221> NAME/KEY: MOD_RES
<222> LOCATION: (8)..(8)
<223> OTHER INFORMATION: Ser, Ala, Gly, Thr, Leu, Ile, Val, Glu, Asp or
      Lys
<220> FEATURE:
<221> NAME/KEY: MOD_RES
<222> LOCATION: (10)..(10)
<223> OTHER INFORMATION: Val, Ala, Gly, Ser, Thr, Leu, Ile, Tyr, Glu,
      Asp or Lys
<220> FEATURE:
<221> NAME/KEY: MOD_RES
<222> LOCATION: (11)..(11)
```

-continued

```
<223> OTHER INFORMATION: Ser, Ala, Gly, Thr, Leu, Ile, Val, Glu, Asp or
      Lys
<220> FEATURE:
<221> NAME/KEY: MOD_RES
<222> LOCATION: (12)..(12)
<223> OTHER INFORMATION: Ser, Ala, Gly, Thr, Leu, Ile, Val, Glu, Asp or
      Lys
<220> FEATURE:
<221> NAME/KEY: MOD_RES
<222> LOCATION: (13)..(13)
<223> OTHER INFORMATION: Tyr, Phe, Trp, Glu, Asp or Lys
<220> FEATURE:
<221> NAME/KEY: MOD_RES
<222> LOCATION: (14)..(14)
<223> OTHER INFORMATION: Leu, Ala, Gly, Ser, Thr, Leu, Ile, Val, Glu,
      Asp or Lys
<220> FEATURE:
<221> NAME/KEY: MOD_RES
<222> LOCATION: (15)..(15)
<223> OTHER INFORMATION: Glu, Asp or Lys
<220> FEATURE:
<221> NAME/KEY: MOD_RES
<222> LOCATION: (16)..(16)
<223> OTHER INFORMATION: Gly, Ala, Ser, Thr, Leu, Ile, Val, Glu, Asp or
      Lys
<220> FEATURE:
<221> NAME/KEY: MOD_RES
<222> LOCATION: (17)..(17)
<223> OTHER INFORMATION: Gln, Asn, Arg, Glu, Asp or Lys
<220> FEATURE:
<221> NAME/KEY: MOD_RES
<222> LOCATION: (18)..(18)
<223> OTHER INFORMATION: Ala, Gly, Ser, Thr, Leu, Ile, Val, Arg, Glu,
      Asp or Lys
<220> FEATURE:
<221> NAME/KEY: MOD_RES
<222> LOCATION: (19)..(19)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (20)..(20)
<223> OTHER INFORMATION: Lys, Arg, Gln, Glu, Asp or His
<220> FEATURE:
<221> NAME/KEY: MOD_RES
<222> LOCATION: (21)..(21)
<223> OTHER INFORMATION: Glu, Asp or Lys
<220> FEATURE:
<221> NAME/KEY: MOD_RES
<222> LOCATION: (24)..(24)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (25)..(25)
<223> OTHER INFORMATION: Trp, Phe, Tyr, Glu, Asp or Lys
<220> FEATURE:
<221> NAME/KEY: MOD_RES
<222> LOCATION: (26)..(26)
<223> OTHER INFORMATION: Leu, Gly, Ala, Ser, Thr, Ile, Val, Glu, Asp or
      Lys
<220> FEATURE:
<221> NAME/KEY: MOD_RES
<222> LOCATION: (27)..(27)
<223> OTHER INFORMATION: Val, Gly, Ala, Ser, Thr, Leu, Ile, Glu, Asp or
      Lys
<220> FEATURE:
<221> NAME/KEY: MOD_RES
<222> LOCATION: (28)..(28)
<223> OTHER INFORMATION: Lys, Arg, Glu, Asp or His
<220> FEATURE:
<221> NAME/KEY: MOD_RES
<222> LOCATION: (29)..(29)
<223> OTHER INFORMATION: Gly, Ala, Ser, Thr, Leu, Ile, Val, Glu, Asp or
      Lys
<220> FEATURE:
<221> NAME/KEY: MOD_RES
<222> LOCATION: (30)..(30)
<223> OTHER INFORMATION: Arg, Lys, Glu, Asp or His
<220> FEATURE:
```

```
<221> NAME/KEY: MOD_RES
<222> LOCATION: (31)..(31)
<223> OTHER INFORMATION: Gly, Ala, Ser, Thr, Leu, Ile, Val, Glu, Asp,
      Lys or absent
<220> FEATURE:
<221> NAME/KEY: MOD_RES
<222> LOCATION: (32)..(32)
<223> OTHER INFORMATION: Arg, Lys, Glu, Asp, His or absent
<220> FEATURE:
<221> NAME/KEY: MOD_RES
<222> LOCATION: (33)..(33)
<223> OTHER INFORMATION: Arg, Lys, Glu, Asp, His or absent
<220> FEATURE:
<221> NAME/KEY: MOD_RES
<222> LOCATION: (34)..(34)
<223> OTHER INFORMATION: Asp, Glu, Lys or absent
<220> FEATURE:
<221> NAME/KEY: MOD_RES
<222> LOCATION: (35)..(35)
<223> OTHER INFORMATION: Phe, Trp, Tyr, Glu, Asp, Lys or absent
<220> FEATURE:
<221> NAME/KEY: MOD_RES
<222> LOCATION: (36)..(36)
<223> OTHER INFORMATION: Pro, Lys, Glu, Asp or absent
<220> FEATURE:
<221> NAME/KEY: MOD_RES
<222> LOCATION: (37)..(37)
<223> OTHER INFORMATION: Glu, Asp, Lys or absent
<220> FEATURE:
<221> NAME/KEY: MOD_RES
<222> LOCATION: (38)..(38)
<223> OTHER INFORMATION: Glu, Asp, Lys or absent
<220> FEATURE:
<221> NAME/KEY: MOD_RES
<222> LOCATION: (39)..(39)
<223> OTHER INFORMATION: Val, Glu, Asp, Lys or absent
<220> FEATURE:
<223> OTHER INFORMATION: provided that if Xaa31, Xaa32, Xaa33, Xaa34,
      Xaa35, Xaa36, Xaa37 or Xaa38 is absent then each amino acid
      residue downstream is also absent

<400> SEQUENCE: 32

His Xaa Xaa Gly Xaa Phe Thr Xaa Asp Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa
            20                  25                  30

Xaa Xaa Xaa Xaa Xaa Xaa Xaa
        35

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 33

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 34
<211> LENGTH: 41
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (2)..(2)
```

```
<223> OTHER INFORMATION: D-Ala, Gly, Val, Leu, Ile, Ser or Thr
<220> FEATURE:
<221> NAME/KEY: MOD_RES
<222> LOCATION: (16)..(16)
<223> OTHER INFORMATION: Gly, Glu, Asp or Lys
<220> FEATURE:
<221> NAME/KEY: MOD_RES
<222> LOCATION: (28)..(28)
<223> OTHER INFORMATION: Val or Ile

<400> SEQUENCE: 34

His Xaa Glu Gly Thr Phe Thr Ser Asp Val Ser Ser Tyr Leu Glu Xaa
 1               5                  10                  15

Gln Ala Ala Lys Glu Phe His Glu Ala Trp Leu Xaa Lys Gly Gly Pro
            20                  25                  30

Ser Ser Gly Ala Pro Pro Pro Cys Cys
        35                  40

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: His, D-His, desamino-histidine,
      2-amino-histidine, beta-hydroxy-histidine, homohistidine, alpha-
      fluoromethylhistidine, and alpha-methyl-histidine
<220> FEATURE:
<221> NAME/KEY: MOD_RES
<222> LOCATION: (2)..(2)
<223> OTHER INFORMATION: Met, Asp, Lys, Thr, Leu, Asn, Gln, Phe, Val
      and Tyr
<220> FEATURE:
<221> NAME/KEY: MOD_RES
<222> LOCATION: (15)..(15)
<223> OTHER INFORMATION: Glu, Gln, Ala, Thr, Ser or Gly
<220> FEATURE:
<221> NAME/KEY: MOD_RES
<222> LOCATION: (21)..(21)
<223> OTHER INFORMATION: Glu, Gln, Ala, Thr, Ser or Gly
<220> FEATURE:
<221> NAME/KEY: MOD_RES
<222> LOCATION: (31)..(31)
<223> OTHER INFORMATION: Gly or not present

<400> SEQUENCE: 35

Xaa Xaa Glu Gly Thr Phe Thr Ser Asp Val Ser Ser Tyr Leu Xaa Gly
 1               5                  10                  15

Gln Ala Ala Lys Xaa Phe Ile Ala Trp Leu Val Lys Gly Arg Xaa
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (30)..(30)
<223> OTHER INFORMATION: Gly or not present

<400> SEQUENCE: 36
```

```
Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Xaa
            20                  25                  30
```

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(30)
<223> OTHER INFORMATION: This sequence may encompass 1 to 6 "Gly Gly Gly
      Gly Ser" repeating units

<400> SEQUENCE: 37

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gly Gly Gly Gly Ser Gly Gly Gly Gly Ser Gly Gly Gly Gly Ser
1               5                   10                  15
```

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Gly Ser Gly Gly Gly Gly Ser Gly Gly Gly Ser Gly Gly Gly Gly
1               5                   10                  15

Ser Gly Gly Gly Gly Ser
            20
```

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 41
<211> LENGTH: 25
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 41

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Val Asp His Lys Pro Ser Asn Thr Lys Val Asp Lys Arg
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ser Gly Ala Pro Pro Pro Ser
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ser Gly Ala Ser Ser Gly Ala
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Pro Cys Pro Ser Cys
1               5

<210> SEQ ID NO 46
<211> LENGTH: 230
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
```

```
<223> OTHER INFORMATION: Ala or not present
<220> FEATURE:
<221> NAME/KEY: MOD_RES
<222> LOCATION: (16)..(16)
<223> OTHER INFORMATION: Pro or Glu
<220> FEATURE:
<221> NAME/KEY: MOD_RES
<222> LOCATION: (17)..(17)
<223> OTHER INFORMATION: Phe, Val or Ala
<220> FEATURE:
<221> NAME/KEY: MOD_RES
<222> LOCATION: (18)..(18)
<223> OTHER INFORMATION: Leu, Glu or Ala
<220> FEATURE:
<221> NAME/KEY: MOD_RES
<222> LOCATION: (80)..(80)
<223> OTHER INFORMATION: Asn or Ala
<220> FEATURE:
<221> NAME/KEY: MOD_RES
<222> LOCATION: (230)..(230)
<223> OTHER INFORMATION: Lys or not present

<400> SEQUENCE: 46

Xaa Glu Ser Lys Tyr Gly Pro Pro Cys Pro Pro Cys Pro Ala Pro Xaa
 1               5                  10                  15

Xaa Xaa Gly Gly Pro Ser Val Phe Leu Phe Pro Pro Lys Pro Lys Asp
             20                  25                  30

Thr Leu Met Ile Ser Arg Thr Pro Glu Val Thr Cys Val Val Val Asp
             35                  40                  45

Val Ser Gln Glu Asp Pro Glu Val Gln Phe Asn Trp Tyr Val Asp Gly
 50                  55                  60

Val Glu Val His Asn Ala Lys Thr Lys Pro Arg Glu Glu Gln Phe Xaa
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Gly Leu Pro
                100                 105                 110

Ser Ser Ile Glu Lys Thr Ile Ser Lys Ala Lys Gly Gln Pro Arg Glu
            115                 120                 125

Pro Gln Val Tyr Thr Leu Pro Pro Ser Gln Glu Glu Met Thr Lys Asn
        130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Xaa
225                 230

<210> SEQ ID NO 47
<211> LENGTH: 230
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (16)..(16)
```

-continued

```
<223> OTHER INFORMATION: Pro or Glu
<220> FEATURE:
<221> NAME/KEY: MOD_RES
<222> LOCATION: (17)..(17)
<223> OTHER INFORMATION: Phe, Val or Ala
<220> FEATURE:
<221> NAME/KEY: MOD_RES
<222> LOCATION: (18)..(18)
<223> OTHER INFORMATION: Leu, Glu or Ala
<220> FEATURE:
<221> NAME/KEY: MOD_RES
<222> LOCATION: (80)..(80)
<223> OTHER INFORMATION: Asn or Ala
<220> FEATURE:
<221> NAME/KEY: MOD_RES
<222> LOCATION: (230)..(230)
<223> OTHER INFORMATION: Lys or not present

<400> SEQUENCE: 47

Ala Glu Ser Lys Tyr Gly Pro Pro Cys Pro Pro Cys Pro Ala Pro Xaa
  1               5                  10                  15

Xaa Xaa Gly Gly Pro Ser Val Phe Leu Phe Pro Pro Lys Pro Lys Asp
             20                  25                  30

Thr Leu Met Ile Ser Arg Thr Pro Glu Val Thr Cys Val Val Val Asp
         35                  40                  45

Val Ser Gln Glu Asp Pro Glu Val Gln Phe Asn Trp Tyr Val Asp Gly
 50                  55                  60

Val Glu Val His Asn Ala Lys Thr Lys Pro Arg Glu Glu Gln Phe Xaa
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Xaa
225                 230

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Val

<400> SEQUENCE: 48
```

```
His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30
```

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Val

<400> SEQUENCE: 49

```
His Xaa Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30
```

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Val

<400> SEQUENCE: 50

```
His Xaa Glu Gly Thr Phe Thr Ser Asp Val Ser Ser Tyr Leu Glu Glu
1               5                   10                  15

Gln Ala Ile Ala Ala Lys Glu Phe Ile Ala Trp Leu Val Lys Gly Gly
            20                  25                  30

Pro
```

<210> SEQ ID NO 51
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Val

<400> SEQUENCE: 51

```
His Xaa Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30
```

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (2)..(2)
<223> OTHER INFORMATION: Gly or Val

<400> SEQUENCE: 52

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Val

<400> SEQUENCE: 53

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly
            20                  25                  30

<210> SEQ ID NO 54
<211> LENGTH: 30
<212> TYPE: PRT
<213> ORGANISM: Heloderma suspectum

<400> SEQUENCE: 54

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 55
<211> LENGTH: 27
<212> TYPE: PRT
<213> ORGANISM: Heloderma suspectum

<400> SEQUENCE: 55

His Gly Glu Gly Thr Phe Thr Ser Asp Leu Ser Lys Gln Met Glu Glu
1               5                   10                  15

Glu Ala Val Arg Leu Phe Ile Glu Trp Leu Lys
            20                  25

<210> SEQ ID NO 56
<211> LENGTH: 28
<212> TYPE: PRT
<213> ORGANISM: Heloderma suspectum

<400> SEQUENCE: 56

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 57
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 57

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 61
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
```

<223> OTHER INFORMATION: N-epsilon-(17-carboxyheptadecanoic acid)Lys

<400> SEQUENCE: 61

His Gly Glu Gly Thr Phe Thr Ser Asp Leu Ser Lys Gln Met Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser
        35

<210> SEQ ID NO 62
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (32)..(32)
<223> OTHER INFORMATION: N-epsilon-(17-carboxyheptadecanoyl)Lys

<400> SEQUENCE: 62

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Xaa
            20                  25                  30

Ser Gly Ala Pro Pro Pro Ser
        35

<210> SEQ ID NO 63
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (40)..(40)
<223> OTHER INFORMATION: Lys(epsilon-MPA)

<400> SEQUENCE: 63

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 64
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (40)..(40)
<223> OTHER INFORMATION: Lys(epsilon-AEEA-AEEA-MPA)

<400> SEQUENCE: 64

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser

```
                 20                  25                  30
Ser Gly Ala Pro Pro Pro Ser Xaa
        35                  40

<210> SEQ ID NO 65
<211> LENGTH: 31
<212> TYPE: PRT
<213> ORGANISM: Homo sapiens

<400> SEQUENCE: 65

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys(N-epsilon(gamma-glutamyl(N-alpha-
      decanoyl)))

<400> SEQUENCE: 66

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```